US012314385B1

(12) United States Patent
Beauchesne et al.

(10) Patent No.: US 12,314,385 B1
(45) Date of Patent: May 27, 2025

(54) AUTOMATED GENERATION OF ANOMALY SCENARIOS FOR TESTING MACHINE LEARNED ANOMALY DETECTION MODELS

(71) Applicant: Rapid7, Inc., Boston, MA (US)

(72) Inventors: Jocelyn Beauchesne, Saint-Lormel (FR); John Lim Oh, Mukilteo, WA (US); Vasudha Shivamoggi, Cambridge, MA (US); Roy Donald Hodgman, Cambridge, MA (US)

(73) Assignee: Rapid7, Inc., Boston, MA (US)

( * ) Notice: Subject to any disclaimer, the term of this patent is extended or adjusted under 35 U.S.C. 154(b) by 449 days.

(21) Appl. No.: 17/139,809

(22) Filed: Dec. 31, 2020

Related U.S. Application Data

(63) Continuation-in-part of application No. 17/024,481, filed on Sep. 17, 2020, now Pat. No. 12,088,600, and
(Continued)

(51) Int. Cl.
*H04L 9/00* (2022.01)
*G06F 11/30* (2006.01)
(Continued)

(52) U.S. Cl.
CPC ........ *G06F 21/552* (2013.01); *G06F 11/3051* (2013.01); *G06F 11/3457* (2013.01);
(Continued)

(58) Field of Classification Search
None
See application file for complete search history.

(56) References Cited

U.S. PATENT DOCUMENTS 7,689,455 B2    3/2010  Fligler et al.
7,698,071 B2    4/2010  Harris
(Continued)

OTHER PUBLICATIONS

Jonathon Shlens, A Tutorial on Principal Component Analysis, Apr. 7, 2014, Version 3.02, Google Research, Mountain View, CA.
(Continued)

*Primary Examiner* — Syed M Ahsan
(74) *Attorney, Agent, or Firm* — Ashwin Anand; Lei Sun

(57) ABSTRACT

An anomaly detection system is disclosed capable of reporting anomalous processes or hosts in a computer network using machine learning models trained using unsupervised training techniques. In embodiments, the system assigns observed processes to a set of process categories based on the file system path of the program executed by the process. The system extracts a feature vector for each process or host from the observation records and applies the machine learning models to the feature vectors to determine an outlier metric each process or host. The processes or hosts with the highest outlier metrics are reported as detected anomalies to be further examined by security analysts. In embodiments, the machine learnings models may be periodically retrained based on new observation records using unsupervised machine learning techniques. Accordingly, the system allows the models to learn from newly observed data without requiring the new data to be manually labeled by humans.

20 Claims, 39 Drawing Sheets

Related U.S. Application Data a continuation-in-part of application No. 17/024,506, filed on Sep. 17, 2020, now Pat. No. 11,509,674.

(60) Provisional application No. 62/901,991, filed on Sep. 18, 2019.

(51) Int. Cl.
| | |
|---|---|
| *G06F 11/34* | (2006.01) |
| *G06F 21/52* | (2013.01) |
| *G06F 21/55* | (2013.01) |
| *G06F 21/57* | (2013.01) |
| *G06N 20/00* | (2019.01) |

(52) U.S. Cl.
CPC ............ *G06F 21/52* (2013.01); *G06F 21/577* (2013.01); *G06N 20/00* (2019.01)

(56) References Cited

U.S. PATENT DOCUMENTS

| | | | |
|---|---|---|---|
| 8,838,511 | B2 | 9/2014 | Kristal et al. |
| 8,948,540 | B2 | 2/2015 | Robinson et al. |
| 9,210,181 | B1 | 12/2015 | Nandy et al. |
| 9,843,596 | B1 | 12/2017 | Averbuch et al. |
| 9,906,405 | B2 | 2/2018 | Mankovskii |
| 9,910,941 | B2 | 3/2018 | Dusanapudi et al. |
| 10,235,601 | B1 | 3/2019 | Wrenninge et al. |
| 10,270,788 | B2 | 4/2019 | Faigon et al. |
| 10,311,368 | B2 | 6/2019 | Lokare et al. |
| 10,372,910 | B2 | 8/2019 | Martin et al. |
| 10,599,957 | B2 | 3/2020 | Walters et al. |
| 10,645,601 | B2 | 5/2020 | Kleinbeck et al. |
| 10,743,778 | B2 | 8/2020 | Zuckerman-Stark et al. |
| 10,846,188 | B2 | 11/2020 | Tien et al. |
| 11,348,034 | B1 | 5/2022 | Jain et al. |
| 11,399,039 | B2 | 7/2022 | Rubin et al. |
| 2012/0030731 | A1 | 2/2012 | Bhargava et al. |
| 2015/0341376 | A1 | 11/2015 | Nandy et al. |
| 2016/0036837 | A1 | 2/2016 | Jain et al. |
| 2016/0078361 | A1 | 3/2016 | Brueckner et al. |
| 2017/0063907 | A1* | 3/2017 | Muddu ................. G06F 40/134 |
| 2017/0193078 | A1* | 7/2017 | Limonad ............... G06F 21/552 |
| 2017/0353477 | A1 | 12/2017 | Faigon et al. |
| 2018/0096261 | A1 | 4/2018 | Chu et al. |
| 2018/0153495 | A1 | 6/2018 | Itu et al. |
| 2018/0248904 | A1 | 8/2018 | Villella et al. |
| 2018/0319015 | A1 | 11/2018 | Sinyavskiy et al. |
| 2019/0108432 | A1* | 4/2019 | Lu ............................ G06N 3/04 |
| 2019/0124045 | A1 | 4/2019 | Zong et al. |
| 2019/0215329 | A1* | 7/2019 | Levy ...................... G06N 20/00 |
| 2020/0125734 | A1* | 4/2020 | Light ...................... G06F 17/18 |
| 2020/0379868 | A1 | 12/2020 | Dherange et al. |
| 2022/0038332 | A1 | 2/2022 | Umakanth et al. |
| 2022/0207434 | A1 | 6/2022 | Xue et al. |

OTHER PUBLICATIONS

Zhang, Li, Ding, & Zhang, Binary Matrix Factorization with Applications, Chinese Academy of Sciences, Florida International University, UT Arlington.

Lee, Huang, & Hu, Sparse Logistic Principal Components Analysis for Binary Data, 2010, vol. 4, No. 3, 1579-1601, Institute of Mathematical Statistics.

Xie, Li, & Xue, A Survey of Dimensionality Reduction Techniques Based on Random Projection, May 30, 2018.

Porwal & Mukund, Credit Card Fraud Detection in e-Commerce: An Outlier Detection Approach, May 7, 2019, ebay Inc., San Jose, CA.

Manevitz & Yousef, One-Class SVMs for Document Classification, Journal of Machine Learning Research 2, 139-154, Dec. 1, 2001.

Chen & Guestrin, XGBoost: A Scalable Tree Boosting System, Jun. 10, 2016.

Snoek, Larochelle, & Adams, Practical Bayesian Optimization of Machine Learning Algorithms.

Liu, Lafferty, & Wasserman, Sparse Nonparametric Density Estimation in High Dimensions Using the Rodeo, Carnegie Mellon University, Pittsburgh, PA.

Gillis, The Why and How of Nonnegative Matrix Factorization, Mar. 7, 2014, Universite de Mons, Belgium.

Candes, Li, Ma, & Wright, Robust Principal Component Analysis, Dec. 17, 2009.

Brochu, Cora, & Freitas, A Tutorial on Bayesian Optimization of Expensive Cost Functions, with Application to Active User Modeling and Hierarchical Reinforcement Learning, Dec. 14, 2010.

Wu & Charikar, Local Density Estimation in High Dimensions, Sep. 20, 2018.

\* cited by examiner

Approach to Find Ideal # of Dimensions

Brute force analysis on existing leaves:
- Leave out one column
- Reduce size of dataset to k in [1, 100]
- Train logistic regression to predict left out column
- Check AUC
- Iterate across all columns Predict optimal k to reach maximum AUC using Random Forest (MSE 0.25 on testing set)

AUTOMATED GENERATION OF ANOMALY SCENARIOS FOR TESTING MACHINE LEARNED ANOMALY DETECTION MODELS

This application is a continuation-in-part of U.S. patent application Ser. No. 17/024,481 titled "Machine Learning System for Detecting Anomalies in Hunt Data," filed Sep. 17, 2020, whose inventors are Jocelyn Beauchesne, John Lim Oh, Vasudha Shivamoggi, and Roy Donald Hodgman, which claims benefit of priority to U.S. Provisional Application No. 62/901,991 titled "Unsupervised Anomaly Detection Pipeline," filed Sep. 18, 2019; and is a continuation-in-part of U.S. patent application Ser. No. 17/024,506 titled "Generating Machine Learning Data in Salient Regions of a Feature Space," filed Sep. 17, 2020, whose inventors are Jocelyn Beauchesne, John Lim Oh, Vasudha Shivamoggi, and Roy Donald Hodgman, which claims benefit of priority to U.S. Provisional Application No. 62/901,991 titled "Unsupervised Anomaly Detection Pipeline," filed Sep. 18, 2019; all of which are herein incorporated by reference in their entirety.

TECHNICAL FIELD

This disclosure is related to cybersecurity computing systems. In particular, this disclosure is related to anomaly detection using machine learning models in managed detection and response (MDR) scenarios of cybersecurity computing environments.

BACKGROUND

In 2016, UBER reported that hackers stole the information of over 57 million riders and drivers. In 2017, 147.9 million consumers were affected by the EQUIFAX breach. In 2018, UNDER ARMOUR reported that its "My Fitness Pal" service was hacked, affecting 150 million users. By 2021, damages related to cybercrime is projected to hit 6 trillion dollars. As the world becomes increasingly digital, the threat of cyberattacks looms large. On a regular basis, reports surface of cyberattacks by ill-intentioned individuals or groups to obtain proprietary data and resources from companies that can be leveraged for significant profit. As a result, the cybersecurity industry has recently seen dramatic growth in the demand for third-party network monitoring and data analytics services to guard company networks against cyberattacks.

A Managed Detection and Response (MDR) service is a service that relies on the expertise of security analysts to scour metadata about a computer network to detect and respond to cyberattacks. The MDR service works by collecting large volumes of data about computers on a client network and presenting the data to cybersecurity experts to be examined for signals indicating compromise of the computers, in a process is called a "hunt." However, because the hunt process relies heavily on manual data analysis, it can be extremely slow, tedious, and error-prone. Moreover, human analysts are not always sensitive to subtle patterns in the data and cannot easily identify events associated with novel types of attacks, causing some attacks to escape detection in many cases. Better techniques are needed to improve the performance and effectiveness of the hunt process, and to reduce the amount of human analysis needed for hunts.

SUMMARY OF EMBODIMENTS

Disclosed herein are methods, systems, and processes for implementing a machine learning anomaly detection system capable of detecting anomalies (e.g. outlier processes or hosts) in hunt data gathered from a computer network. Embodiments of the anomaly detection system implement a detection pipeline comprising multiple stages, including pre-processing (e.g. feature engineering), dimensionality reduction, anomaly scoring using machine learning algorithms, and an interpretability layer. In some embodiments, the pipeline employs machine learning models that can be trained in an unsupervised manner. Accordingly, the pipeline allows the models to gradually learn from newly observed data without requiring the new data to be manually labeled. In some embodiments, the anomaly detection system will report a set number of the most anomalous processes or hosts during each observation period (e.g. determined based on a ranking of an outlier metric). Accordingly, the system is designed to surface only a small set of anomalies for each observation period, so that security analysts will not be flooded with a large volume of alerts.

Figure 1A:
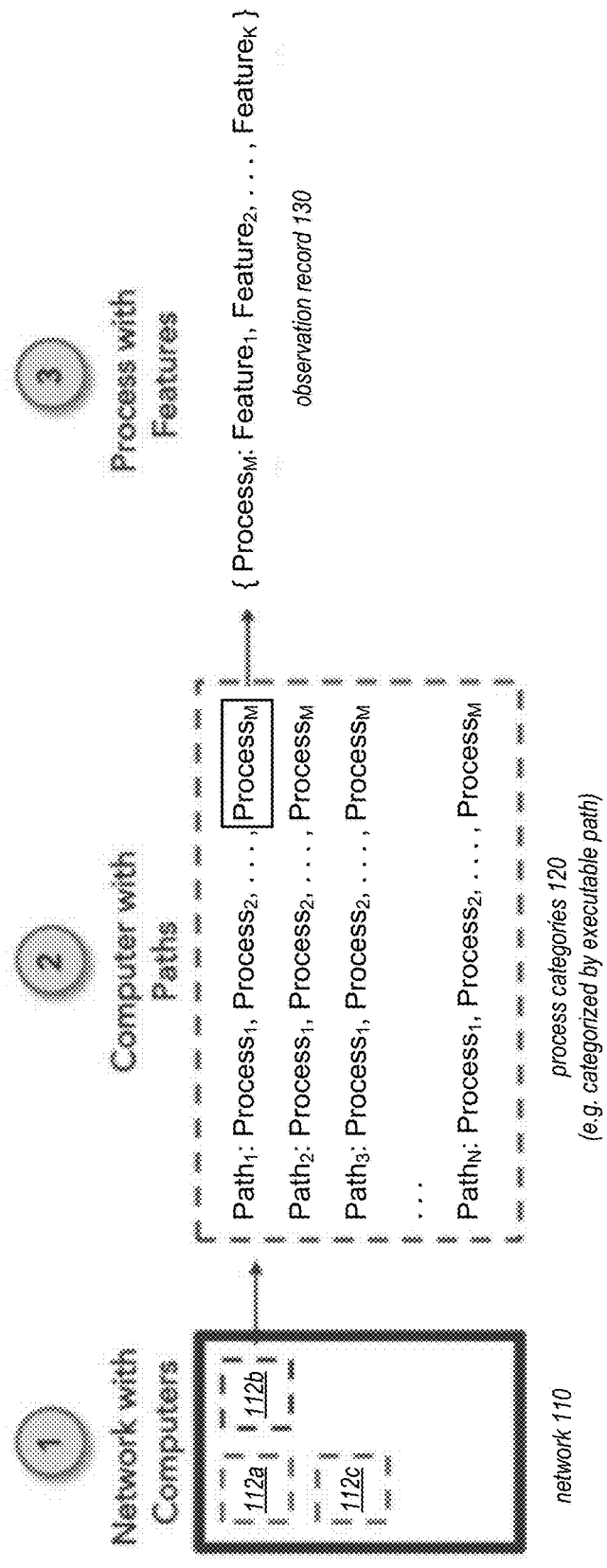
FIGS. 1A and 1B depict a block diagram 100 illustrating a tree structure used to contextualize hunt data in a machine learning anomaly detection system, according to some embodiments.

While the disclosure is open to various modifications and alternative implementations, specific embodiments of the disclosure are provided as examples in the drawings and detailed description. It should be understood that the drawings and detailed description are not intended to limit the disclosure to the particular form disclosed.

DETAILED DESCRIPTION

1. Introduction

A Managed Detection and Response (MDR) service is a service that relies on the expertise of security analysts to scour data about a computer network to extract insights about the behavior of the network. The MDR service typically works by collecting large volumes of data about computers on a client network and presenting the data to cybersecurity experts to be examined for small signals indicating compromise of the computers. This process is called a "hunt." The hunt process relies on manual analysis of a large amount of data. For example, cybersecurity technologies companies that provide MDR services such as RAPID7 of Boston, MA may collect upwards of 40 terabytes of raw hunt data over just one year.

The massive amount of hunt data poses significant challenges for cybersecurity companies that offer MDR services. Firstly, the daunting amount of data impacts the speed at which clients can find out about cyberattacks and potential breaches, exacerbating the impact to their business and their clients. Secondly, security analysts in a Security Operations Center (SOC) are having to spend a significant amount of time on mechanical tasks to manage the collected data (e.g., formatting the data) to perform a hunt, thus leaving them less time to work on higher impact tasks (e.g., running investigations based on quirks in the data). Lastly, there is little room to scale this largely manual process to consume more data or take on additional clients.

To address these and other problems of the state of the art, embodiments of a machine learning pipeline system are disclosed herein to detect outlier events in collected data of computer networks. The system improves upon conventional MDR systems by using machine learning (ML) techniques to improve the speed and efficiency of processing large amounts of data and prioritizing the investigations analysts should perform. The system allows security analysts to better utilize their time and expertise to focus on the suspicious outlier events detected by the system, and drastically reduces the amount of time it takes to detect an attack or compromise, thus minimizing the chances of potentially crippling outcomes.

Machine learning in an MDR setting is faced with a host of technology-related challenges, including the following. First, due to the manual nature of the MDR review process and the rarity of actual attacks or breaches, there is little or no labeled data, making it difficult to develop high quality anomaly detection models. Second, information about the behavior of computers in networks is particularly complex, and the observation data for hunts have extremely high dimensionality. Third, the signals for cyberattacks can evolve very quickly, as hackers can be extremely creative in devising variations of old attack methods to evade detection.

In short, security analysts are faced with the difficult task of looking for a rare signal of an attack or compromise that they are not sure exists. Worse, the analysts are not even sure what an actual signal might look like. It is a needle in the haystack problem, where the needle may not be a needle and it may or may not exist. Moreover, because the amount of data collected for a hunt can be overwhelming, it can be a challenge to filter out the noise in the data. The sheer volume of hunt data also makes the hunt process difficult to scale (e.g. to very large networks).

Accordingly, in order to address all of the aforementioned issues, the machine learning anomaly detection system disclosed herein implements a scalable yet highly granular system that is capable of detecting outliers and quantifying the associated level of risk of the outliner events. As discussed in detail below, the disclosed system provides security analysts a natural way to prioritize their work by programmatically identifying anomalies in a computer network that are indicative of threats to be examined by the hunt process.

2. Data and Natural Tree Structure 2.1 Hunt Data

As shown in FIG. 1A, an embodiment of the anomaly detection system may be used to collect hunt data from a network 110 of computers (computers 112*a-c*). Client data for a hunt process can include upwards of 40 TB of compressed data. Further breaking this down, this represents an average of 10 to 30 GB per client per month (e.g., collected over the course of a year). In some embodiments, hunt data may also include data collected from ancillary data sources (e.g., reports of known malicious activities published by companies such as REVERSINGLABS).

In some embodiments, the data retrieved by a MDR service may include data about processes that were executed on a computer. The process data may be captured in a process log and uploaded by a data collection agent to the anomaly detection system. In some embodiments, the anomaly detection system may perform pre-processing on the collected data to group the processes into a set of process categories 120. Each process category may include a set of processes that are expected to have similar execution behaviors. As shown in this example, the processes are grouped according to the file system path of the executable that was executed by the process. In some embodiments, the file system path may be normalized to remove undesired information for categorization purposes, such as a version number of the executable, or a drive letter assigned to the root of the path. In other embodiments, other types of process attributes or features may be used to group processes into categories. For example, processes may be grouped according to their executable MD5, the user who launched the process, or the time that the process was launched, etc., or some combination of such features or attributes.

In some embodiments, a process record (e.g. observation record 130) retrieved by a MDR service may include various features of a process. These features may be used to construct an input feature vector for consumption by various machine learning models of the anomaly detection system. Depending on the embodiment, these process features may include some or all of the following: (1) the command line used to launch the process on the host, including any specific options: (2) signing details or certificate used to sign the executable executed by the process by its editor to prove where it comes from, which is helpful to assess the authenticity of a software; (3) a digital fingerprint (e.g. a Message Digest 5 (MD5) value computed from the executable, which is specific to the contents of the binary file (e.g., a single change in one bit in the file leads to an entirely different string); (4) network information about the process such as Internet Protocol (IP) addresses the host or process connected to and how; and (5) information about modules that were dynamically loaded the process, including (a) the file system path of the dynamic link library (DLL) loaded, (b) the digital fingerprint or MD5 of the DLL, and (c) the name of the DLL.

In some embodiments, other types of process attributes or features may also be included in the process record 130 and used for anomaly detection. Depending on the embodiment, other process attributes or features may include the time (e.g. time of the day) when the process was launched, the length of time that the process executed, the amount of resources used by the process (e.g. CPU, memory, network, or storage usage), the identity and/or type of host that executed the process, the identity and/or type of user who initiated the process, the execution mode of the process, the termination status of the process (e.g. whether the process terminated due to an unexpected error), information about any files accessed by the process, and information about the parent process or any child process that are initiated by the process, among many others.

In some embodiments, the raw observation record 130 of a process may be encoded as a document during at least the pre-processing stage of the anomaly detection pipeline. In some embodiments, the observation record may be encoded in a bag-of-words representation, where individual attributes or features of the process are represented as distinct terms seen in the document.

2.2 Tree Structure

In some embodiments, for a specific computer program (e.g., a software program) executing on a computing device, typical program behaviors are mined using machine learning. For example, if a software program or software application is used in a malicious manner, the behavior of the program or application will deviate from baseline behaviors (e.g. the behavior of previous processes in the same process category).

In some embodiments, processes are aggregated or categorized based on the file system path of the executables across hosts and across hunts. This categorization of processes is used to at least: (1) contextualize each process to other processes that are similar (e.g., allowing a GOOGLE CHROME process to be compared to other GOOGLE CHROME processes rather than a MICROSOFT EXCEL process), and (2) mine for patterns in the data to single out outliers in each category.

Figure 1B:
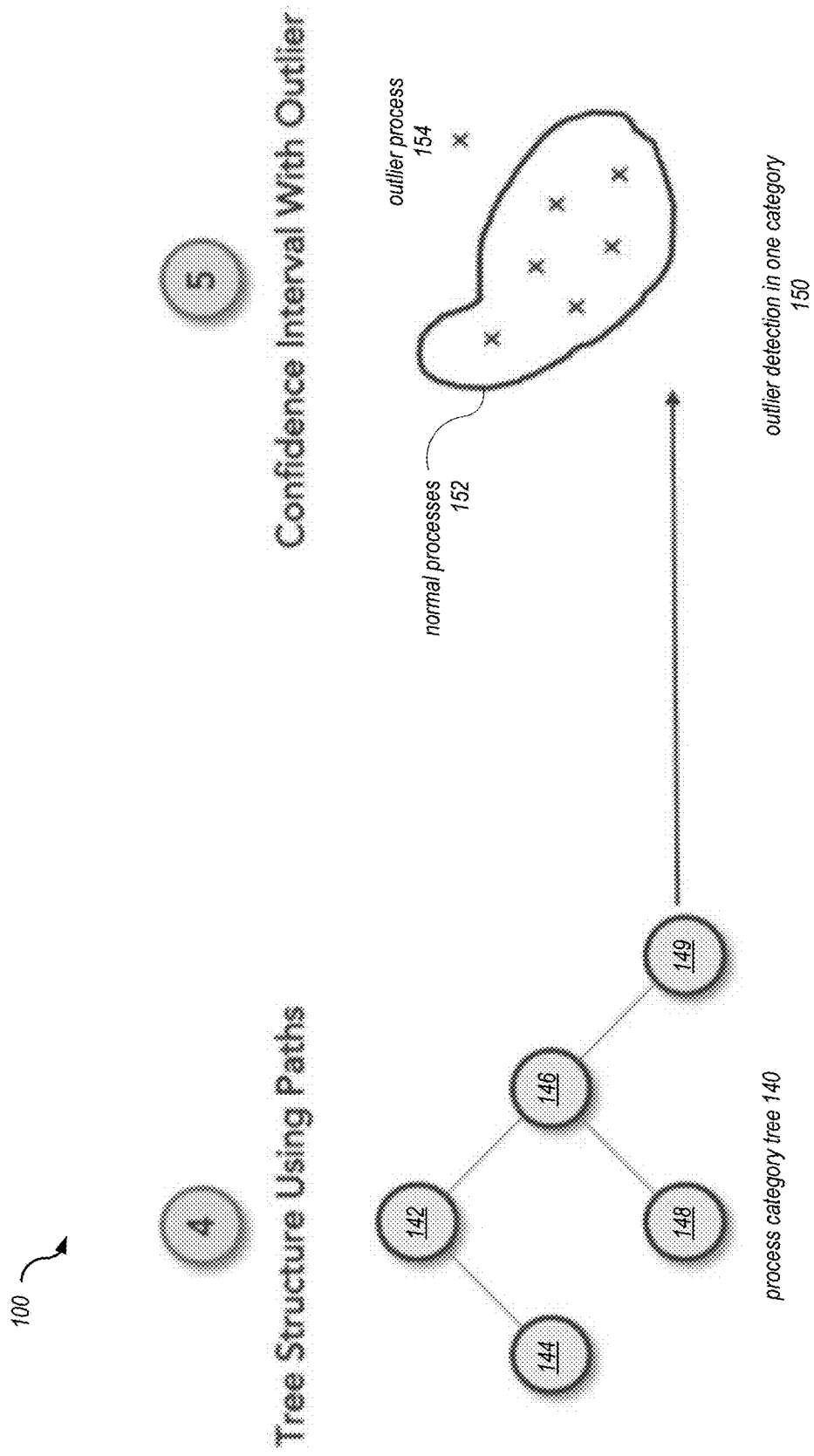

As shown in FIG. 1B, based on the natural structure of process categories 120, a tree (e.g. process category tree 140) may be created. In this example, each node 142, 144, 146, 148, and 149 may present a particular directory seen in the file system hierarchy of a host 112 in the computer network 110. In some embodiments, the individual leaves of the tree (e.g. nodes 148 and 149) represent different categories 120 of similar processes.

In some embodiments, the collected data may include a huge number of processes and process categories 120. To cope with the amount of data, in some embodiments, hosts are considered individually to aggregate processes for a given leaf. Each leaf is then merged together across all hosts to obtain a collection of all processes and features with that same path. In some embodiments, the generation of the leaves may include the following steps: (1) group dataset collected from the network by the host identifier; (2) for each sub-dataset of a host, create a tree (e.g. process category tree 140 in FIG. 1B) where each leaf contains the engineered features of all processes with the same executable path; and (3) once all the trees have been computed (e.g. via parallelized computations), the trees are recursively merged into a single tree across the hosts. In some embodiments, the leaves are stored as sparse matrices, and the merging process merges the columns of the matrices so that the columns are the same across all matrices (e.g. by padding with zeros any missing features in the individual leaf matrices).

In some embodiments, the anomaly detection system may use machine learning techniques to identify outlier processes in each process category using the sparse matrix as the input dataset. As shown in FIG. 1B, for a given observation period and a given process category 149, the anomaly detection system may perform an outlier detection process 150 to determine one or more outlier processes 154 observed during the period. The outlier process 154 may be sufficiently different from the "normal" processes 152 previously observed in the category, as determined based on one or more machine learning models.

3. Pre-Processing

3.1 Feature Extraction

In some embodiments, the anomaly detection system performs a pre-processing or feature engineering stage to extract features from the process records 130 into input feature vectors that can be used by the machine learning models. In some embodiments, the feature extraction process may be performed using: (1) binarization, where the data is casted to a binary value {0, 1} indicating the presence or absence of a process feature value, thus normalizing the data to a common format and removing question of magnitude; or (2) a TF-IDF (term frequency-inverse document frequency) process, where the feature values in the observation records are scaled according to a term frequency to identify frequency value to highlight more relevant information in the observation records.

In some embodiments, to determine the TD-IDF metric of feature values, an observation record is treated as a document, and each distinct feature value in the observation record is treated as a term. A term frequency tf(t, d) of a term may be calculated as the raw count of a term t in document d. Then, the inverse document frequency of the term may be determined using the formula:

$$idf(t, d) = \log \left( \frac{N}{\text{number of documents in corpus } D \text{ that contain } t} \right)$$

where N is the total number of documents in the corpus D. In some embodiments, the corpus D may include a body of many historical process records that are stored by the anomaly detection system. The inverse document frequency represents a measure of how rare a term is in the corpus of documents. Finally, the TF-IDF score of the term may be determined as the product of the two quantities:

$$\text{tfidf}(t,d,D) = tf \cdot idf$$

As will be appreciated by those skilled in the art, there are other methods of pre-processing text into a vector embedding to carry the relevant information, including deep learning techniques. Depending on the embodiment, these other methods may also be used by the anomaly detection system to encode the feature vectors.

In some embodiments, an observation record may be augmented with additional features about processes that are relevant to the hunt process. For example, in some embodiments, the observation record may be augmented to include a risk score associated with the executable that was executed by the process (e.g. obtained from a third party knowledgebase). In some embodiments, additional process features may be inferred from historical data. For example, the observation record may be augmented to indicate whether the process is the first time a particular executable has executed on the particular host. As another example, another feature may indicate whether the execution time of the process ranks in the top quartile of previous processes in the process category. As yet another example, a feature may indicate whether the process represents a whitelisted process that is known to be a benign process on the host. In some embodiments, these augmented features may be added to the observation record using engineered tokens before the binarization or TF-IDF steps described above.

3.2 Matrix Representation

Figure 2A:
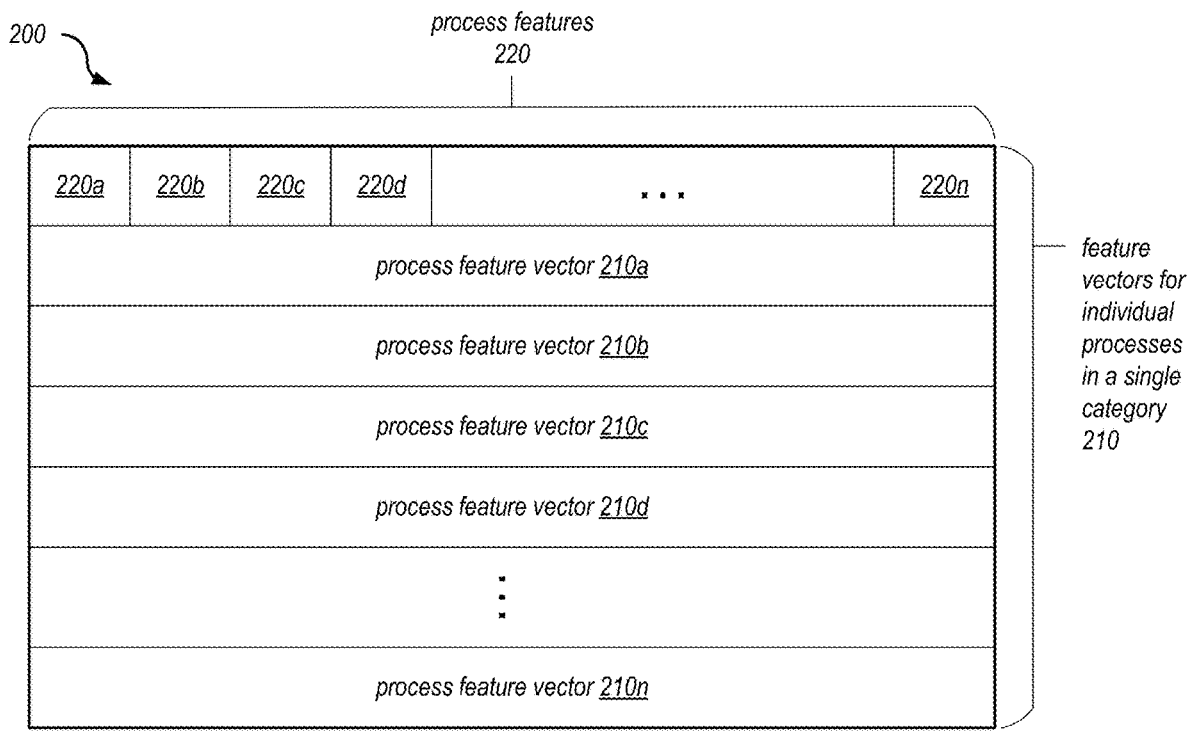
FIGS. 2A and 2B illustrate matrices of different types of feature vectors that are extracted from observation data by a machine learning anomaly detection system, according to some embodiments.
Figure 2B:
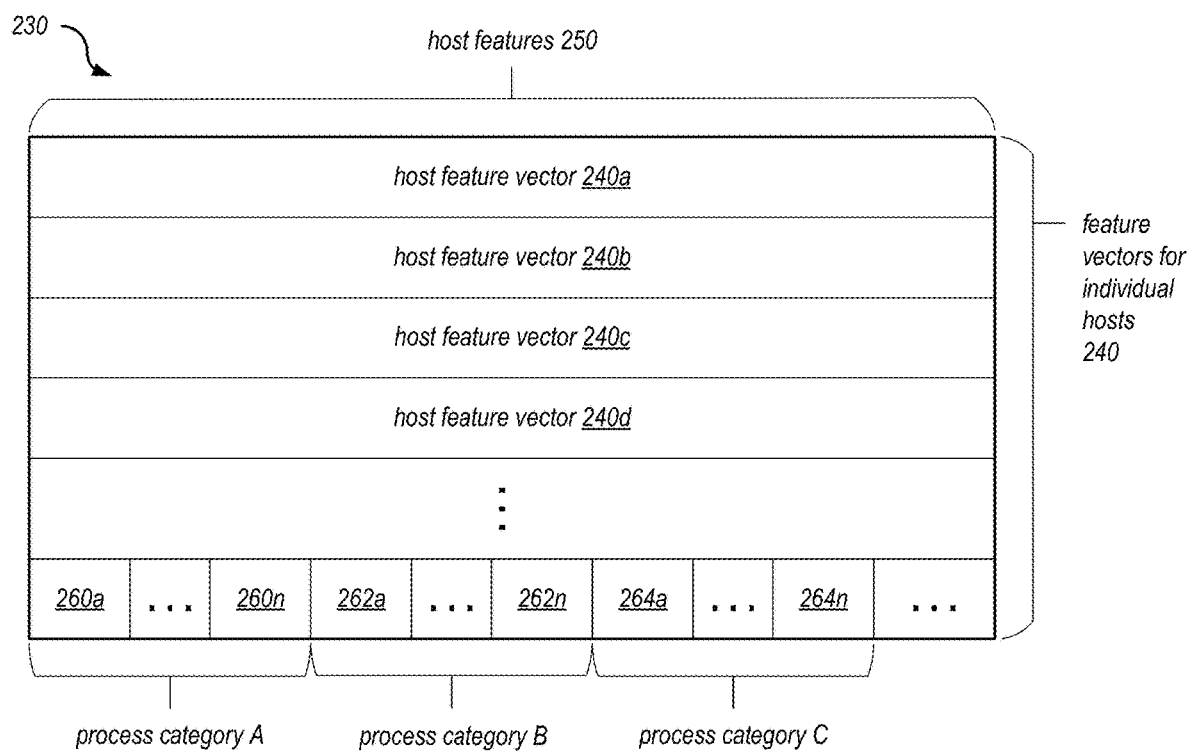

FIGS. 2A and 2B illustrate matrices of different types of feature vectors that are extracted from observation data for use by a machine learning anomaly detection system, according to some embodiments.

FIG. 2A depicts a matrix 200 that is generated from the observation records 130. The matrix 200 may be produced from the feature extraction processes described in the previous section. As shown, in matrix 200, each row 210a-n represents a feature vector for an individual process. The processes included in the matrix 200 may belong to a single process category (e.g. process category 120 of FIG. 1A). Each column 220a-n in the matrix represents an extracted feature of a process (e.g. a binary value or a TF-IDF value generated from the observation records). In some embodiments, the anomaly detection system will use machine learning model(s) to identify one or more outlier processes from the processes represented in the matrix 200.

FIG. 2B depicts another matrix 230 that may be generated by the anomaly detection systems. In this example, the rows 240a-d in the matrix 230 represent features vectors of individual hosts 112 in the network. Thus, the columns 250 in the matrix represent features of individual hosts. As shown, in some embodiments, each host feature vector 240 may include features of the different process categories 120 (e.g. features 260a-n for process category A, features 262a-n for process category B, and feature 264a-n for process category C). Features for a given process category (e.g. features 260a-n) may indicate information about processes in the category, such as the number of processes that were observed on the host for the category, any common process features for processes in the category (e.g. the path of the executable), and various aggregate features computed from the observed processes in the category. For example, an aggregate process feature may indicate the longest execution time of all processes in the category, the average number of disk accesses performed by the processes in the category, the total number of network requests by the processes in the category, etc. In some embodiments, the host matrix 230 may be constructed after an outlier detection has been performed on the observed processes. In that case, the host feature vectors 240 may include results of the process outlier detection process, such as whether an outlier was identified in each process category, and the highest outlier metric found in each process category, among other findings.

In some embodiments, the anomaly detection system will use machine learning model(s) to identify one or more outlier hosts from the hosts represented in the matrix 230. In some embodiments, the hosts in matrix 230 may represent all hosts 112 in the network 110 seen during an observation period. In some embodiments, the hosts in the matrix 230 may include a category of observed hosts that satisfy one or more category criteria.

As may be appreciated, the matrices 200 and 230 may have very high feature dimensionality (columns) due to the large number of distinct feature values observation records. For example, matrix 200 may include a column for each distinct feature value seen in the observation records (e.g. each DLL name, each MD5 value, etc.). Matrix 230 may also have high dimensionality based on the large number of distinct process categories.

3.3 Dimensionality Reduction

Figure 3A:
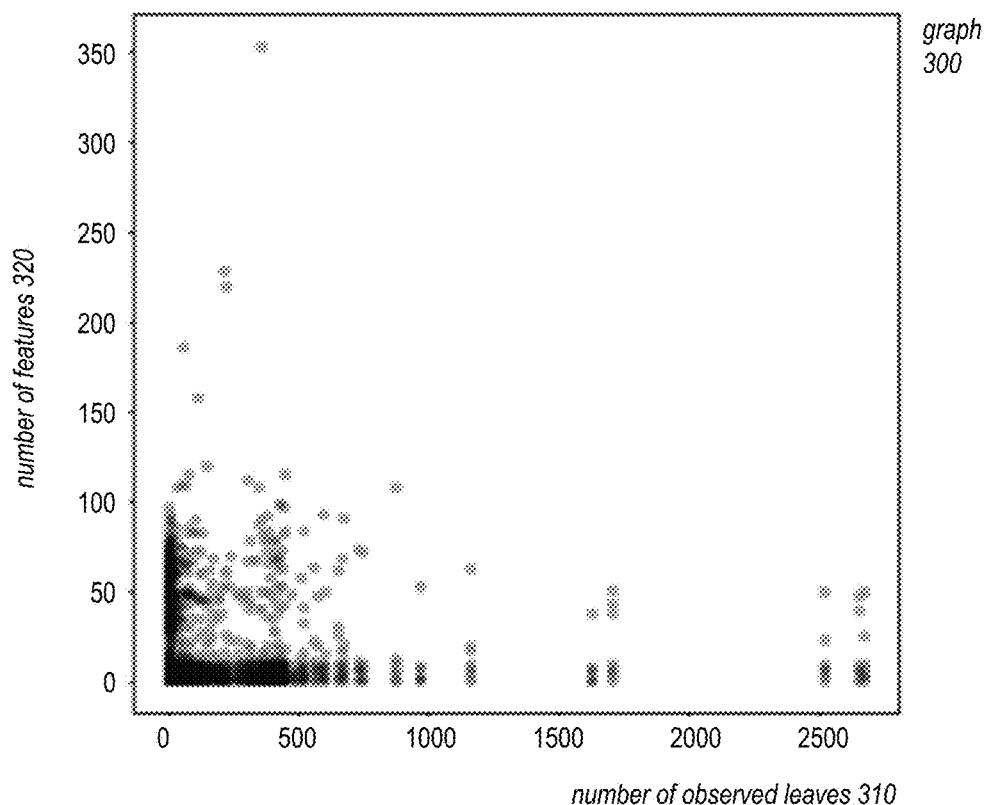
FIG. 3A is a graph 300 showing the shape of leaves of a process category tree determined by a machine learning anomaly detection system, according to some embodiments.
Figure 3B:
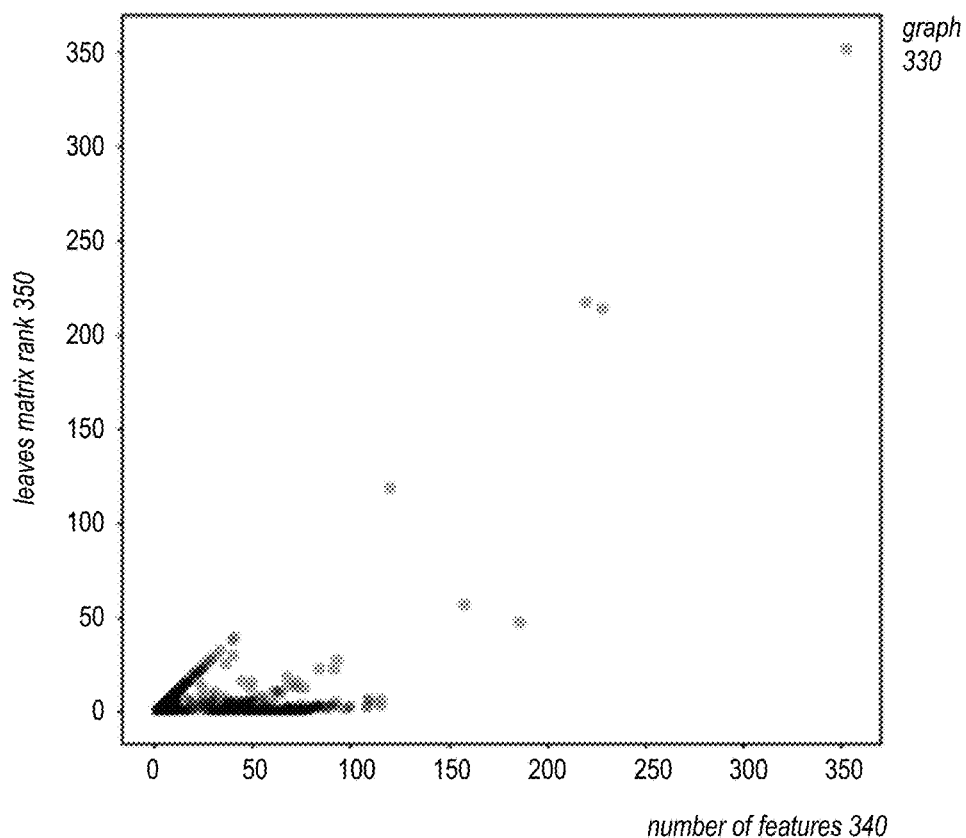
FIG. 3B is a graph 330 of the leaves matrix rank as a function of number of features determined by a machine learning anomaly detection system, according to some embodiments.

In some embodiments, given the high dimensionality of the input feature vectors under consideration (e.g., as shown in FIG. 3A), the anomaly detection system will apply one or more dimensionality reduction techniques to reduce the dimensionality of the vectors to cast the input data to a lower dimensional space (e.g., given the low rank of the leaves as shown in FIG. 3B).

FIG. 3A is a graph 300 that shows a distribution of the number of features 320 that were extracted for many observed leaves (e.g. process categories 120), according to one study. The x-axis 310 shows the frequency count of leaves that had a particular number of features. As shown, the anomaly detection system generated some leaves with large numbers of features (e.g. greater than 100 process features). This means that the matrix of feature vectors (e.g. matrix 200) is a fairly wide and sparse matrix. However, as shown in FIG. 3B, for most process categories, with their number of features shown in the x-axis 340, the "rank" of the matrix (e.g. the linearly independent features of the process category), shown in the y-axis 340, are much smaller. This result thus suggests that the feature vectors could benefit greatly from dimensionality reduction.

Depending on the embodiment, dimensionality reduction in the anomaly detection system may be performed using one or more of several methodologies. The methodologies include but are not limited to:

Principal Component Analysis (PCA);

Non-Negative Matrix Factorization (NMF), which may be adapted to positive data, with variants such as Binary Matrix Factorization (BMF);

Logistic PCA, which is type of PCA that accounts for the binary nature of the data and is particularly relevant to hunt data;

Robust PCA, which is yet another type of PCA that accounts for the potential presence of outliers in the data by taking into account the L1 norm (calculating the variance by using absolute values to diminish the impact of outliers on the data) versus the L2 norm (calculating the variance by using squared differences);

Auto Encoder, which is a type of feed-forward neural network that is trained using machine learning to approximate an identity function that maps a high-dimensional feature vector onto itself, but using an intermediate representation that has reduced dimensionality; and Randomized Projection, which uses random projection to reduce dimensionality while preserving pairwise distances, thus allowing for distance-based methods in downstream tasks.

Given the size of the hunt data, there are a number of technology-related challenges associated with assessing the effectiveness of the dimensionality reduction methods on the quality of predictions in the downstream task. These challenges are further compounded by the fact that there are no labels to measure the effectiveness of anomaly detection. Therefore, in one study, synthetic data is used to generate a regression with binary data and previous algorithms on the downstream task of the regression are compared.

Figure 4A:
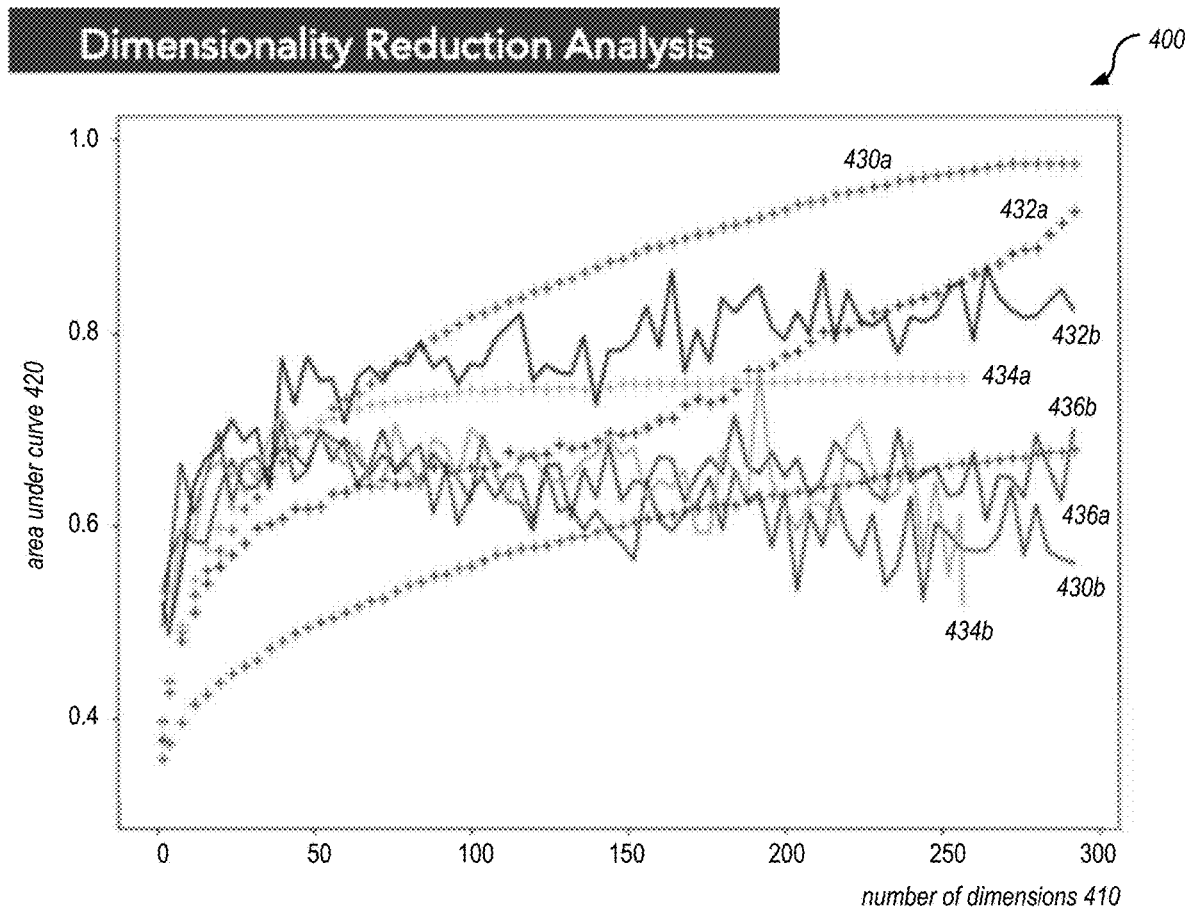
FIG. 4A is a graph 400 showing the performance of different dimensionality reduction techniques that may be used in a machine learning anomaly detection system, according to some embodiments.

The results of the study are shown in FIG. 4A. As shown in graph 400, the area under curve 420 for model accuracy metrics are plotted for datasets that were transformed using different dimensionality reduction techniques. As shown along the x-axis 410, the number of resulting dimensions 410 of the dataset was also varied, so that the graph shows how the ultimate model performance varied with the magnitude of dimensionality reduction. In the graph 400, curves 430a and 430b are the performance results for PCA, curves 432a and 432b are the results for NMF, curves 434a and 434b are the results for BMF, and curves 436a and 436b are the results for randomized projection. In the graph 400, the dotted lines 430*a*, 432*a*, 434*a*, and 436*a* represent explained variance, and the solid lines 430*b*, 432*b*, 434*b*, and 436*b* represent accuracy.

In the study, it is determined that NMF not only performs the best (on average), but also offers better resistance to dimensionality. Moreover, the results indicated that PCA tended to remove small perturbations (as discussed later with respect to scenario-based model testing). At least for these reasons, Robust PCA may be used as a preferred method for dimensionality reduction to get the best of both worlds by extracting a general low rank matrix L as well as a sparse matrix S denoting potential anomalies. However, if computing power is a limiting factor, PCA may be used instead of Robust PCA as a preferred method.

In some embodiments, the anomaly detection system may be configured to support multiple types of dimensionality reduction methods. The anomaly detection system may be configured to select one or more of the dimensionality reduction methods at runtime, either automatically based on runtime conditions (e.g. recent model evaluation results), or based on configuration settings specified by analysts. In some embodiments, the dimensionality reduction models used by the anomaly detections system may be periodically updated using unsupervised machine learning techniques, so that no manually labeling of the data is required. In this manner, the dimensionality reduction models can be gradually adapted to the hunt data with little or no human supervision.

3.2 Finding the Best Number of Dimensions

A significant task when performing dimensionality reduction is to tune the number of dimensions of the final space. However, given that the available data for the downstream models are not labeled, a critical metric is missing to evaluate the downstream tasks to determine the right value of this hyper-parameter.

Figure 4B:
FIG. 4B illustrates a technique to determine an ideal number of dimensions for dimensionality reduction used in a machine learning anomaly detection system, according to some embodiments.
Figure 4B:

Therefore, in some embodiments, columns of the binary dataset are bootstrapped over and the columns are considered as labels of a binary classification algorithm. In this example, anomalies will likely be noticeable through variations in a column and therefore, this is an acceptable proxy to assess the ability to retrieve this information after dimensionality reduction. FIG. 4B shows a summary of this technique to determine the ideal number of dimensions for dimensionality reduction.

As shown in the example, for each leaf, for each column c, for each possible dimension k, at least the following is performed: (1) reduce feature dimensionality to dimension k on columns of the leaf, but excluding column c; (2) training a classifier to predict c based on the data of the previous step; and (3) computing the area under the curve (AUC) of this trained classifier on the left out data. The k that works best on average and gives the best AUC is then selected as the best dimension.

However, in some embodiments, the foregoing process can be very time consuming. Therefore, in some embodiments, a regression algorithm is trained on one or more metrics related to the data (such as matrix rank, sparsity, dimensions, etc.) to predict the associated k. In this manner, computing resource heavy calculations are avoided in production, while an effective predicted value of k is obtained fairly quickly (e.g., with a mean squared error (MSE) of 0.22 for normalized data).

Furthermore, the dimension value determined by the disclosed technique is generally stable and produces close-to-ideal values of k for a wide range of possible dimensions, leading to 95% of the optimal model performance in the anomaly detection system. Therefore, despite the variance in the predictor due to the imperfectness of the input, the technique can be used to generate close-to-optimal values of the dimension k for dimensionality reduction.

3.3 Reducing Dimensionality Based on Feature Value Variability

In some cases, an observation dataset may include certain observed features with widely dispersed feature values. For example, the observed launch time for a particular type of process may be evenly dispersed across all time periods during the day. A feature with high value dispersion is typically not very useful for anomaly detection, because no particular value of the feature is obviously "anomalous." Thus, in some embodiments, the anomaly detection system is configured to examine individual features in the dataset to eliminate features that are highly dispersed or variable in terms of their observed values. The value variability of a feature may be quantified using a feature variability metric. Features with high variability are not used to train anomaly detection models, so the models do not take these features into account when making their anomaly assessments. Using this approach, the complexity of the anomaly detection models can be significantly reduced, allowing the models to be trained and executed more quickly and without sacrificing the models accuracy. In some embodiments, feature reduction using feature value variability may be performed automatically without any human intervention.

Figure 5:
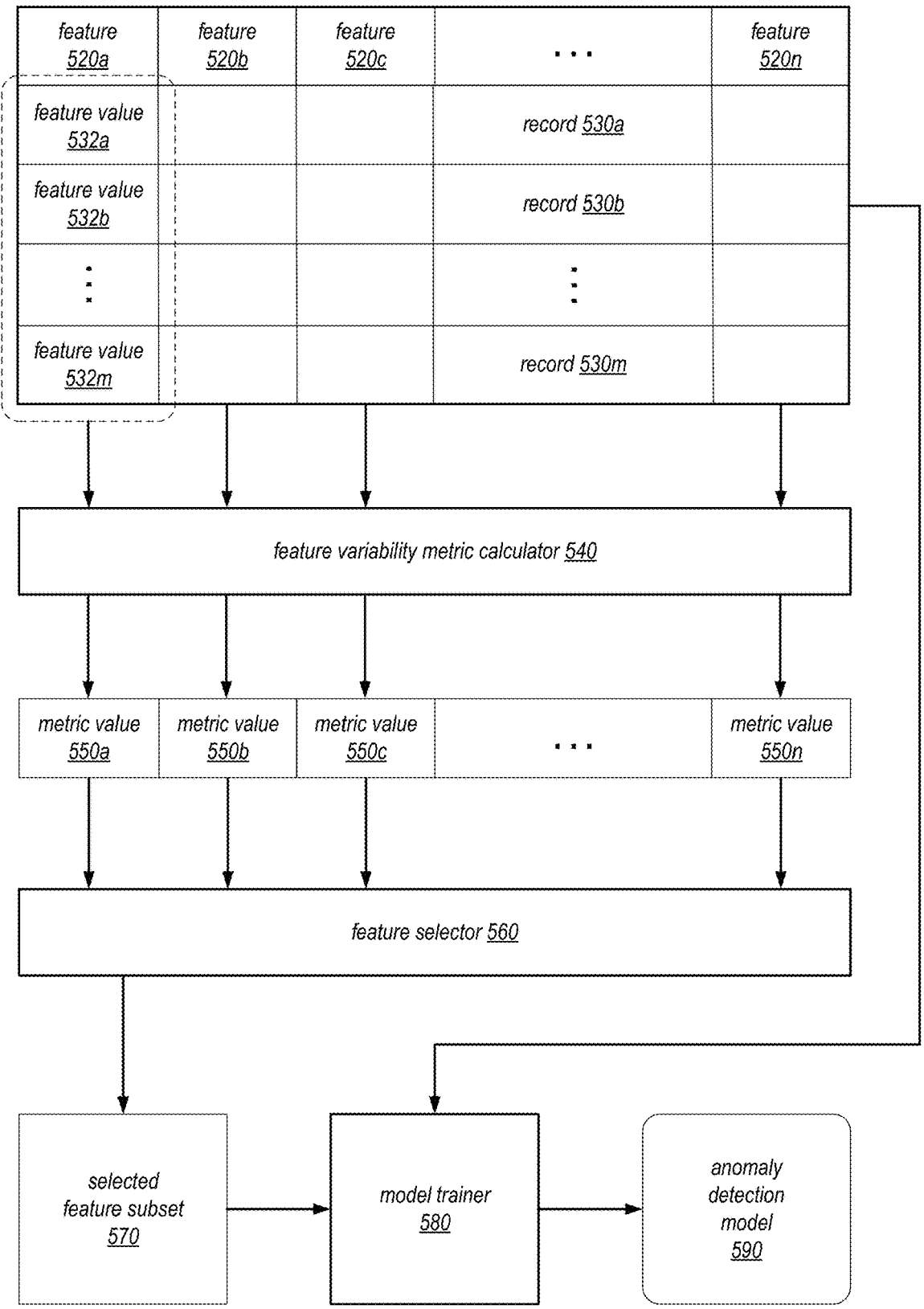
FIG. 5 illustrates operations of an automated dimensionality reduction process used by a machine learning anomaly detection system to select features to train anomaly detection models, according to some embodiments.

FIG. 5 illustrates the operations of an automated dimensionality reduction process used by a machine learning anomaly detection system to select features for training anomaly detection models, according to some embodiments. The observation dataset 510 may be a dataset similar to datasets shown in FIG. 2A or 2B. In some embodiments, the observation dataset 510 may be an input vector that is produced by a prior dimensionality reduction technique, such as PCA, NMF, Auto Encoder, etc., as discussed previously.

As shown, the dataset 510 includes many observation records 530*a*, 530*b*, to 530*m*, where each record 530 includes a set of features 520*a*, 520*b*, 520*c*, to 520*n*. Each feature (e.g. feature 520*a*) may have respective features values 532*a*, 532*b*, to 532*m* for individual observation records 530.

As shown, the anomaly detection system in this example implements a feature variability metric calculator 540, which calculates a metric value 550*a*, 550*b*, 550*c*, to 550*n* for each feature 520 in the observation dataset 510. The feature variability metric will measure how dispersed or variable the values of a particular feature are. In some embodiments, the feature variability metric may be based on the standard deviation or variance of the feature. In some embodiments, the feature variability metric may indicate a ratio between the range of observed values of the feature and the entire value range of the feature, so that features with concentrated observations in narrow ranges will have a lower dispersion value. In some embodiments where the feature is a binary value (e.g. a single bit), the feature variability metric may be the expected value of the bit (e.g., the average of 1s and 0s observed for the feature). Binary features with average values closer to 1 or 0, as opposed to 0.5, may be considered to be more useful features for anomaly detection. In some embodiments, the metric values of different features may be normalized so that they can be directly compared. For example, if two continuous value features have different value ranges, the standard deviation or variance of the two features may be normalized to a common range.

In some embodiments, the feature variability metric calculator 540 may use every observation record 530 when computing the feature variability metric. In some embodiments, the calculator 540 may randomly sample a subset of observation records 530 from the dataset 510 to determine the feature variability metric. In some embodiments, the calculator 540 may randomly select a subset of the features 520 in the dataset 510 to evaluate for possible feature reduction. In some embodiments, the functioning of the calculator 540 may be configurable via a configuration interface of the anomaly detection system. For example, the configuration interface may allow an administrator to adjust settings such as which features in the dataset are to be evaluated for feature reduction, which portions of an observation record or feature vector constitutes a "feature," and how to normalize the metric across different features, etc.

As shown, the metric values 550 calculated for each analyzed feature are provided to a feature selector component 560, which will eliminate some of the features from the anomaly detection process based on their feature variability metric values 550, and retain a subset 570 of the features to use for anomaly detection. In some embodiments, the selector 560 may compare the metric value 550 of each feature against a threshold, so that features with variability values above the threshold are excluded from the subset 570. The threshold may be different for different features. For example, if the standard deviation is used as the variability metric, the threshold value may be determined based on the value range of the feature. In some embodiments, the selector 560 may rank the metric values 550 of different features (e.g. from the lowest value to the highest value) and retain a specified number of least variable features as the subset 570. In some embodiments, the selection process implemented by the feature selector 560 may take into account other factors, such as the encoding size of the feature, the value range of the feature, the feature's correlation with other features, etc. Such selection factors may be configurable via the configuration interface. In some embodiments, the selection process may include a random component, so that the feature selector 560 will select different subsets 570 of features based on the same selection factors.

As shown, in some embodiments, the selected feature subset 570 will be used by a model trainer component 580 to train one or more anomaly detection models 590, which will be used to detect anomalies or outliers in subsequent observation datasets. In some embodiments, the selected feature subset 570 may be further reduced using one or more other dimensionality reduction techniques, such as the techniques discussed in connection with FIG. 4A. In some embodiments, the anomaly detection system may maintain an ensemble of anomaly detection models, and periodically train new models for the ensemble using one or more unsupervised machine learning techniques. Each new model may be trained using a different set of features selected based on their feature variability metric in the manner described above.

Figure 6:
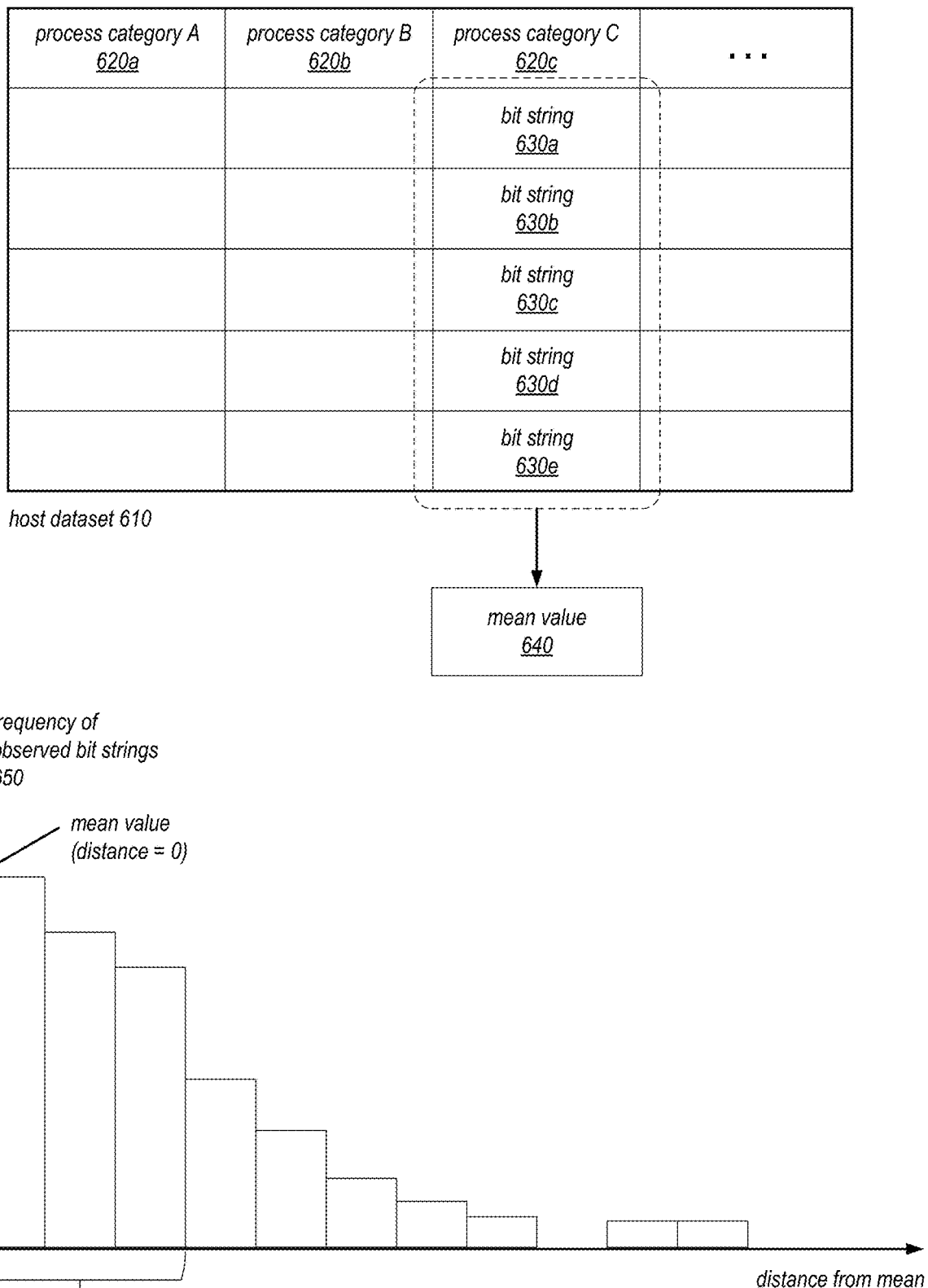
FIG. 6 illustrates operations of an automated dimensionality reduction process used to select features encoded as bit strings in a machine learning anomaly detection system, according to some embodiments.

FIG. 6 illustrates operations of an automated dimensionality reduction process used to select features encoded as bit strings in a machine learning anomaly detection system, according to some embodiments. The figure depicts a particular type of feature variability metric that can be used to compare features encoded as bit strings.

As shown, the top portion of FIG. 6 shows a host dataset 610, which may be encoded as a matrix 230 as discussed in connection with FIG. 2B. As discussed, such a host dataset may include records that represent individual hosts or machines monitored during a time period, and the features of the records will indicate the presence or absence of a type of observed process type (e.g. process categories 620*a-c*) on the host or machine. As shown, each process category 620 may be encoded as a bit string (e.g. bit string 630*a-c*). The bits in the bit strings 630 may indicate additional observed characteristics of the process category of a particular machine, such as a count of instances of the process category, whether any of the process instances sent data over a network, whether the process instances were identified as an outlier process instance within its process category, etc.

As shown, the dimensionality reduction process may determine a mean value 640 of the observed bit string values in the dataset. In some embodiments, the mean value 640 may indicate an average of the bit string values 630*a-e*. For example, in some embodiments, the mean value may be a vector that indicates an average of each bit (e.g. a value between 0 and 1) in the bit strings 630*a-e*. As another example, the mean value may be a generated bit string where each bit is set to 0 or 1 according to the most common value seen for that bit in the bit strings 630*a-e*. As yet another example, the mean value may be the most commonly seen bit string in bit strings 630*a-e*.

The bottom portion of the figure shows how the mean value 640 may be used to derive the feature variability metric 670 for the feature (process category 620*c*). As shown, a distance 660 is computed between each bit string instance 630 in the dataset to and mean value 640. In this example, the distances are all positive. In other embodiments, the distance may be both positive and negative. In some embodiments, the distance 660 may be the Euclidean distance between the mean value and a bit string. In some embodiments where the mean value is also a bit string, the Hamming distance of the two bit strings may be used. The resulting distances are plotted to show a distribution of frequencies 650. As shown in this example, the feature variability metric 670 is computed based on the standard deviation of the distribution. The standard deviation will be smaller for process categories whose bit string values are more tightly clustered around the mean value, and larger for process categories whose bit string values are more dispersed. In some embodiments, feature variability metric 670 may be used to select a subset of process categories 620 to use for detection of anomalous or outlier hosts.

4. Machine Learning Models

In some embodiments of the anomaly detection system, the outliers in the hunt data are identified using one or more of the following machine learning models.

4.1 Isolation Forest

In some embodiments, Isolation Forest, which is based on the process and structure of a Random Forest, is used by the anomaly detection system to detect outliers. Isolation Forest models are built on the notion that there are only a few outliers and that they are different from the rest of the data. Under this hypothesis, an Isolation Tree (e.g. tree 710*a-c* in FIG. 7) is built by recursively splitting features space randomly and then computing the depth for each individual point. There is an assumption here that shorter paths in the tree are likely to be associated with anomalies because they are more likely to be sectioned off by an early cut or split.

Figure 7:
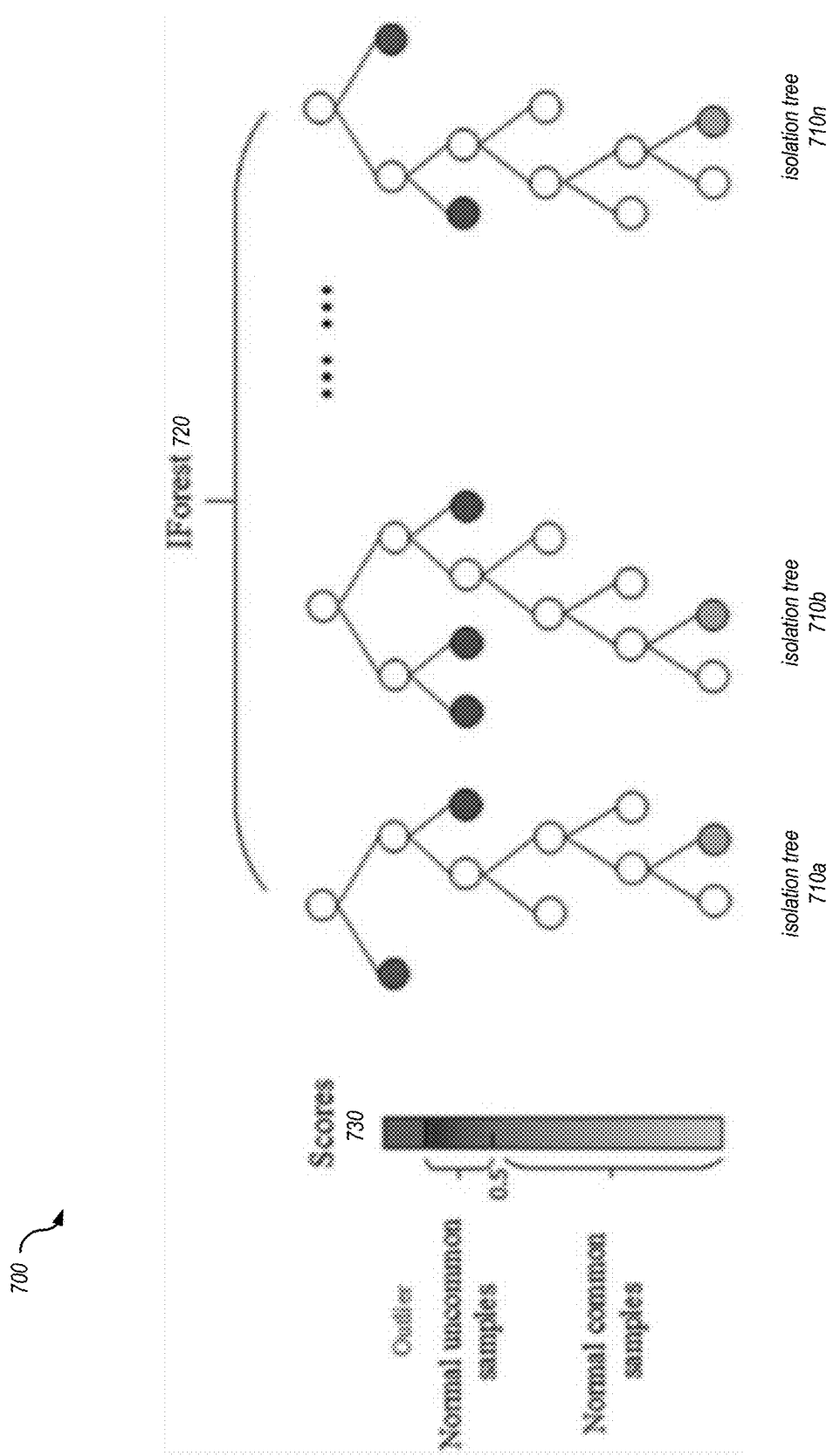
FIG. 7 is an illustration 700 of a visualization of Isolation Forest model that may be used in a machine learning anomaly detection system, according to some embodiments.

As shown in FIG. 7, a number of Isolation Trees 710*a-c* are used, where each tree selects a random sample size and set of features, which are then merged into an Isolation Forest 720. The outlier score produced by the Isolation Forest 720 may be an average of the depths across each Isolation Tree 710*a-c* to reduce variance. The score is mapped to a score range 730, which may be calibrated based on scores of historical processes or hosts in the relevant category. In some embodiments, the ranking of a score in the range 730 may be used as the outlier metric of the particular process or host.

In some embodiments, it is observed that Isolation Forest may not perform optimally with highly-dimensional, sparse, and binary data. One reason behind this observation may be that a single flipped bit is not easily caught by the Isolation Trees, as the probability of splitting on it is inversely proportional to the dimension of the space and can therefore rarely influence the depth of such an anomaly within an Isolation Forest. This can make it difficult to pick up anomalies through the Isolation Forest methodology. Therefore, in order to improve the accuracy of Isolation Forest models, it may be necessary to first implement dimensionality reduction using the algorithms discussed earlier, in some embodiments.

4.2 One-Class Support Vector Machine

Figure 8:
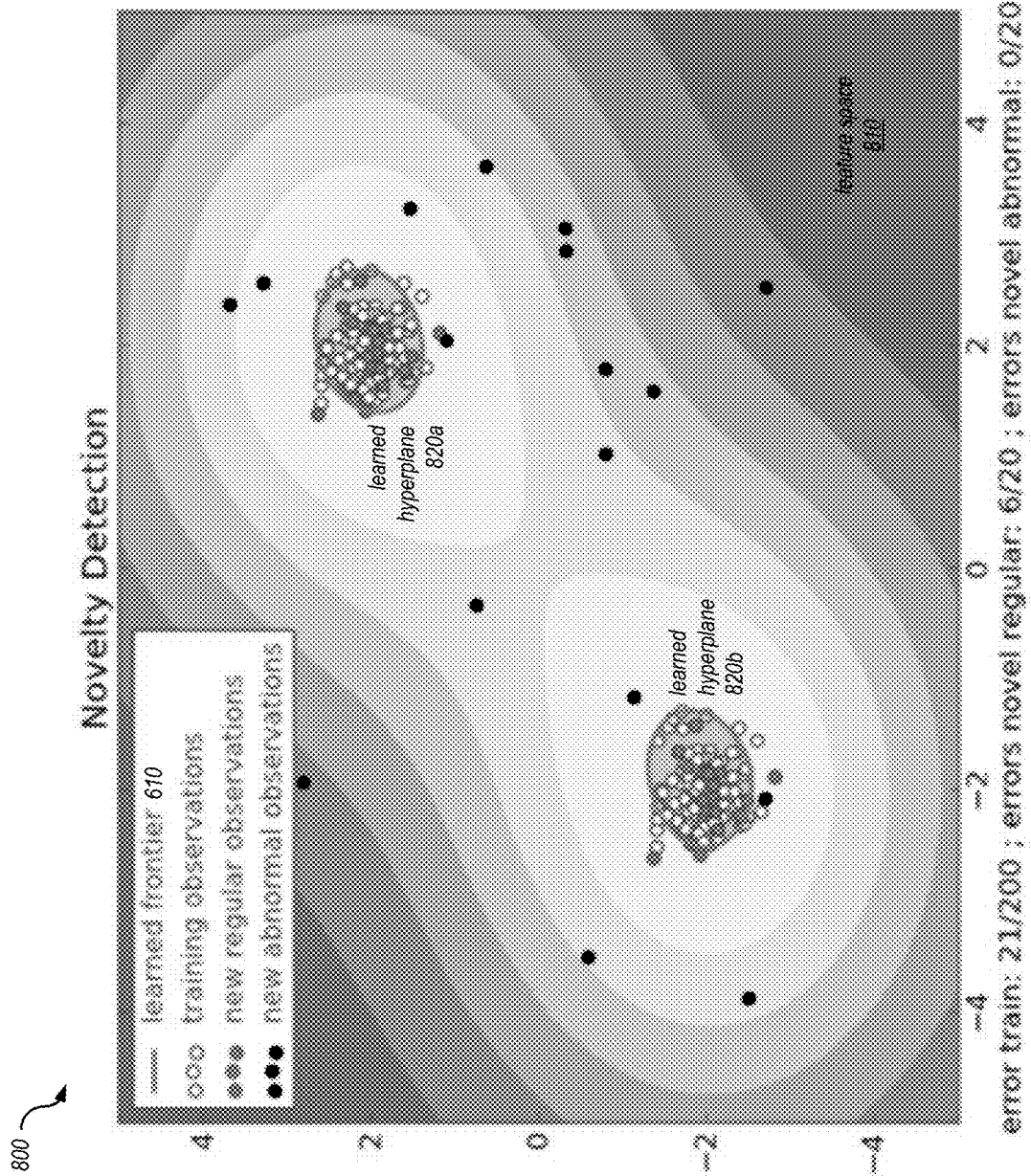
FIG. 8 is an illustration 800 of a visualization of One-Class SVM that may be used in a machine learning anomaly detection system, according to some embodiments.

In some embodiments, the anomaly detection system may be configured to use a One-Class Support Vector Machine (SVM) as an outlier detection model. A One-Class SVM is an unsupervised machine learning algorithm similar to the general SVM in terms of formulation. A SVM is a classifier trained to discriminate data based on separating hyperplanes. In other words, given labeled training data (supervised learning), the algorithm outputs an optimal hyperplane which categorizes new examples. In a two-dimensional space, this hyperplane is a line dividing a plane in two parts where the classes lay on different sides of the line. With One-Class Support Vector Machines, the main subtlety is that there is only one class and most of the data is enclosed on one side on the learned hyperplane. One-Class SVMs are trained using an unsupervised machine learning technique without labels, and these models may be trained to learn a frontier between normal and outlier data points. FIG. 8 illustrates a feature space 810 projected into two dimensions for easier visualization. As shown, the figure depicts a number of observations in the feature space (e.g. process feature vectors 210 or host feature vectors 240), and a hyperplane 820 learned by an example One-Class SVM, and an One-Class SVM's performance in detecting abnormal or outlier observations based on the hyperplane.

4.3 Classifier Trained to Distinguish Real and Synthetic Data

Figure 9:
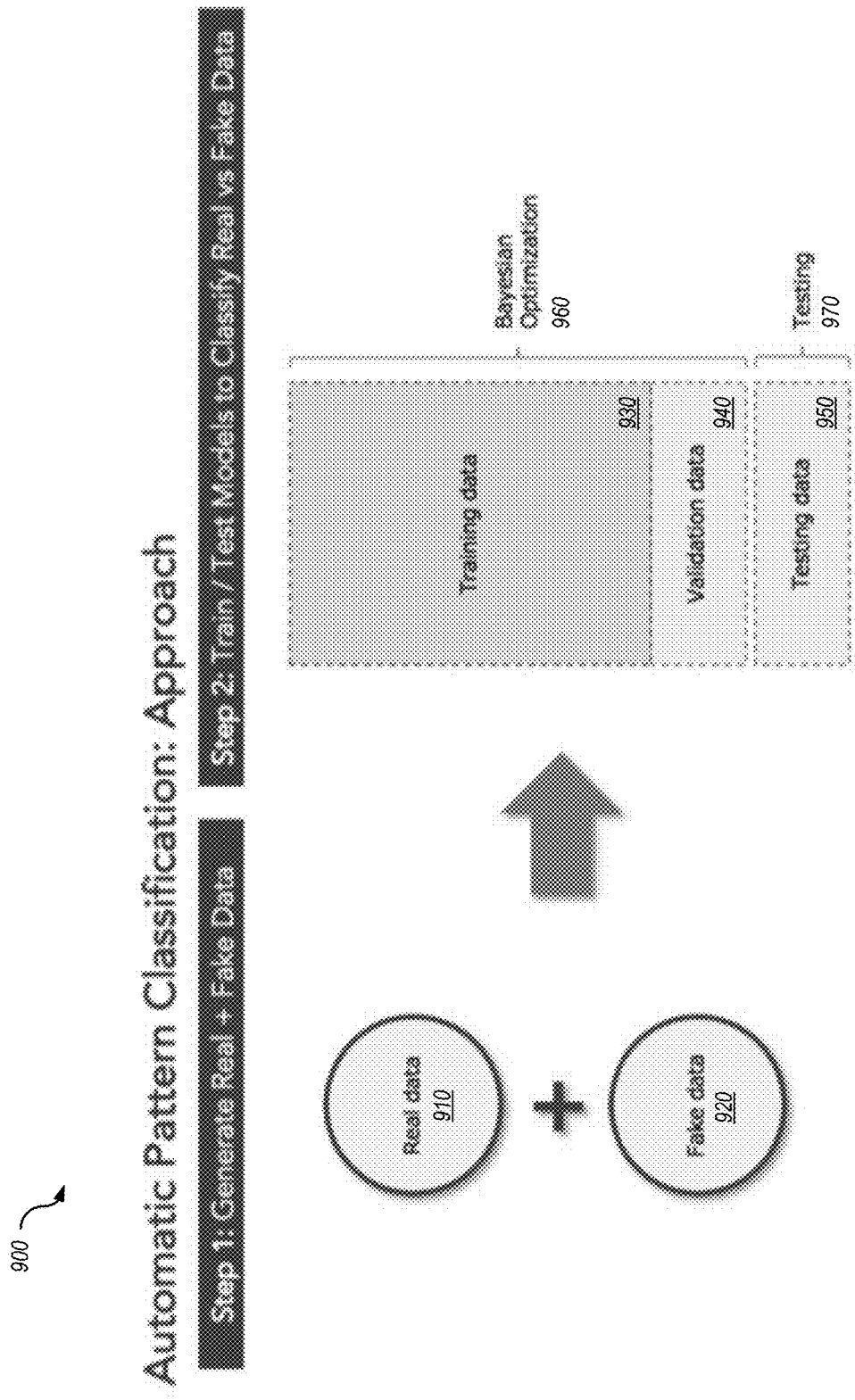
FIG. 9 is a block diagram 900 of an approach to automatic pattern classification that may be used in a machine learning anomaly detection system, according to some embodiments.

In some situations, patterns in the observation data may be mined by comparing the actual data to synthetic data that is generated in the same space. FIG. 9 depicts an approach to automatic pattern classification that may be used to build a classifier model used by the anomaly detection system to detect outliers. As shown, the approach first generates fake or synthetic data 920. In some embodiments, the synthetic data may be uniformly distributed across the feature space. The synthetic data 920 is combined with real data 910 to create a dataset used to train a classifier model. Assuming that the actual observation data is non-random, the classifier can be trained to distinguish between the real data 910 and the fake data 920. In turn, the trained classification model can be used to provide outlier scores for new data points (e.g. based the confidence that a new data point is a real data point).

For example, in some embodiments, an assumption is made that 95% of a real dataset X is expected to lie within a connected and convex volume V, where V is the smallest subset that verifies this property. Next, the smallest hypercube H that contains V is obtained, which increases the size of V and constructed to have the same mean as V. Points in H may be sampled to generate the synthetic data points, which are labeled as 1. The points of the real dataset are labeled 0. A non-linear classifier, such as a Random Forest, may then be trained on a balanced subset of real and fake data to learn the volume V within H. Based on this training, this classifier will be able to learn the frontiers of the volume V to separate the real data 910 from fake data 920. The learned frontier may then be used to detect outliers that deviate from the 95% of the "normal" data.

4.3.1 A Classification Task

Now that the problem of anomaly detection is characterized as a classification task, one of a number of machine learning classification models may be used. Example classification models include K-Nearest Neighbors (KNN), Random Forest, Logistic Regression, XGBoost, Support Vector Machine, or Neural Networks. One downside of this approach is that when the data is very high-dimensional, the randomly generated synthetic data may not adequately cover the feature space due to the large dimensionality. However, this problem is mitigated to a degree by using the dimensionality reduction techniques discussed earlier. Note that, although the classification model is trained using labeled data, in this case, the labeling is performed automatically by the computer system. Thus, this approach does not require any manual labeling of data as outlier or non-outlier.

4.3.2 Bayesian Optimization

As shown in FIG. 9, in some embodiments, in order to train the classifier model automatically, the real data 910 and fake data 920 are concatenated into a single dataset, and split in a desired manner into a training dataset 930, a validation dataset 940, and a testing dataset 950. Then, for a given set of hyper-parameters the classifier is trained on the training set 930. The AUC on the validation set 940 is reported on the resulting classifier. In some embodiments, a Bayesian Optimization framework 960 is used to select a next point of hyper-parameters to evaluate. After some number of training-validation iterations performed according to the Bayesian Optimization framework, the trained model may be tested 970 on using test dataset 950 before reporting AUC.

4.3.3 Generating More Useful Synthetic Data

In many cases, it is important to generate good synthetic data that will be instructive for model training. However, a random approach to generating synthetic data often does not produce a good dataset. For example, if the feature space is particularly large in terms of dimensionality and if actual observations occupy a relatively small area in the feature space, randomly generating synthetic data in the space will generally fail to provide sufficient coverage in the salient regions of the features space (e.g. regions near the frontiers of observed data). Most of the synthetic data will be generated in regions that are far away from where the actual observations reside. Such randomly generated synthetic data are not very useful for training a model to learn the frontiers of the data or testing the model's ability to detect the frontiers.

Additionally, it is sometimes useful for data scientists to specify desired characteristics of a frontier to be learned by a model, such as how far a learned frontier should extend from the center of the observed dataset. However, it is generally difficult to specify such characteristics using conventional data generation techniques.

In order to solve the foregoing problems, in some embodiments, the anomaly detection system implements a synthetic data generation system that uses density estimation to generate useful synthetic data points in salient areas of the feature space. The disclosed technique can be used to mitigate the problems of inadequate coverage that can result from purely random synthetic data generation. Moreover, the disclosed technique can be controlled so that the synthetic data is generated in particular regions to encourage the learning of desired frontiers in the data. The disclosed process produces better datasets for machine learning and results in faster training times and better models.

Figure 10:
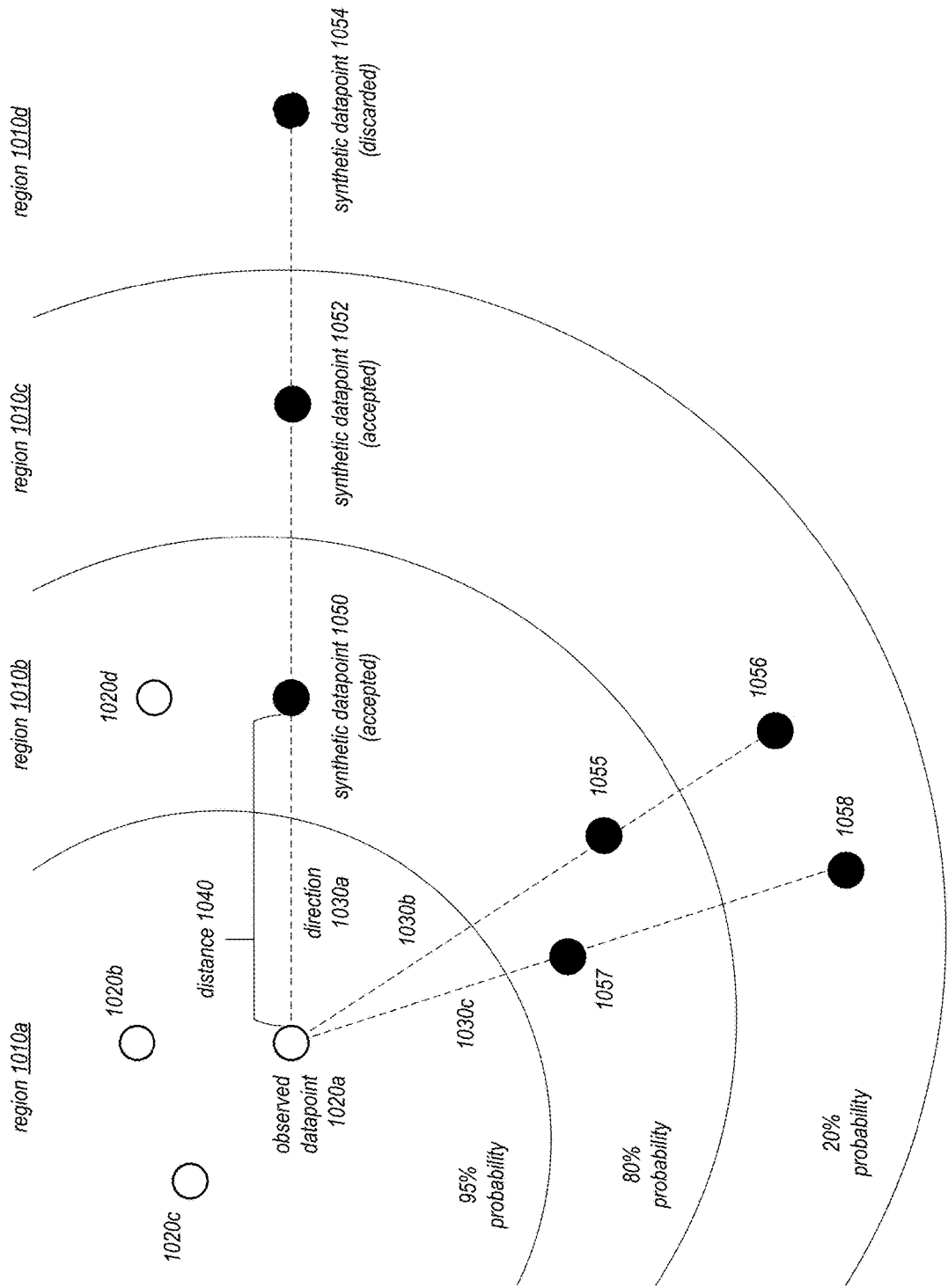
FIG. 10 illustrates a technique for generating synthetic data to train and evaluate machine learning models in a machine learning anomaly detection system, according to some embodiments.

FIG. 10 illustrates a technique for generating synthetic data to train and evaluate machine learning models in a machine learning anomaly detection system, according to some embodiments. As shown, the figure depicts a feature space 1000, which for illustration purposes is shown here in two dimensions. In practice, the feature space 1000 may be a feature space of high dimensionality, having hundreds or thousands of dimensions.

As shown, a dataset of observed data points, including data points 1020a-d shown in white, exist in the features space 1000. In some embodiments, the observed data points 1020 may be feature vectors to be analyzed by the outlier detection models used by the anomaly detection pipeline. In some embodiments, these data points 1020 may encode behaviors of hosts, such as processes or process categories observed on the hosts.

In some embodiments, a density function may be determined using the dataset of observed data points. The density function may represent a statistical model of the observed dataset. In some embodiments, the density function used to determine the probability of any given data point in the feature space being observed in the dataset. In some embodiments, density function may be estimated using a density estimation technique such as a Kernel Density Estimator with Gaussian kernels. However, as will be appreciated by those skilled in the art, other types of density estimators with different guarantees may also be used.

As shown in this example, three contours of the density function are shown: a contour with 95% probability of observation, a contour with 80% probability of observation, and contour with 20% probability of observation. These contours (which may be surfaces in n-dimensional space) represent the shape of a density function in the feature space. As shown, the contours divide the feature space 1000 into regions 1010a-d.

In some embodiments, the synthetic data point generation process will generate synthetic data points (e.g. data points 1050, 1052, 1054, 1055, 1056, 1057, and 1058 in grey) by sampling and varying the observed data points. In this example, observed data point 1020a is selected to generate synthetic data points. However, the illustrated process may be repeated for many observed data points 1020 in the observed dataset. In some embodiments, the observed data points used to generate synthetic data points may be selected at random. In some embodiments, the observed data points may be selected based on one or more selection criteria, such as how far they are from the center of the observed dataset, their respective categories, or their respective feature values.

As shown, to generate synthetic data points, a number of different directions (e.g. directions 1030a-c) are selected from the observed data point 1020a. In some embodiment, a direction may be represented as a unit vector selected from the hypersphere around the observed data point 1020a. In some embodiments, a direction may be based on a selected feature in the feature vector of the data point. In some embodiments, the direction 1030 may be a linear combination of multiple features in the feature vector. In some embodiments, the directions 1030a-c may be selected at random. In some embodiments, the directions may be selected based on the location of the observed data point in the feature space (e.g. relative to the center of the observed dataset), the density function probability of the observed data point, or based on configuration settings (e.g. limiting the synthetic data generation to varying only particular features).

In some embodiments, for each selected direction 1030a-c, a number of candidate synthetic data points are generated in that direction at different distances (e.g. distance 1040 for synthetic data point 1050). As shown, based on the direction 1030a and the distance 1040, the synthetic data point 1050 is generated from the observed data point 1020a. In some embodiments, the different distances for generating synthetic data points in a particular direction may be determined at random. In some embodiments, the distances in a particular direction may be constrained to fall within a specified range. In some embodiments, the process may generate a number of successive synthetic data points with increasing distances (e.g. successive data points 1050, 1052, and 1054) until the probability of the last generated data point falls within a specific interval or below a specified threshold. The threshold may be a configured parameter that prevents synthetic data points from being generated in regions of the feature space that are too far away from the real data.

In some embodiments, instead of selecting a direction first and then the distance for a synthetic data point, the process may first select the distance and then the direction. For example, in some embodiments, the process may select a particular distance, and then generate synthetic data points in multiple directions at the particular distance. In some embodiments, the process may employ both methods (direction-first and magnitude-first) to generate synthetic data points.

As shown, in this example, three synthetic data points 1050, 1052, and 1054 are generated in direction 1030a. Synthetic data points 1050 and 1052 are accepted, while synthetic data point 1054 is not accepted and discarded. In some embodiments, the process may generate each synthetic data point as a candidate, and then check the candidate data point against an acceptance criterion to determine whether the candidate data point should be retained (e.g. added to a dataset for machine learning applications). The acceptance criterion may be based on the density function determined for the observed dataset. For example, the acceptance criterion may accept a candidate data point if the data point is within an acceptable range of probability values indicated by the density function. Data point 1054 may be discarded because it is outside such an acceptable range, which means that the data point is too dissimilar from the observed data points.

Depending on the embodiment, generated synthetic data points may be discarded for a variety of reasons. In some embodiments, a candidate data point may be discarded if its probability of observation based on the density function is too high. In some embodiments, a candidate data point may be discarded if it is too close to other synthetic data points in the feature space. In some embodiments, a candidate data point may be discard if there are already a sufficient number of synthetic data points generated in a similarity group of the candidate point. In some embodiments, candidate data points may be discarded in a random fashion. For example, in some embodiments, a random value between 0 and 1 may be generated for each candidate point. If the random value is above the density function probability of the candidate data point, it is retained. If the random value is below the density function probability of the candidate data point, it is discarded. This technique adds some randomness to the synthetic data generation process, while preferring data points that are closer and more similar to the observed data points.

In some embodiments, the synthetic data generation process may involve a pre-selection of a range of distance values to use for generating synthetic data points, which may be implemented as follows. Consider an observed dataset $X \in \mathcal{M}(n,d)$ where $d \in \mathbb{N}^*$. An observed data point u is bootstrapped from dataset X. A synthetic data point is generated using a direction w for randomly selected from the d-dimensional hypersphere of radius 1 and a distance $\rho$. The assumption is that there exists a density function $\psi$ that dataset X was sampled from. Using a density estimation algorithm, this density may be estimated by $\hat{\psi}$. The density function probability of the resulting synthetic data point may be expressed as the random variable $\hat{\psi}(u+\rho \cdot w)$. A value $d(\rho)$ may then be defined as the expected value of this random variable:

$$d(\rho) = \mathbb{E}\left(\hat{\psi}(u+\rho \cdot w)\right)$$

Because $d(\rho)$ is a continuous function of $\rho$, there exist distances $\rho_1$ and $\rho_2$ such that $d(\rho_1) = \delta_1$ and $d(\rho_2) = \delta_2$. The distance values $\beta_1$ and $\beta_2$ may be estimated through an iterative dichotomy process. With the distance range determined, the synthetic data point generation process may then generate synthetic data points within the distance range of $[\rho_1, \rho_2]$. In some embodiments, the probabilities $\delta_1$ and $\delta_2$ may be specified as configuration information, so that the user can explicitly control how similar or dissimilar the generated synthetic data is to the actual observation data.

Figure 11A:
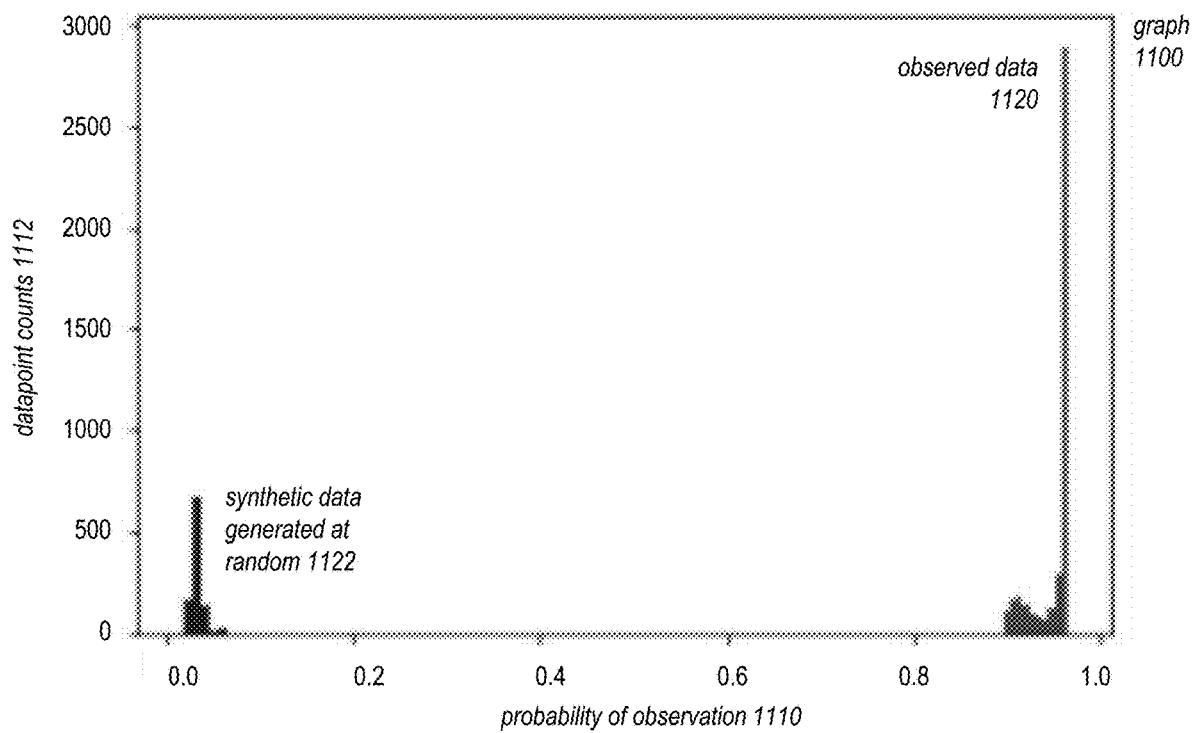
FIG. 11A is a histogram 1100 is a showing the probability of observing real data versus synthetic data regenerated uniformly at random, according to a density function of the real data generated by a machine learning anomaly detection system, according to some embodiments.
Figure 11B:
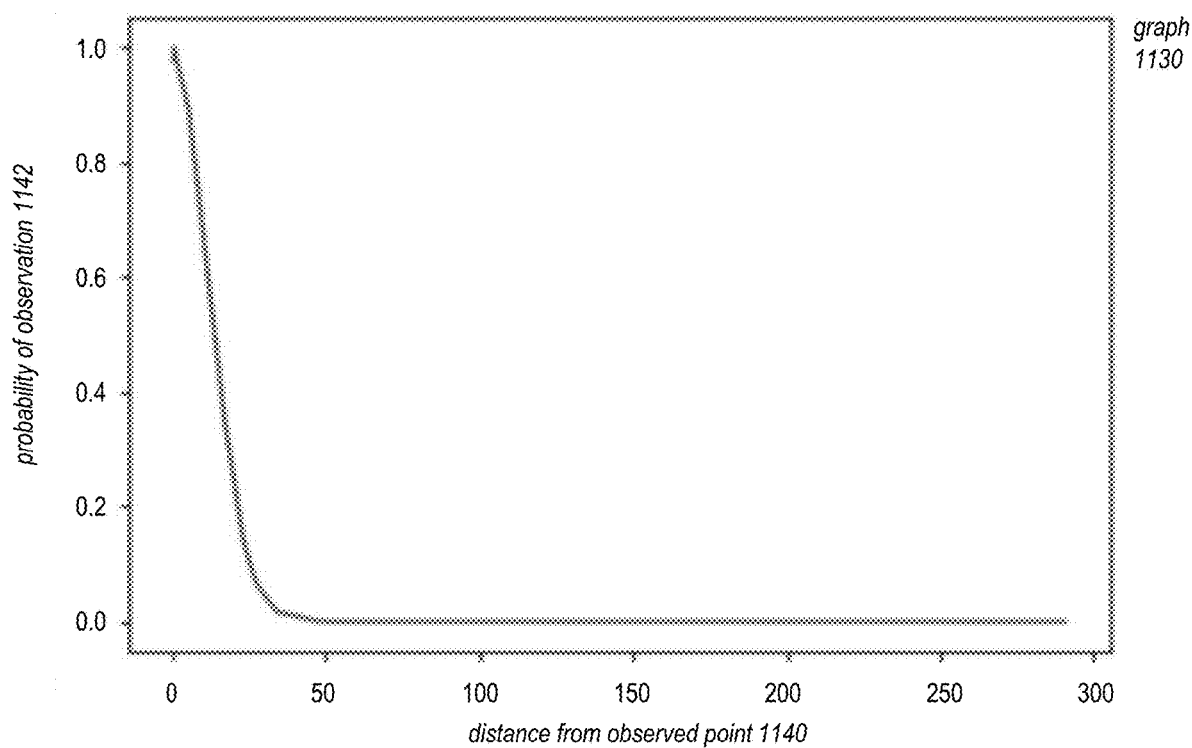
FIG. 11B is a graph 1130 showing the relationship between a distance from an observed data point and the density function probability of a synthetic data point at that distance, according to some embodiments.

In some embodiments, the process may randomly sample $\rho$ from the distance range to create enough data to perform a linear regression between $\rho$ and $d(\rho)$, as shown in FIG. 11B. As shown in graph 1130, the relationship between the distance 1140 and the density function probability 1142 may be non-linear. In some embodiments, the determined relationship between the distance 1140 and the density function probability 1142 may be used to generate successive synthetic data points in a particular direction with increasing distances, in such a way that the successive data points are spaced to have uniformly decreasing density function probabilities.

In some embodiments, the probabilities $\delta_1$ and $\delta_2$ may be obtained from two different density functions. For example, in some embodiments, probability value $\delta_1$ may be obtained from the density function of the observed dataset. Additionally, the system may randomly generate a dataset of synthetic data points that is uniformly distributed across the feature space (or some selected region of the feature space). Probability value $\delta_2$ may be obtained from a second density function that is estimated from the dataset of random synthetic data points. In this way, the user can constrain the synthetic data points using two probability values from the two different density functions, for example, so that all generated data points have greater than the 5th percentile of the probability of being observed in the real dataset according to the first density function and less than a 95th percentile of the probability of being observed in the random dataset.

As may be appreciated by those skilled in the art, the above process may be repeated for many different observed data points, in many different directions, and using many different distances to quickly generate a large population of synthetic data points. Synthetic data points generated in this way tend to be much closer to the actual observed data in the feature space, making these data points more useful for machine learning applications.

FIG. 11A shows a histogram 1100 of data point counts 1112 at different probability values 1110 of the density function w. As shown, the probability values of the actually observed data points 1120 is high and very far away from the probability values of the synthetic data points generated at random 1122. This means that the synthetic data points are dissimilar from the observed data points, and not very good data points for training or evaluating machine learning models for detecting outliers for future observed datasets. It would be more useful to generate synthetic data in the vicinity of the real observed data, where the density function is starting to decrease (e.g. near the frontiers of the observed data 1120).

Figure 11C:
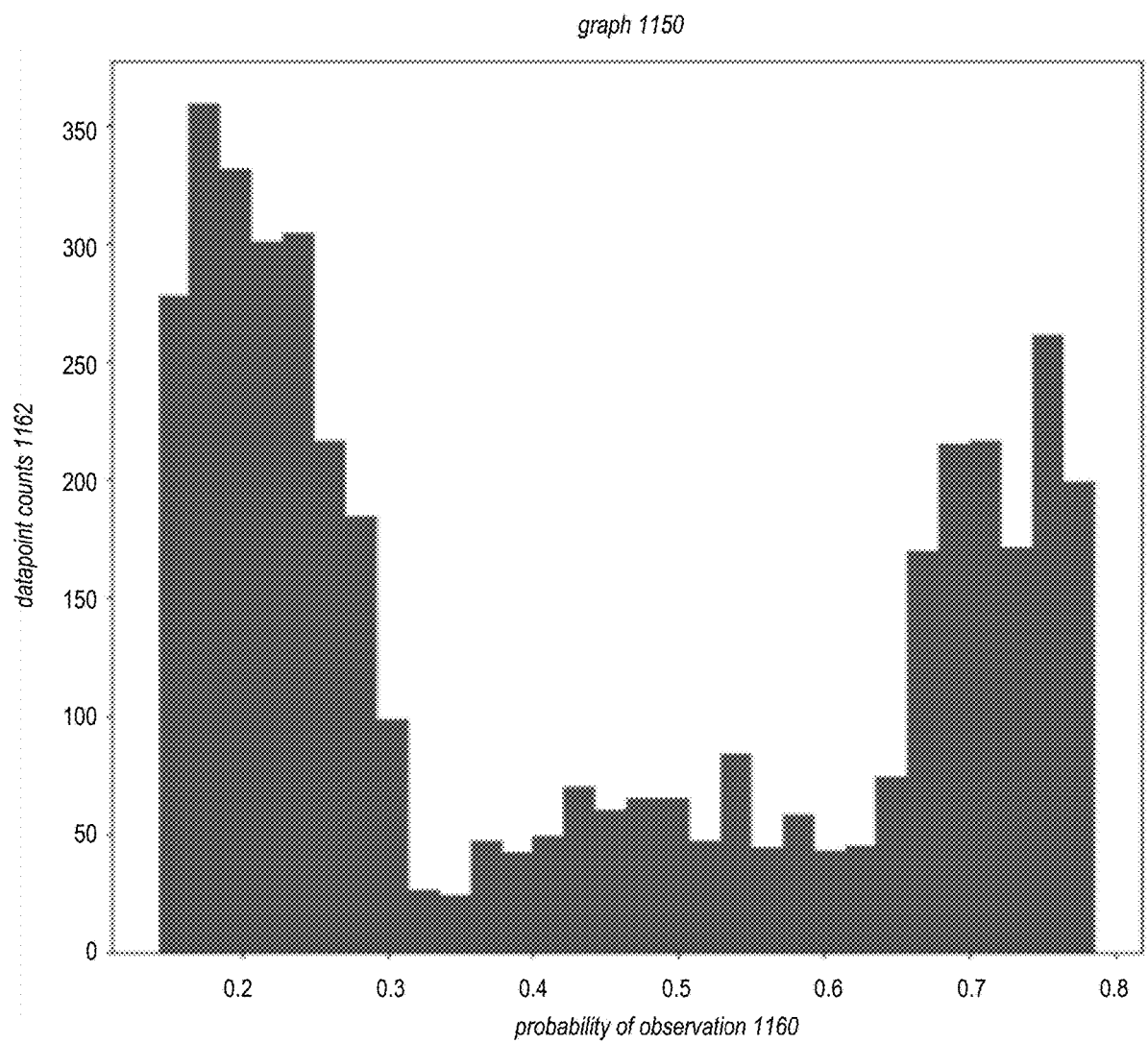
FIG. 11C is a histogram 1150 of the probability of observing synthetic data generated by a synthetic data generation system, according to some embodiments.

FIG. 11C shows another histogram 1150 of data point counts 1162 at different density function probability values 1160, this time for synthetic data points generated using the above-described density estimation technique. As shown in this histogram, the generated synthetic data points are closer to the actual data points in terms of the density function probability, with some generated data points in the 70% range. Moreover, as shown, the generation process may be controlled so that no synthetic data points are generated below 10% probability.

Figure 11D:
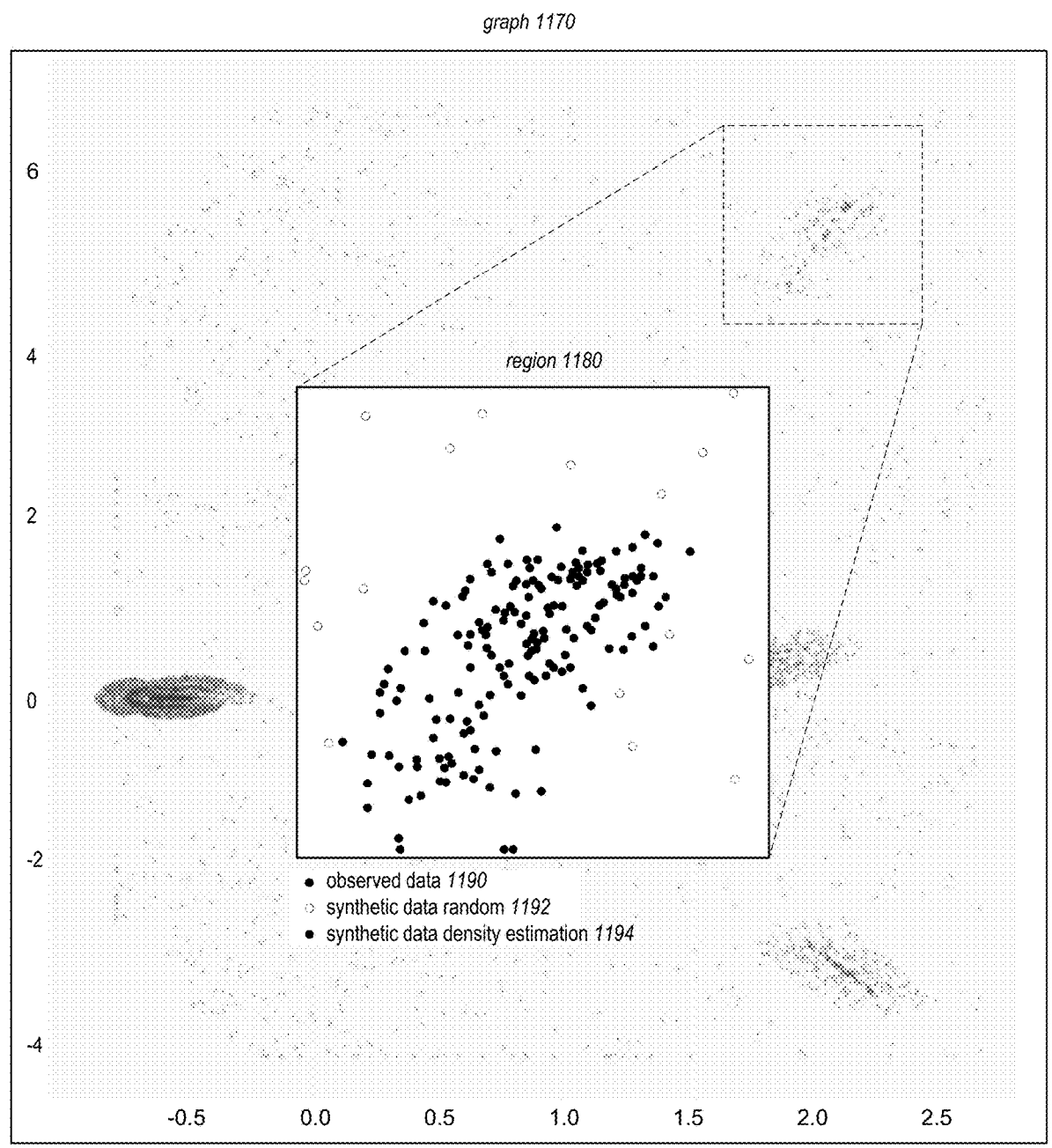
FIG. 11D is a graph 1170 showing a plot of real data in an observed dataset, synthetic data generated uniformly at random, and synthetic data generated using a density estimation scheme by a synthetic data generation system, according to some embodiments.

FIG. 11D shows a plot 1170 of a feature space with real data points of an observed dataset 1190, synthetic data points generated uniformly at random 1192, and synthetic data generated using the above-described density estimation scheme 1194. As shown, the feature space here is projected into two dimensions, which may be the first two dimensions determined by a PCA technique. As shown, the plot zooms in on a region 1180 of the feature space so that the relative locations of the data points may be easily examined. As shown in region 1180, the synthetic data generated using density estimation lie much closer to the observed data, making these data points better training or testing cases for downstream machine learning models.

5. Model Testing Framework Using Automatically Generated Test Datasets

In certain embodiments, given the lack of labeled data, the anomaly detection system or pipeline is configured to evaluate its models by automatically generating synthetic test data for model testing (e.g. testing data 950 of FIG. 9). The test datasets may be generated whenever they are needed by the pipeline, when a new or existing anomaly detection model needs to be tested. For example, embodiments of the anomaly detection pipeline may periodically test its models to determine when a model should be promoted to a working model set of the pipeline, or demoted out of the working set to be observed offline. In some embodiments, the results of the testing may be used to calibrate the models. For example, a precision or recall metric determined for a model for different types of anomalies may be used to adjust a valid range of anomaly scores of the model that correspond to acceptable values of the precision or recall metric. If the anomaly score output by a model falls outside the valid range, in some embodiments, the score may be simply ignored. In some embodiments, the test datasets may be generated in a fully automated fashion as part of the model testing, without the need for any human intervention. In particular, the test dataset generation process does not require manual labeling of the generated observation records, thereby vastly reducing the amount of human labor required to manage the ongoing operations of the pipeline.

5.1 Generating Test Scenarios

In some embodiments, the anomaly detection system or pipeline is configured to generate individual test datasets to represent different types or scenarios that mimic possible real life anomalous behaviors of the observed machines. In some embodiments, the anomaly detection system may use similar processes to generate the same types of scenarios for training the models. A model may be trained using a training dataset that contains the same distributions of anomalous data as in the test dataset. The following provides a list of the example scenarios that may be generated by the anomaly detection system for model training or testing.

5.1.1 Scenario 1: Single Feature Anomaly

Figure 12:
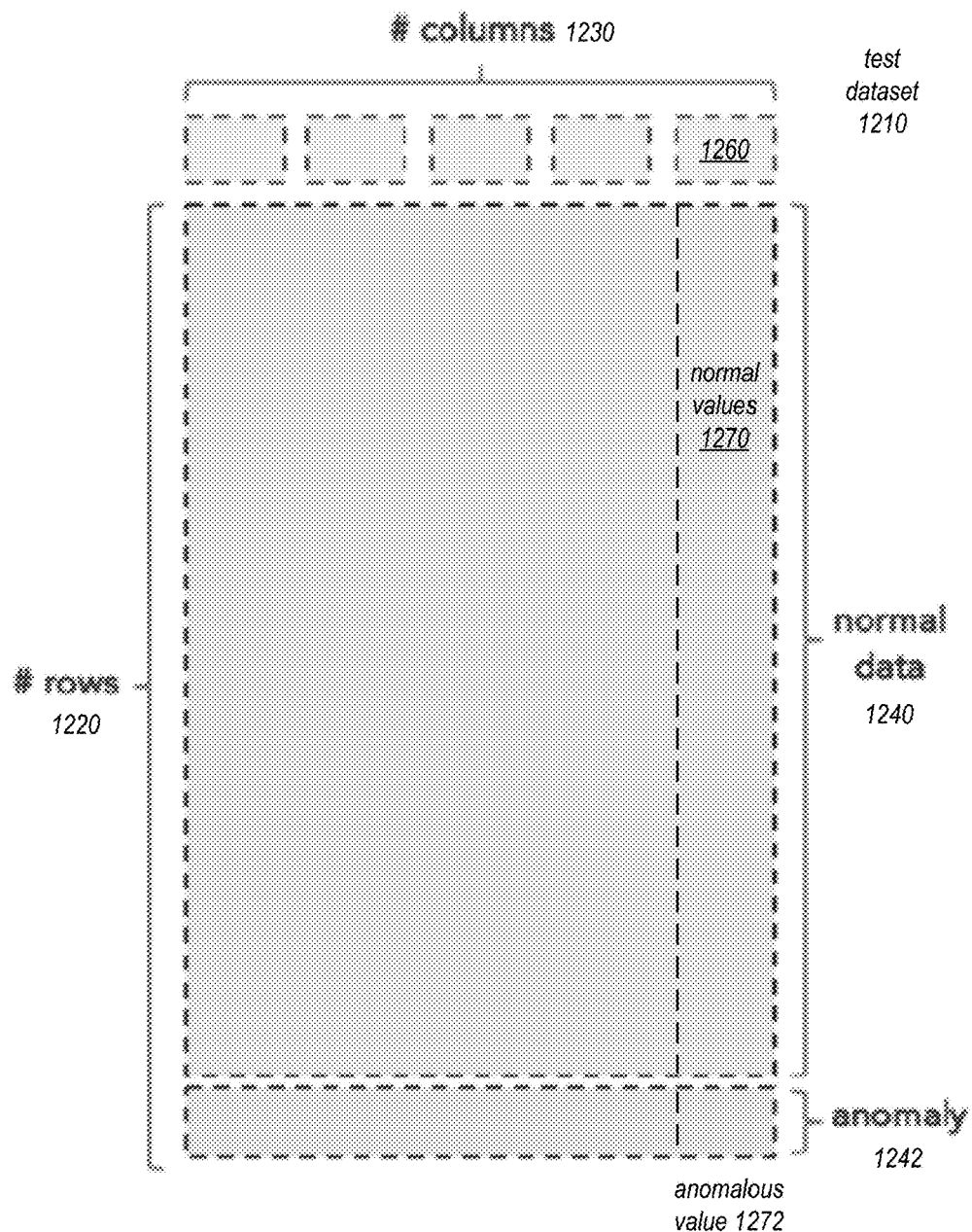
FIG. 12 is a block diagram 1200 of a first scenario of using synthetic data to evaluate models in a machine learning anomaly detection system, according to some embodiments.

FIG. 12 is a block diagram 1200 of a first scenario of using synthetic data to evaluate models in a machine learning anomaly detection system, according to some embodiments.

In this first scenario (Scenario 1), a test dataset 1210 is generated with n rows of observation records 1220 and k columns of features 1230. Thus, the dataset 1210 may be represented as a matrix where each cell of the matrix represents a particular feature value of a particular observation. In some embodiments, the test dataset may be encoded as matrix 200 or 230 as discussed in connection with FIG. 2A or 2B. Depending on the embodiment, the feature values may be binary values (e.g. 0 or 1), a set of discrete values, or continuous values.

As shown, in Scenario 1, the generated dataset 1210 contains a number of observations of normal data 1240, and at least one observation of an anomaly 1242. To generate the anomalous record, a particular feature 1260 is selected from among the k features of the dataset. The normal observation records are generated with normal values 1270 for the selected feature 1260, and the anomalous record (s) are generated with an anomalous value 1272 for the feature 1260.

Depending on the embodiments, the feature 1260 and/or the feature values 1270 and 1272 may be selected in a variety of ways. For example, in some embodiments, the feature 1260 may be selected based on a specified selection criterion, such as the feature variability metric discussed in connection with FIG. 5 or FIG. 6. In some embodiments, the feature values 1270 and 1272 may be selected based on an analysis of historical observation record values, which may be stored by the anomaly detection system. The normal values 1270 may be one or more commonly-seen values in the historical observations (e.g. for a recent time window). The anomalous value(s) 1242 may be one or more rarely-seen (or never-seen) values in the historical data. In some embodiments, the values 1270 and 1272 may be selected in a random fashion, so that the test data generation process is completely deterministic over multiple runs.

As shown in the depicted example, the observation records 1220 are bit vectors where each bit represents a feature 1230. In this example, the normal records 1240 contain a normal value for the selected feature bit 1260, while the anomaly record 1242 contains an anomalous value for the selected feature bit. More formally, in a generated test dataset where n is the number of observations and k is the number of features, a pattern of observation records may be created in the form $e_i=(0, \ldots 0, 1, 0, \ldots, 0)$. In some embodiments, the pattern may be generated in the canonical base of $\mathbb{R}^k$. A group $X_i$ of observation records may then be generated from the particular pattern.

In some embodiments, multiple pattern groups $X_i$ may be created with respective sizes or record counts $h_i$ such that $$\sum_{i=1}^{k-1} h_i = n-1 \text{ and } h_i > \min(0.01*n, 100).$$

The entire test dataset may then be generated using the multiple pattern groups.

In some embodiments where the observation records are bit vectors, each row may contain only one bit set to the value of 1, while the rest of the columns or features are set to value 0. In some embodiments, the anomaly record 1242 will be generated such that all columns except the last column are 0s. In some embodiments, the observation records 1220, the features 1230, or both, may be randomly shuffled to produce the ultimate test dataset 1210.

In some embodiments, the observation records 1220 may be constructed from actual historical records. For example, the normal observation records 1240 may be created based on samples retrieved from a historical records repository (e.g. commonly-observed or randomly selected records). Similarly, the anomaly record 1242 may be based on the same or similarly sampled records from the historical records repository. The sampled records may be modified to manipulate the selected feature 1260 according to the requirements of the test dataset.

In some embodiments, Scenario 1 may be used to test whether or not the machine learning models can identify anomalies in an idealized context, where an anomalous observation record contains one feature that is not present in the other observation records. Depending on the embodiment, various aspects of the test dataset generation process for this scenario can be configurable via a configuration interface of the anomaly detection system. For example, the anomaly detection system may permit users to specify settings that control how the feature 1260 is selected, how the normal value(s) 1270 and anomalous value(s) 1272 are selected, particular value ranges for the number of features (k) and number of records (n), among other types of configuration settings.

5.1.2 Scenario 2: Anomalous Pattern of Multiple Features

Figure 13:
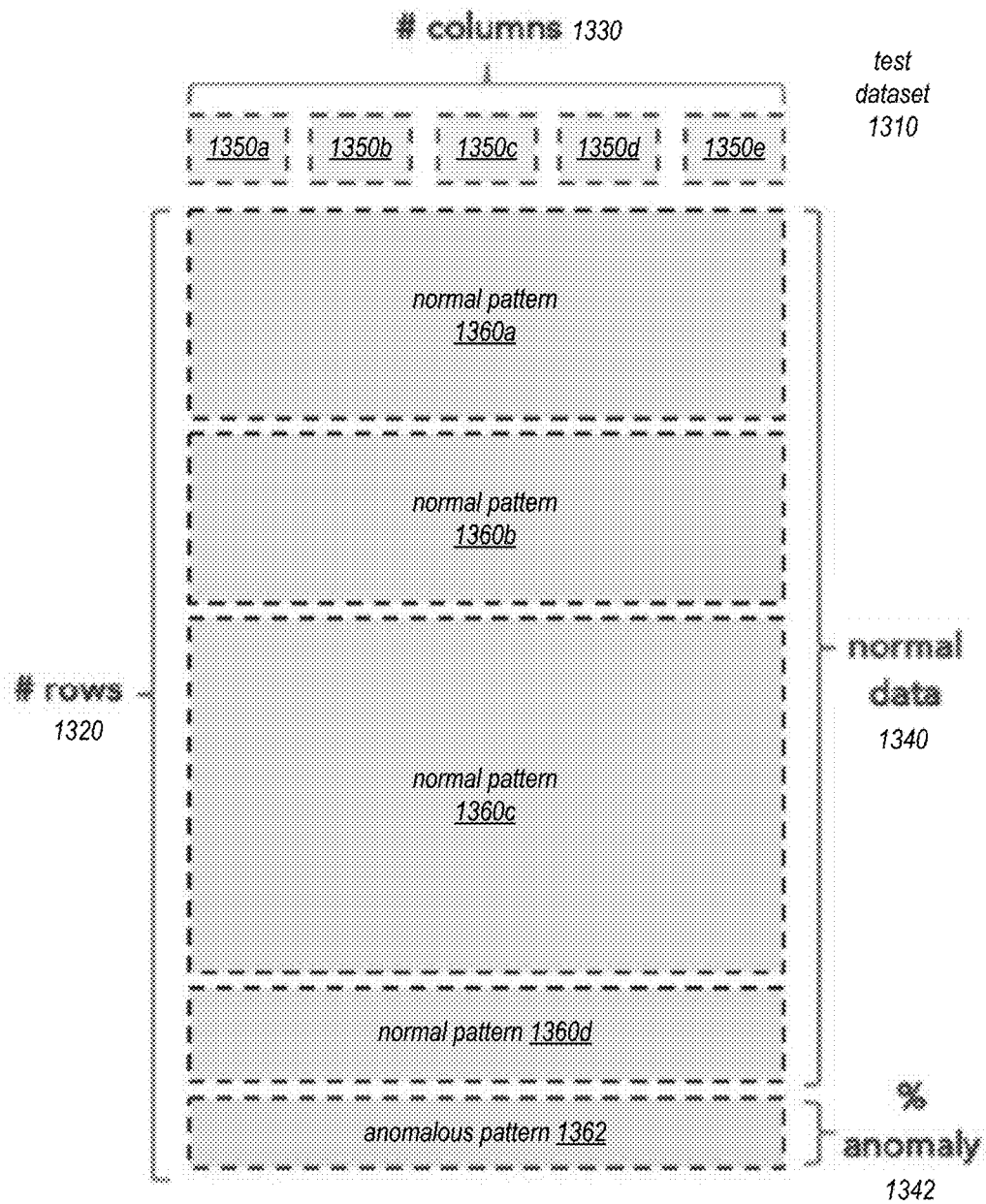
FIG. 13 is a block diagram 1300 of a second scenario of using synthetic data to evaluate models in a machine learning anomaly detection system, according to some embodiments.

FIG. 13 is a block diagram 1300 of a second scenario of using synthetic data to evaluate models in a machine learning anomaly detection system, according to some embodiments.

Similar to test dataset 1210, the generated test dataset 1310 in this example contains n rows 1320 of observation records and k columns 1330 of features. Scenario 2 increases the complexity of Scenario 1 by allowing anomaly observation record (s) to include a combination of multiple features. For example, if the observation records include types of processes observed on individual machines, the anomaly record may contain a particular combination of process types that are not indicated in the normal observation records. As another example, the anomaly record may indicate the presence of a same type of process as seen in the normal records, but with a different (anomalous) set of observed process properties.

As shown in this example, five columns of features 1350*a-e* are included in the observation records. Different value combinations of these five features 1350*a-e* represent different feature patterns. In this example, four such feature patterns are chosen as normal patterns 1360*a-d* in the dataset, and one pattern is used as an anomalous pattern 1362. As shown, for each normal pattern 1360*a-d*, a group of normal observation records 1340 are generated. Likewise, for the group of anomalous records 1342 are generated for the anomalous pattern 1362. In some embodiments, the test dataset 1310 may include multiple anomalous patterns.

Similar to Scenario 1, the normal patterns 1360 and anomaly pattern(s) 1362 in Scenario 2 may be selected based on an analysis of historical observation data. For example, the normal patterns may be sampled from previous patterns that were frequently encountered in the historical data, while the anomaly pattern may be a pattern that was rarely seen or not seen in the historical data. In some embodiments, the relative counts or proportions of each group of records in the dataset is determined based on the relative frequency of their patterns in the historical data. For example, a more common feature pattern may be represented by a larger record group in the test dataset. In some embodiments, the patterns and/or pattern group sizes may be selected in a random fashion.

In embodiments where the observation records are bit vectors, the generated test dataset 1310 may contain patterns where multiple features bits are non-zero. In some embodiments, a fixed set of bit patterns ($p_1, \ldots, p_m$), $m \geq 1$ are selected such that:

$$\mathbb{P}(p[i] = 1) = \frac{1}{s/i^3}$$

where $$s = \sum_i \frac{1}{i^3}.$$

However, it is noted that in other embodiments, a different probability function may be used. For example, the process will generate patterns according to the probability above. That is, for each position i of a pattern, the process will set the position to a one with probability $$\frac{1}{s/i^3}.$$

Generated patterns are added to a list. If a new pattern is already in the list, it is discarded. When all the m patterns have been generated, the test set matrix is created with frequencies $h_1, \ldots, h_m$ for each pattern.to produce the normal observation records 1340 in the test dataset 1310. In some embodiments, the columns in test dataset 1310 may be shuffled, so that the positions of features that are the most shared among the records are randomized.

Finally, a number or proportion of anomaly records 1342 containing an anomalous pattern a is generated (e.g. as a chosen percentage of the total number of records n). In some embodiments, the anomalous pattern 1362 may be selected from historical records. In some embodiments, the anomalous pattern 1362 may be generated by modifying one or more normal patterns, for example, using the synthetic data point technique discussed in connection with FIG. 10.

In some embodiments, a distance metric $\delta$ may be calculated to quantify the difference from between the anomaly pattern a and the normal patterns p:

$$\delta = \min(\|a - p_1\|_1, \ldots, \|a - p_m\|_1)$$

In some embodiments, this distance metric $\delta$ may be a configurable sensitivity parameter used to control the type of anomalous pattern that is injected into the test dataset 1310. A higher value of $\delta$ will allow a more anomalous pattern to be added to the test dataset 1310. Accordingly, Scenario 2 may be used to test the sensitivity of an anomaly detection model to identify anomalies of varying degrees of anomalousness.

In some embodiments, the distance metric $\delta$ may be used to determine the number or proportion of anomaly records 1342 of that pattern a in the test dataset 1310. For example, more rows of anomalous records may be generated for the anomaly pattern based on how close the pattern is to a normal pattern. In this manner, the generated dataset 1310 will reflect a more realistic picture of the actual data.

As with Scenario 1, the anomaly detection system may allow various aspects of the test data generation process for this scenario to be configured. For example, a configuration interface may be provided allow a user specify how many normal or anomalous pattern groups to generate, the number of features to use to create the patterns, how the sizes of each pattern group are determined, how the pattern features and/or pattern values are selected, etc., among other types of configurable settings.

5.1.3 Scenario 3: Injection of Noise

Figure 14:
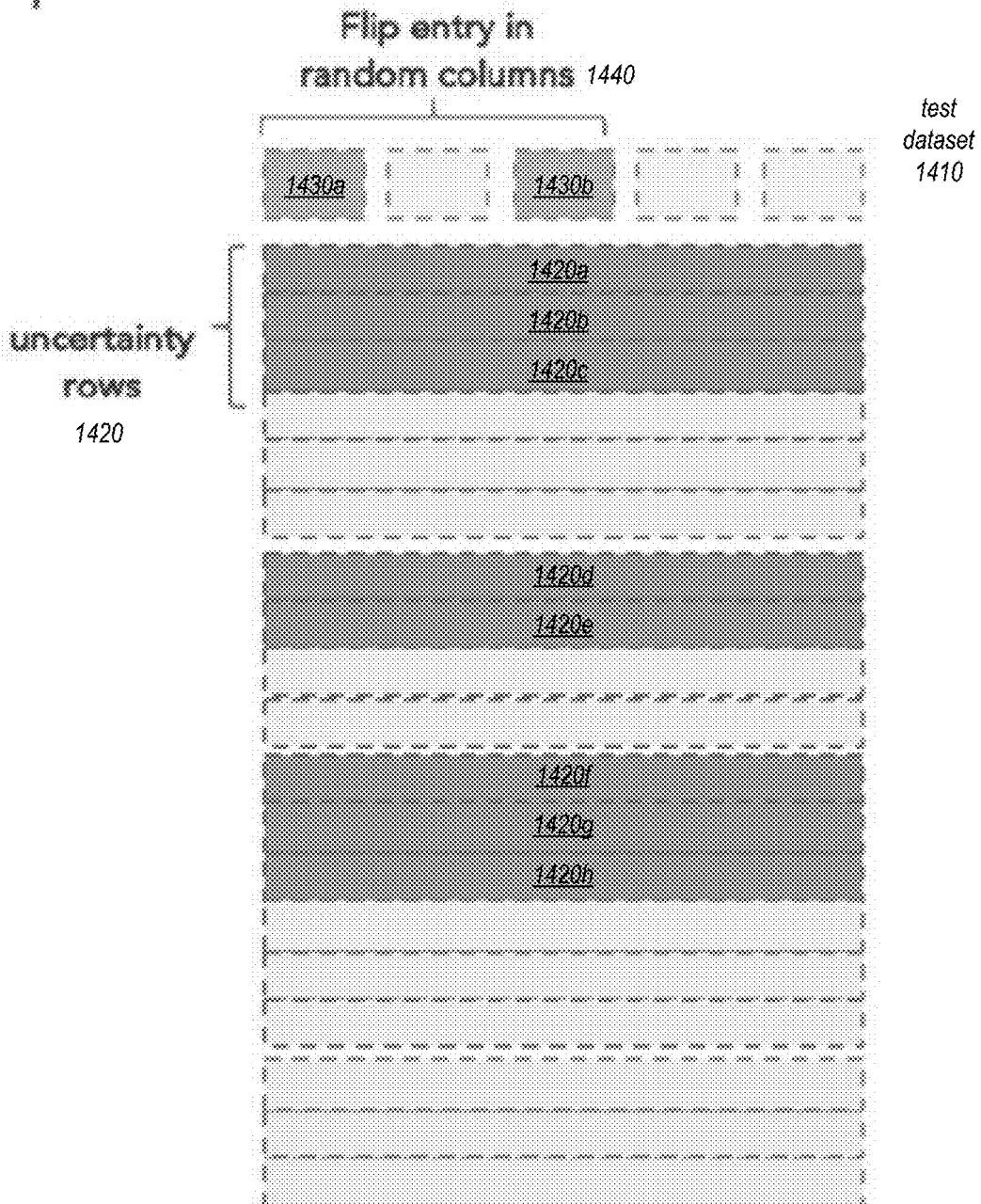
FIG. 14 is a block diagram 1400 of a third scenario of using synthetic data to evaluate models in a machine learning anomaly detection system, according to some embodiments.

FIG. 14 is a block diagram 1400 of a third scenario of using synthetic data to evaluate models in a machine learning anomaly detection system, according to some embodiments.

In some embodiments, Scenario 3 builds on the test data generation process of Scenario 2 to inject a level of random noise or uncertainty into the test dataset 1410. The injected noise may be used to test the robustness of the anomaly detection models to distinguish true anomalies from the noise.

Depending on the embodiment, the random noise may be injected in a number of ways. As shown in this example, the injection process may first select a number or proportion of uncertainty rows or records 1420*a-h* for noise injection. The process may then select a subset of features within the generated patterns of each uncertainty record (features 1430*a* and 1430*b* in this example) to be modified. In some embodiments, a different set of features 1430 may be modified for each uncertainty record 1420. In some embodiments, the uncertainty records 1420 and the modified features 1430 may be selected randomly. In some embodiments, the uncertainty records 1420 and modified features

1430 may be selected based on a statistical analysis of historic observation data. For example, the modified features 1430 may be selected based on lower values of the feature variability metric, as discussed in connection with FIGS. 5 and 6.

In embodiments where the observation records are bit vectors, as in the illustrated example, the injection of noise may involve flipping 1440 selected feature bits (e.g. from 0 to 1 or vice versa) within generated patterns. In some embodiments, the new values of the selected features 1430 may be selected randomly. In some embodiments, an uncertainty record may be modified so that the new value of the record is within a distance from the original value in the feature space of the observation records. For example, the new record values may be generated using the synthetic data point generation technique discussed in connection with FIG. 10. In some embodiments, the modified record may be generated so that it does not reduce the probability density value of the original record by more than a specified threshold. In some embodiments, the new record may be generated in a part of the feature space with a higher probability density value than that of the anomaly records.

As with Scenarios 1 and 2, the generation of a Scenario 3 dataset may also be configurable via the configuration interface. For example, in some embodiments, the configuration parameters for this scenario may control how many uncertainty records and features within the uncertainty records to modify, how to select the uncertainty records and/or the features, and how to generate new feature values for the uncertainty records, among other configurable settings.

5.1.4 Scenario 0: No Anomalies

In some embodiments, the testing framework for anomaly detection models may generate a Scenario 0 test dataset, where there are no anomaly records. This test dataset may be generated using similar techniques used to generate the normal observation records for Scenarios 1, 2, and 3, as discussed above. For example, some proportion of records in the test dataset may include a degree of random noise, which may be injected as discussed for Scenarios 3.

In some embodiments, the Scenario 0 test dataset is used to measure the false positive rate of an anomaly detection model in a situation where no anomalous observations exist. The model's detection results for this scenario may be combined with the model's results from other scenarios to obtain an overall model performance result, which may be used to take further actions on the model and/or make dynamic adjustments to the anomaly detection system.

5.2 Scenario-Based Testing Strategies

In some embodiments, after a test dataset (e.g. dataset 1210, 1310, or 1410) is generated, the testing framework may submit the dataset to an anomaly detection model to obtain an anomaly detection result from the model. The testing framework may then check whether the injected anomaly record is detected by the model. For example, the testing system may check whether the anomaly record is among the list of highest ranking anomalies identified by the model, or whether an outlier metric of the anomaly record determined by the model meets a specified threshold. Based on the model's detection result, the testing system may assign a pass or fail grade (or an accuracy score) to the model for the particular scenario. In some embodiments, the testing process of a model is fully automated, so that it can be performed without any human involvement. In particular, the testing process does not require human analysts to manually label observation records used in the test dataset.

In some embodiments, each model may be tested using multiple scenarios and generated test datasets, and the performance results of the multiple tests are aggregated to obtain an overall performance result of the model. As will be appreciated by those skilled in the art, different testing strategies may be employed in different embodiments to evaluate the models. As one example, the testing scenarios could be encoded using continuous rather than binary features. Continuous data would allow for more complex analysis of the anomaly detection pipeline, for example, to determine whether the pipeline is able to detect outliers of normal points generated following a multi-dimensional Gaussian, among other types of analysis. Given the foregoing scenarios that can be simulated using synthetic data, a number of model testing strategies can be provided below for more comprehensive testing of the anomaly detection models.

5.2.1 Base Case Analysis

Figure 15:
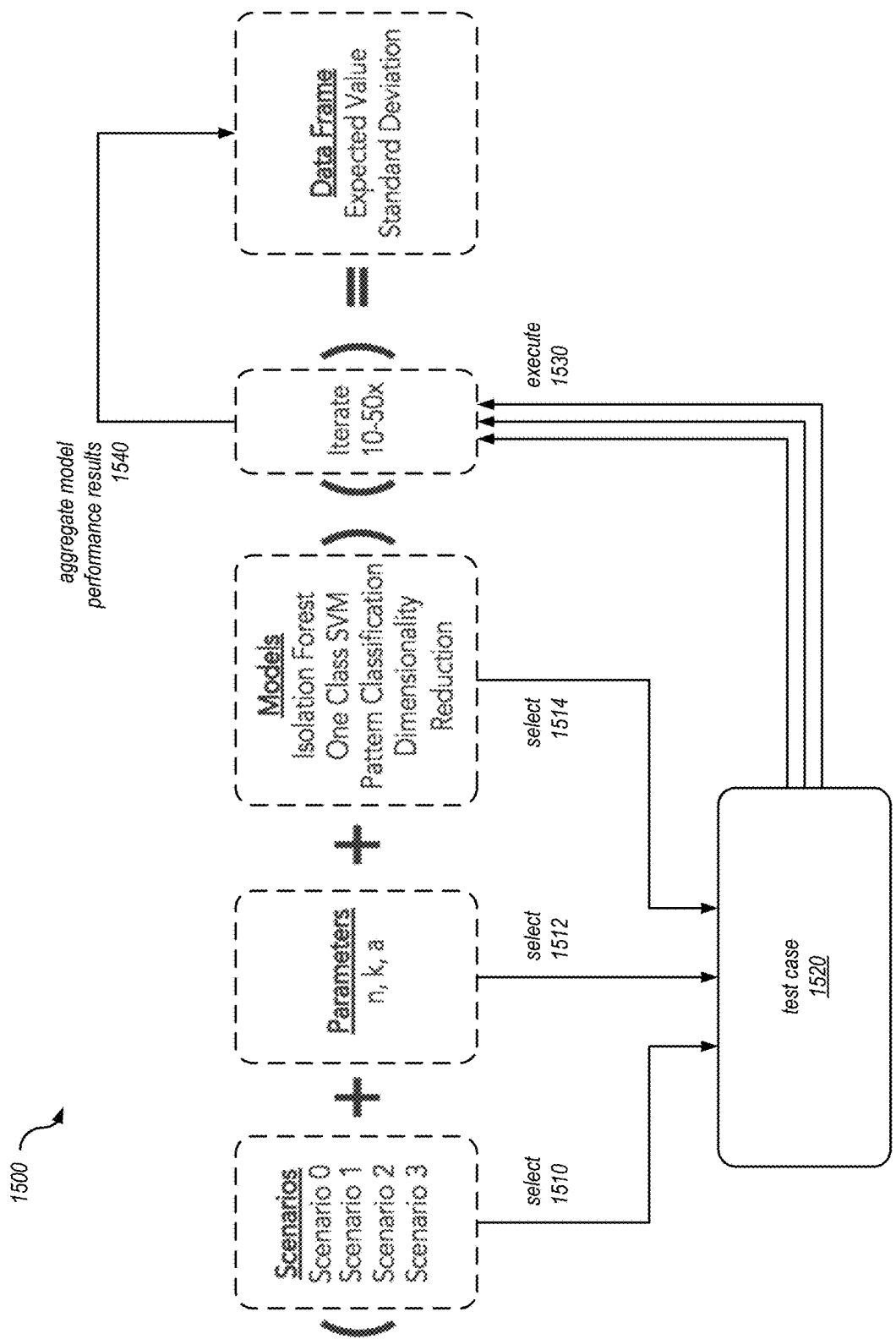
FIG. 15 is an illustration 1500 of a base case analysis performed using synthetic data to evaluate models in a machine learning anomaly detection system, according to some embodiments.

FIG. 15 is an illustration 1500 of a base case analysis performed using synthetic data to evaluate models in a machine learning anomaly detection system, according to some embodiments.

As shown in the figure, the base case analysis involves constructing a series of test cases for individual models to comprehensively analyze how different models perform across different scenarios and across different parameters. As shown in the figure, each test case 1520 will be constructed using a combination of a list test case parameters. In the base case analysis, the scenarios will be isolated from each other (e.g., the scenarios will not be combined with each other in a single test dataset). In some embodiments, the following list of test case parameters may be varied for each test case:

Scenarios
    Scenario 0
    Scenario 1
    Scenario 2
    Scenario 3
Dataset Parameters
    Number of rows (n)
    Number of features (k)
    Number of anomalies (a)
Anomaly Detection Model Type
    Isolation Forest.
    One-Class SVM
    Random Forest
    XGBoost
    SVM
    Logistic Regression
    K Nearest Neighbors As shown, to create a particular test case 1520, one scenario is selected 1510, a specific combination of dataset parameters n, k, and a is selected 1512, and a type of anomaly detection model is selected 1514. In some embodiments, each test case 1520 may be executed many times (e.g. between 10 and 50 iterations). During each run of the test case, a new test dataset may be generated based on the selected parameters. The generated test dataset will then be analyzed by the selected model to obtain an anomaly detection result for that particular test run. This anomaly detection result will be examined by the testing framework to obtain a model performance metric for the model (e.g. an accuracy score, a number of anomalies that were correctly or incorrectly identified, a pass-or-fail indicator, etc.). In some embodiments, the model performance result may be aggregated 1540 over the multiple test runs to extract a data frame that indicates the expected value (E) and standard deviation(s) of the model performance result for that test case.

In some embodiments, the described testing process may be repeated for multiple test cases. Depending on the embodiment, individual test cases may be selected in a randomized fashion, or according to specified configuration settings provided to the testing framework. For example, in some embodiments, a system administrator may define a set of mandatory test cases for individual types of anomaly detection models, and also allow a number of random test cases to be selected by the system. Ultimately, the testing framework may determine an overall performance result for each model using the test case results for that model. In some embodiments, the testing framework may also perform a linear regression analysis for the models to determine how the different testing parameters impact the overall performance of the models. For example, such regression analysis may show that, for a particular model and a particular testing scenario, the model's accuracy will increase with increasing size of the dataset.

5.2.2 Mixed Scenario Analysis

In some embodiments, the testing framework may use a mixed scenario analysis as a model training and testing strategy. In the mixed scenario analysis, a model may be trained or tested with a single dataset generated under different combinations of scenarios and dataset parameters. This contrasts from the datasets generated in the base case analysis, where the scenarios are not mixed in a single dataset.

The mixing of scenarios may be performed in a variety of ways. For example, in some embodiments, a generated test dataset may employ K blocks of observation records, where each block corresponds to a different scenario. The test dataset may be generated randomly, while keeping the number of records n and the number of scenario blocks K fixed. In some embodiments, the K scenario blocks may include at least one of Scenarios 0, 1, 2, or 3 described above. In some embodiments, each scenario block may include zero, one, or multiple anomaly records. In some embodiments, each of the K scenario blocks may be associated with its own dataset parameters, such as the number of variable features k and the percentage of anomaly records p, etc.

In some embodiments, when a mixed-scenario test dataset is analyzed by an anomaly detection model, the model's performance result may indicate a performance variable for each scenario block in the dataset. For example, the performance variable may indicate a 1 if the model correctly detected the anomaly in a given scenario block, and a 0 if the model failed to detect the anomaly. In some embodiments, a linear/logistic regression can be performed over each of the scenario block parameters to provide additional insight into the strengths and weaknesses of a model. For example, a regression analysis may reveal that a particular model performs poorly when the noise level in the data rises above a certain level.

5.2.3 Model Aggregation Analysis

Figure 18:
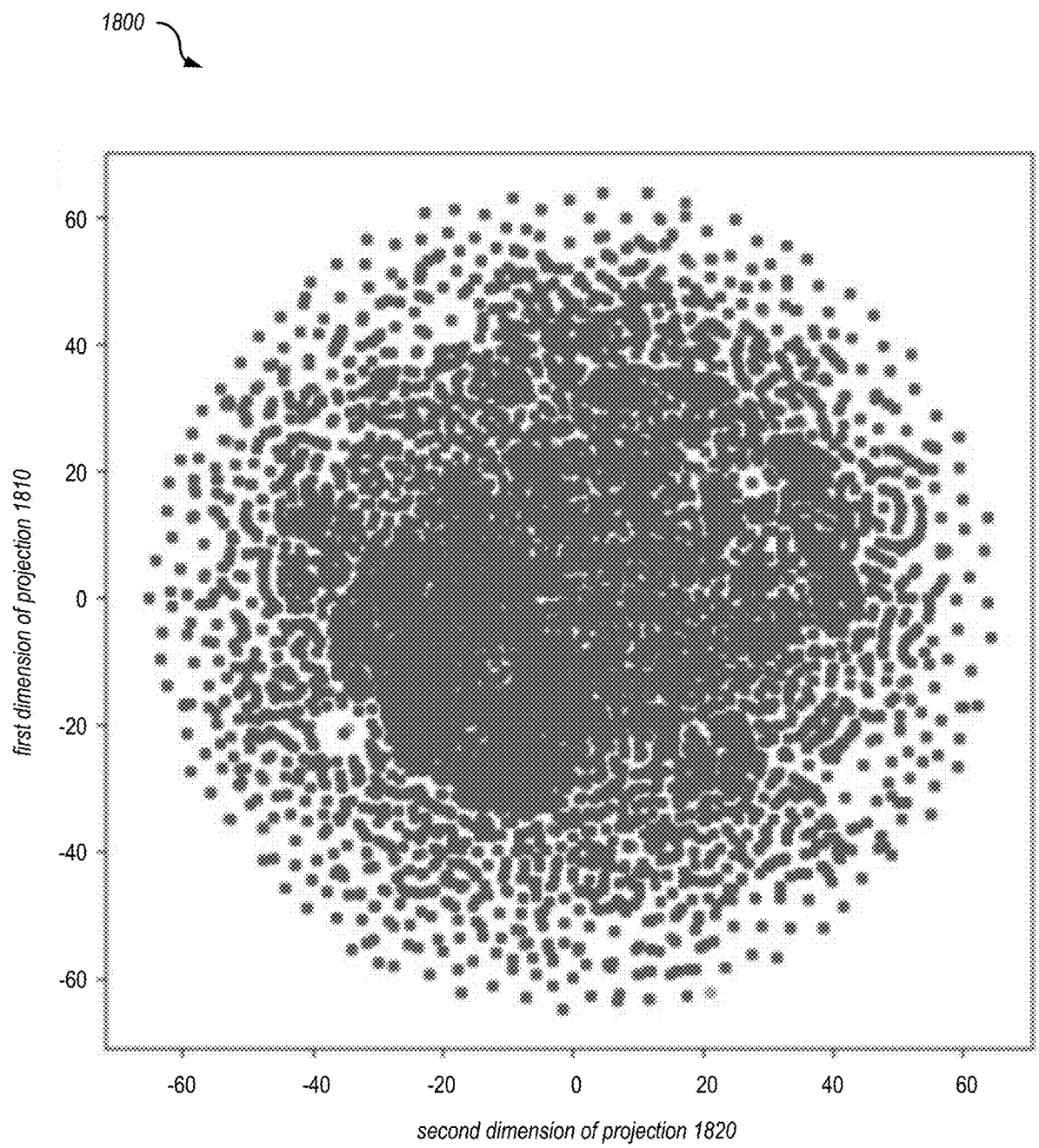
FIG. 18 is a graph 1800 that illustrates a projection of process data points analyzed by a machine learning anomaly detection system, according to some embodiments.

In some embodiments, the testing framework may implement another model testing strategy to perform a model aggregation or ensembled analysis. In the model aggregation analysis, the detection capabilities of multiple models are examined together. For example, FIG. 18 shows the test results of three anomaly detection models 1610, 1620, and 1630 that were tested together using the same set of test cases. The Venn diagram shows the different anomalies that were identified by each model during testing.

In some embodiments, the aggregation analysis may be used to quantify a confidence level of anomaly detection results based on different regions of the Venn diagram. For example, the testing results may show that anomalies in the area 1640 were correctly identified 90% of the time. Based on this result, the anomaly detection system may provide a confidence level of 90% whenever all three models in the ensemble report the same anomaly. Conversely, test results may show that the anomalies identified in area 1650 were correct only 50% of time and include a large number of false positives. Accordingly, the anomaly detection system may associate a low confidence score when only model 1630 identifies an anomaly. In some embodiments, these model aggregation analysis results may be used to dynamically adjust reporting thresholds for the ensemble (e.g. only report a detected anomaly if two of the three models agree on a detected anomaly).

In some embodiments, model aggregation analysis may also be used to provide coverage testing for the ensemble. For example, testing results may show that with three models in the ensemble, the ensemble failed to identify the anomaly in approximately 20% of the test cases. This test result may be used to trigger an automatic action by the anomaly detection system to add additional models to the ensemble, which may be trained to specifically target the missed anomalies. Conversely, if it is determined that the detection capabilities of a particular model are largely redundant to the detection capabilities of other models in the ensemble, the anomaly detection system may automatically remove the particular model from the ensemble to conserve system resources and/or improve model execution performance. In some embodiments, the results of the model aggregation analysis may reveal that some models perform better for certain types of scenarios, while other models do better for other scenarios. Based on this finding, the anomaly detection system may be configured to dynamically choose a group of models to target a desired (or suspected) type of anomaly scenario, or maintain a group of models that has the best all-around performance.

5.2.4 Anomaly Distance Analysis

In some embodiments, the testing framework may implement another model testing strategy that uses an anomaly distance analysis. In an anomaly distance analysis, the distance between an anomaly record and the normal records in a dataset (e.g. the & metric discussed previously) is tracked by the testing framework. The anomaly distance of a test case may be compared to the performance results associated with the test case to allow a human analyst to better understand how the "anomalousness" of anomaly data affects the models' abilities to detect them. For example, for some anomaly detection models, a greater anomaly distance may increase the model's chances of identifying the anomaly. In some embodiments, the distance metric $\delta$ may be an additional parameter that can be configured during the creation of test cases, and an addition parameter that can be separately analyzed during the base case analysis.

5.3 Model Testing Results

Figure 17A:
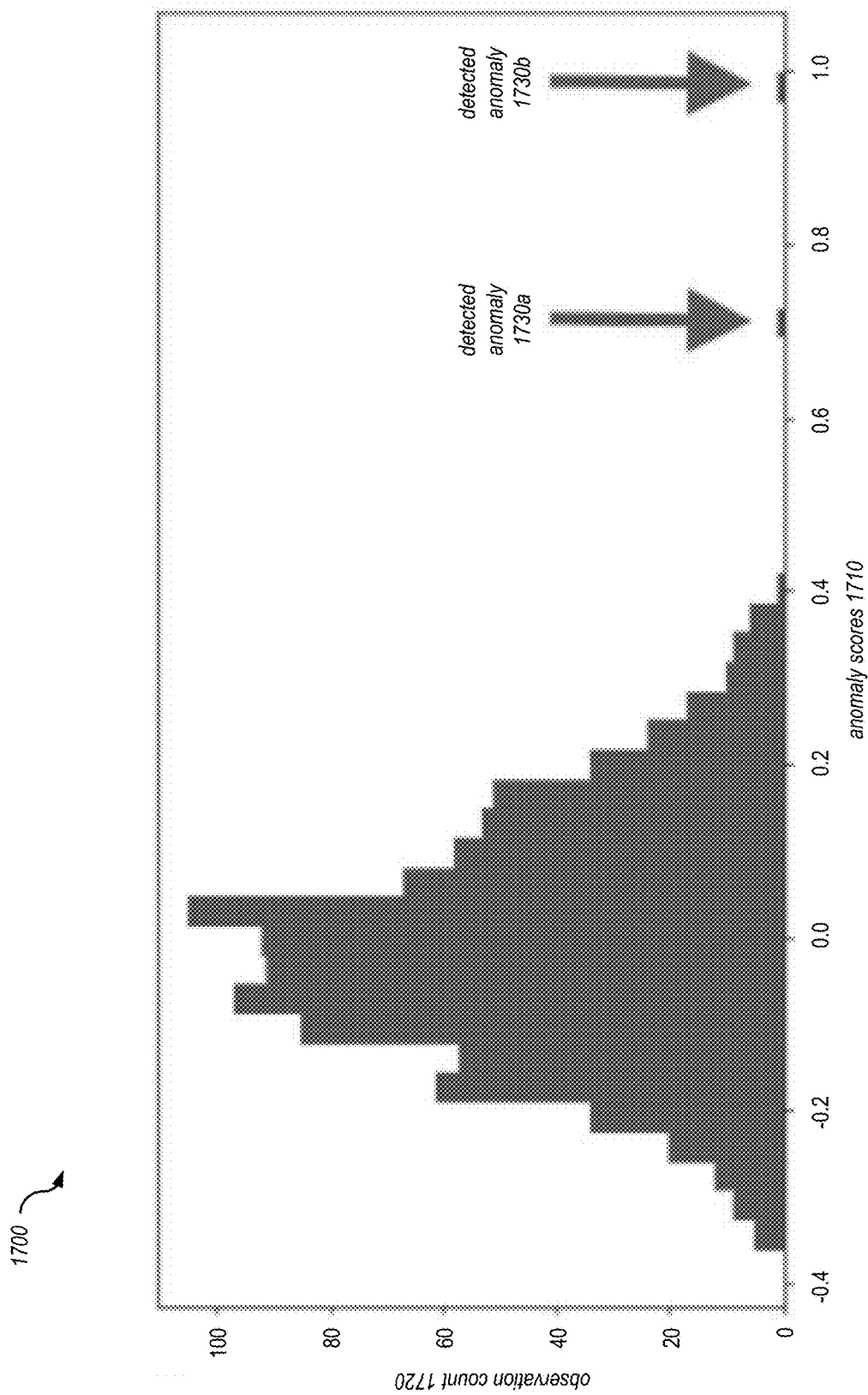
FIG. 17A is a graph 1700 showing two anomalies detected during model evaluation using synthetic data in a machine learning anomaly detection system, according to some embodiments.

In one study involving the base case testing strategy and using Scenario 1, an embodiment of the testing framework was used to generate synthetic datasets for test cases. The test cases were generated across different sample sizes and different number of features (e.g., sample size ranged from [100, 5000] and number of features ranged from [2, 18]). Having generated synthetic data for Scenario 1, it was determined that a significant portion of the models used in the anomaly detection pipeline performed as expected. It should be noted that the foregoing study was performed with uniformly random synthetic data, although other models may improve results in higher dimensions. FIG. 17A illustrates the models' ability to identify outliers determined using the study (n=1000, k=87). As shown, the figure depicts a histogram of anomaly scores, where the x-axis 1710 indicates the normalized anomaly scores for observation records in the test datasets, and the y-axis 1720 indicates an observation count in each score bucket. The two arrows in the histogram indicate two instances of successfully detected anomalies 1730a and 1730b generated by the testing framework.

Figure 17C:
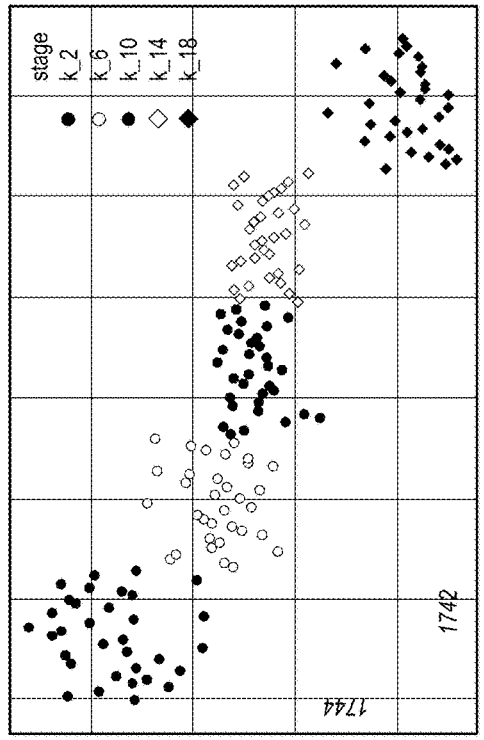
FIG. 17C is a graph 1740 that illustrates anomaly scores from Random Forest as determined during model evaluation using synthetic data, according to some embodiments.
Figure 17B:
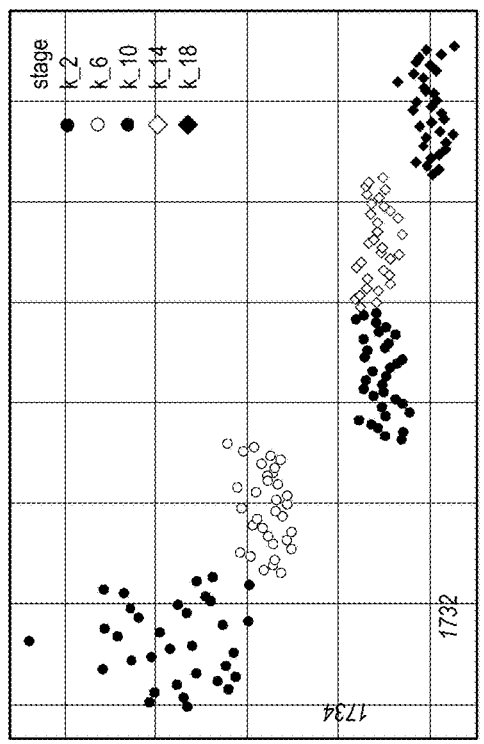
FIG. 17B is a graph 1730 that illustrates anomaly scores for Isolation Forest as determined during model evaluation using synthetic data, according to some embodiments.
Figure 17D:
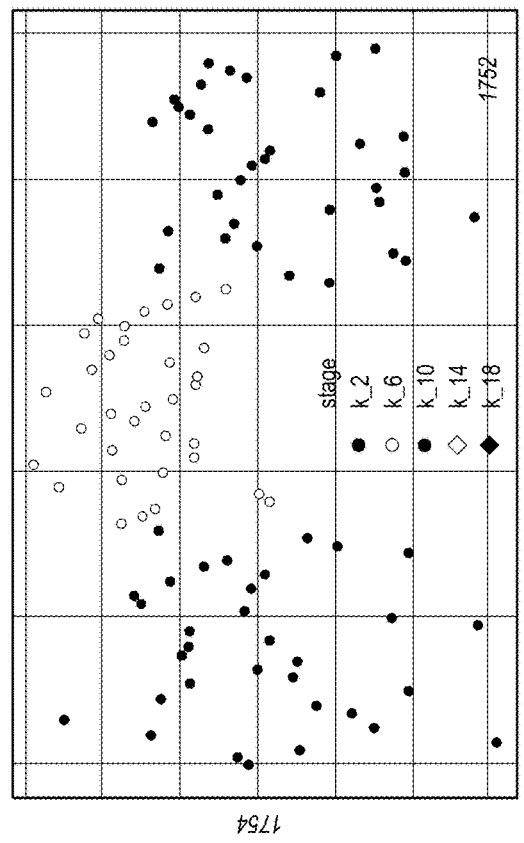
FIG. 17D is a graph 1750 that illustrates anomaly scores from KNN as determined during model evaluation using synthetic data, according to some embodiments.

FIGS. 17B, 17C, and 17D illustrate the specificity of the different types of anomaly detection models for test datasets generated under Scenario 1. FIG. 17B illustrates the test results for an Isolation Forest model, FIG. 17C illustrates the test results for a Random Forest model, and FIG. 17D illustrates the test results for a KNN model. The graphs show the varying performances across the models, as well as across the number of features. In these graphs, the x-axis 1732, 1742, and 1752 represent an experiment number for tests that were run, which used increasing values of the dimensionality k of the observation data, and the y-axis 1734, 1744, and 1754 represent the average anomaly scores generated by the models during model evaluation. The dimensionality of the data is captured by k, where data points of the same type have the same dimensionality k.

A number of insights were gained as a result of the study. In one respect, it was determined that the performance of certain studied model(s) may decrease as the number of features increases. Looking specifically at Isolation Forest, the model was able to detect anomalies when the number of features is small, but performance can drop as the number of features grows to k=18. This drop in performance may be explained based on the nature of Isolation Forest (e.g., because an Isolation Forest is made up of numerous Isolation Trees, each of which takes a random sampling of features; as the number of features increase, it can become increasingly rare for an Isolation Tree to pick up the any one feature that defines the anomaly). Accordingly, in some embodiments, an Isolation Forest model should be preferably combined with a different model that performs better for anomalies of higher dimensionalities (e.g. Random Forest or KNN). The study also revealed that KNN does not perform as well as Isolation Forest or Random Forest. Accordingly, in some embodiments, it is preferable to not use a clustering model alone for this anomaly detection context. Overall, the anomaly detection models in the study were able to achieve a satisfactory detection rate. Executing the anomaly detection pipeline on the synthetic test data resulted in a 85% detection rate at 20 from the mean.

FIG. 18 is a graph 1800 that illustrates a projection of process data points analyzed by a machine learning anomaly detection system, according to some embodiments. In one study, when the anomaly detection system was applied on a real dataset, scores are obtained on each host of a client network for a hunt. The data point for each process on each host are projected into a two-dimensional space for visualization purposes. As shown in the figure, the data points are projected into dimensions 1810 and 1820 in the two-dimensional space, as determined using T-distributed Stochastic Neighbor Embedding (t-SNE). As shown in the graph 1800, there is high density in the center of the graph that decreases toward the edge of the graph, which indicates that most of the observed processes exhibit fairly common behavior, with only a few outliers. In some embodiments, the anomaly detection system may implement a graphical user interface that provides the results of graph 1800 as an aid to security analysts in the hunt process.

In one study, an embodiment of the anomaly detection system was able to identify from actual data anomalous processes that were indicative of: (1) unregistered software to control a given computing device from another malicious computing device. (2) software to move a mouse (or other pointing device) automatically (e.g., a potential security breach), and (3) data transfer software making connections to a malicious external entity (e.g., an exfiltration), among other types of attacks and security incidents.

6. Model Results Interpreter to Determine Important Features of a Detected Anomaly When machine learned models are used to detect anomalies in a computer network, it is often important for security analysts to understand the reasons why a particular observation was flagged as an anomaly. For example, it may be useful to know which features of an observation record caused the observation to be flagged. Such interpretive information can provide vital clues about the nature of the anomaly and serve as a starting point for a more detailed investigation of the anomaly.

However, conventional methods of model results interpretation suffer from a number of shortcomings. In some embodiments, model result interpretation information may be derived based on a linear regression of the observation dataset. For example, a sparse linear regression process may be performed where: (1) the model(s) are executed against client data to obtain anomaly scores. (2) a sparse linear regression with 10% sparsity is performed against anomaly scores on the original features, and (3) feature importance analysis is performed on the regression results to determine what features impacted the anomaly scores and generate an impact report of missing or present values. However, this interpretive approach is limited by the observation data that was collected. Moreover, this approach determines the "important" features based on the entire observation dataset. Thus, the interpretation results may sufficiently explain the anomalies in the context of individual observation records.

Additionally, due to the diversity and complexity of the unsupervised anomaly detection models and the ensemble approach used by the anomaly detection system, there is no obvious method to obtain interpretive information for all models or features. While one may train different interpretive models for individual anomaly detection models or observation features, this brute force approach leads to a large number of interpreter models, which can quickly become intractable. A more flexible interpretation technique is needed for an anomaly detection system that uses many different types of models to examine many different features, or changes the models or features over time.

Accordingly, to overcome these and other technical challenges with conventional model interpretation techniques, embodiments of a model results interpreter are disclosed herein that automatically interprets the anomaly or outlier scores generated by anomaly detection models. The disclosed interpreter can be used to generate interpretation results for any type of anomaly detection model and based on any set of observation features. As discussed previously, the anomaly detection models may output a prioritized list of anomalous or outlier observations that a security analyst should investigate in a hunt process. In order to give the analyst additional insights about the anomaly, the model results interpreter will quantitatively determine a set of features that had the biggest impact on the models' decision to flag the observation. In some embodiments, the model results interpreter may generate a score influence metric that quantifies the effect of each feature on the anomaly score. The influence metric may be generated for one feature at a time. For each feature, the interpreter may generate a comparison observation record, and apply the model(s) to the comparison record to recompute the anomaly score. By analyzing the resulting set of anomaly scores for all features, the model results interpreter will identify those features that were the biggest reasons in causing the anomaly to be flagged. This interpretive information may be provided to the analyst along with the detected anomaly, so that the analyst can use the information to conduct their investigation.

Figure 19A:
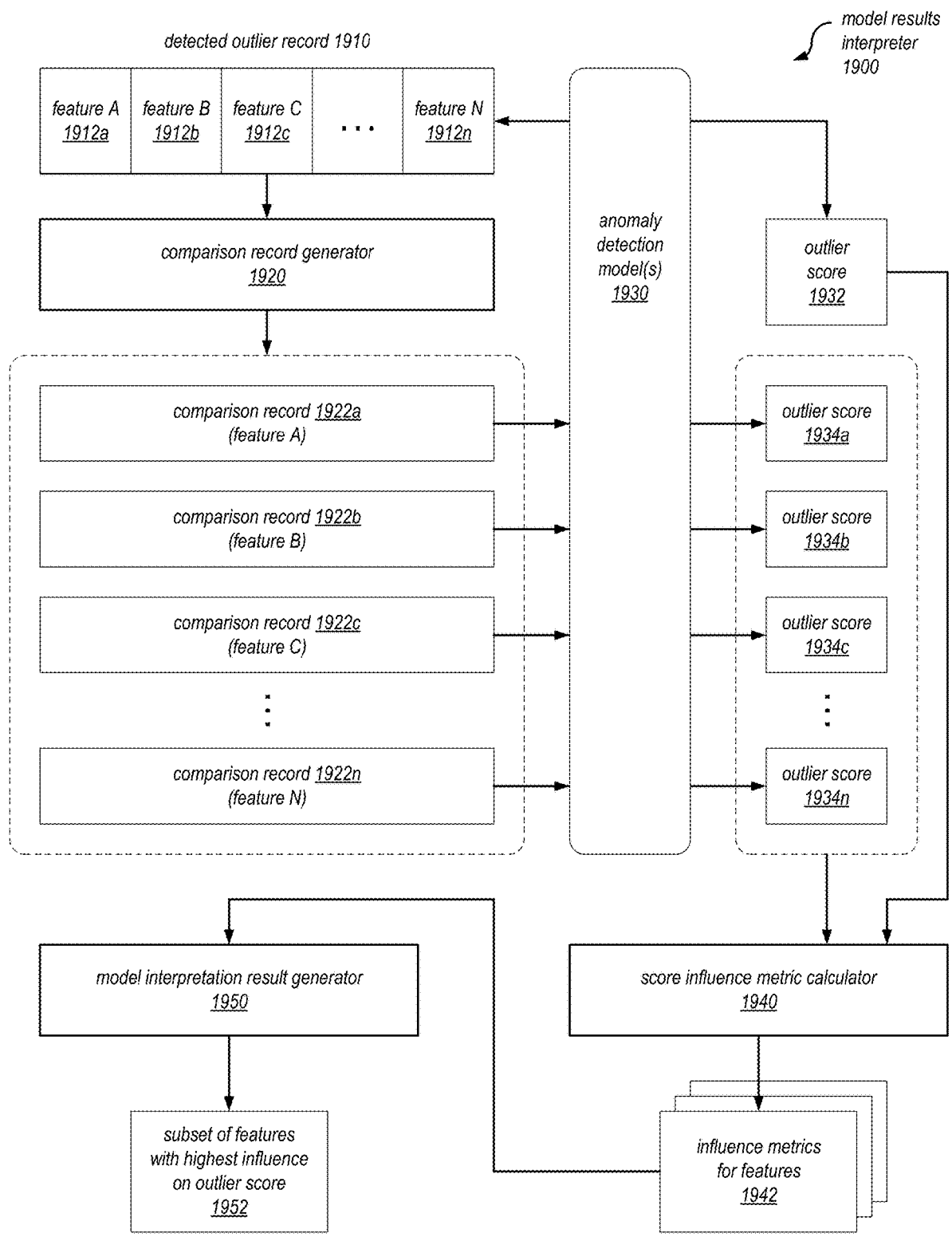
FIG. 19A illustrates the operations of a model results interpreter 1900 that determines features of an outlier record that had the highest influence on the record's outlier score, according to some embodiments.

FIG. 19A illustrates the operations of a model results interpreter 1900 that determines features of an outlier record that had the highest influence on the record's outlier score, according to some embodiments.

The model results interpreter 1900 in this example will analyze a detected outlier record 1910 with a number of observed features 1912a-n, and the outlier score 1932 computed for the outlier record. As shown, the outlier record 1910 may be identified by a set of one or more anomaly detection models 1930 based on the outlier score 1932 determined by the models 1930. The outlier record 1910 may indicate observed data about processes observed in a client network. Depending on the embodiment, the outlier record may represent an observation of a host or machine (e.g. a host feature vector 240 of FIG. 2B) or an observation of a type of process (e.g. a process feature vector 120 of FIG. 2A). As shown, the model results interpreter 1900 will determine a subset 1952 of the features 1912 that had the highest influence or impact on the outlier score 1932.

In some embodiments, to determine the subset of features 1952, the interpreter 1900 will employ a comparison record generator 1920 to generate a series of comparison records 1922a-n. In some embodiments, one comparison record may be generated for each feature 1912 in the outlier record 1910 to be analyzed by the interpreter. In some embodiments, only a subset of the features 1912 may be selected for the analysis in order to reduce the execution time of the interpretation process. For example, in some embodiments, the interpreter may select a subset of the features 1912 to analyze based on their feature variability metric, as discussed in connection with FIG. 5. In some embodiments, the selected features may be determined based on configuration settings specified via a configuration interface.

In some embodiments, the comparison record generator 1920 may generate a comparison record based on a combination of multiple features 1912. For example, if a process observation record P has two features A and B that typically have different values (e.g. A has a bit value of 1 while B has a bit value of 0, or vice-versa), an observed process with the same value for A and B (e.g. both feature bits set to 0) would be considered an anomaly. In this example, the anomaly is based on the state of both features as opposed to the state of either feature individually. To explain such types of anomalous interaction among variables, in some embodiments, the comparison record generator 1920 may generate individual comparison records for multiple features in the observation record. In some embodiments, the comparison record generator may select the multiple features for a comparison record randomly or based on configuration settings.

In some embodiments, the comparison record 1922 may be generated by making modifications to the outlier record 1910. In some embodiments, the feature being examined (e.g. feature A for record 1922a) may be retained in the comparison record, while all other features are changed or set to a specified value (e.g. zero). In some embodiments, the examined feature may be modified while the other features in the outlier record are retained. As discussed in connection with FIGS. 2A and 2B, each feature may be encoded as individual bits, a group of bits, individual continuous values, or a vector of continuous values. As shown, the generated comparison records 1922 are analyzed by the same set of anomaly detection model(s) 1930 that identified the outlier record 1910, and a corresponding set of new outlier scores 1934a-n are obtained.

As shown, the new outlier scores 1934 and the original outlier score 1932 are then provided to a score influence metric calculator 1940 to obtain influence metric values 1942 for each of the individual features 1922a-n. In some embodiments where the examined feature is retained in the comparison record, a larger value of the new outlier score 1934 will result in a higher value for the score influence metric 1942. In some embodiments, the influence metric may be determined based on the difference between the original outlier score 1932 and the new outlier score 1934 for a particular comparison record 1922. For example, in some embodiments where the examined feature is changed in the comparison record, a large decrease in the new outlier score 1934 may indicate a higher value for the score influence metric 1942. In some embodiments, once the influence metrics 1942 are generated for all features 1912, they may be normalized to a common value range, so they can be fairly compared with one another. For example, the score differences may be reduced to a fraction or percentage of the original outlier score 1932, or assigned to a value between 0 and 1 using a normalization function.

In some embodiments, the influence metric values of all features may be determined at the same time, for example, by fitting or tuning a linear model to approximate the original outlier score 1932 based on a linear combination of the new outlier scores 1934 computed for the comparison records. In some embodiments, the resulting coefficients of the linear model may be used to derive the influence metrics 1942 of the features (e.g. where higher feature coefficients indicate larger influence metric values).

As shown, once the influence metric values 1942 for the individual features 1912 are determined, they are used by a model interpretation result generator 1950 to generate a model interpretation result, which may be provided to security analysts along with the model's explicit findings (e.g. the outlier record 1910 and the outlier score 1932). In some embodiments, the model interpretation results may indicate the subset of the features 1952 with the highest influence metric values. That is, the model interpretation results will indicate the features that were the biggest factors in the models' decision to flag the outlier record. In some embodiments, the subset of features 1952 may be selected based on a ranking of the features 1912 according to their influence metric value. In some embodiments, the subset of features 1952 may be selected based on a configured selection criterion, such as a minimum threshold value of the influence metric. The selected features 1952 may be used by the security analyst to conduct a more detailed analysis of the detected outlier observation 1910.

Figure 19B:
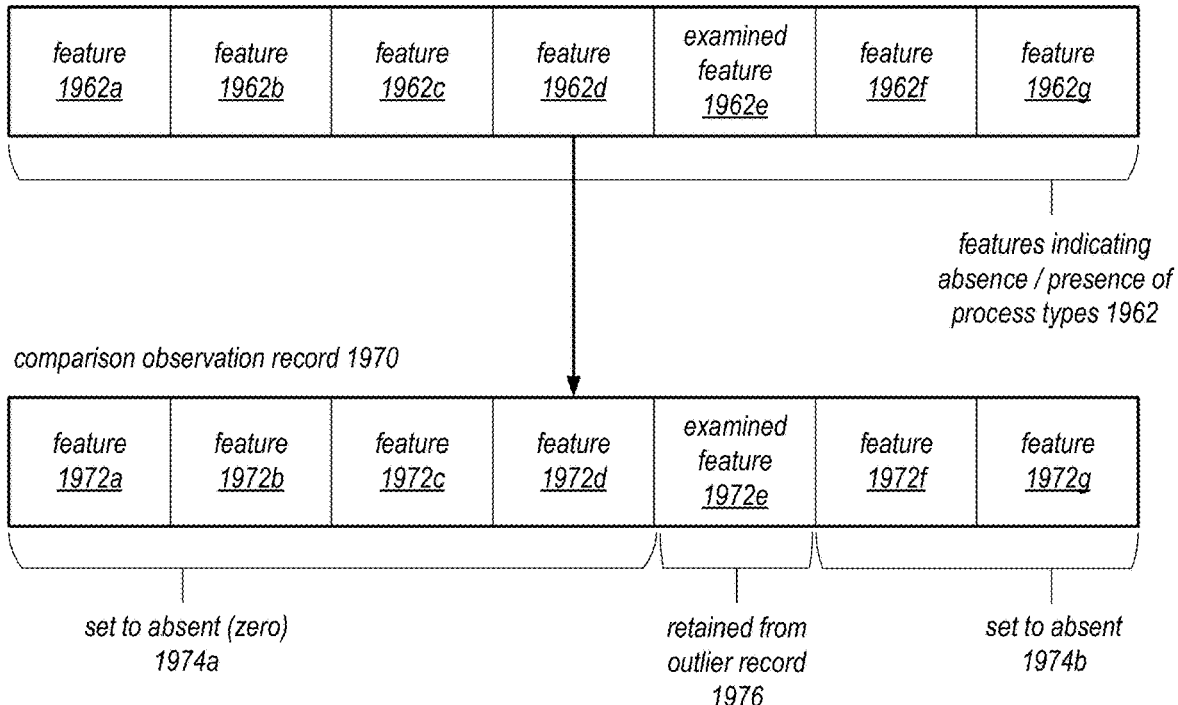
FIGS. 19B and 19C illustrate different ways of generating comparison records used to calculate a feature's influence on an observation record's outlier score, according to some embodiments.
Figure 19C:
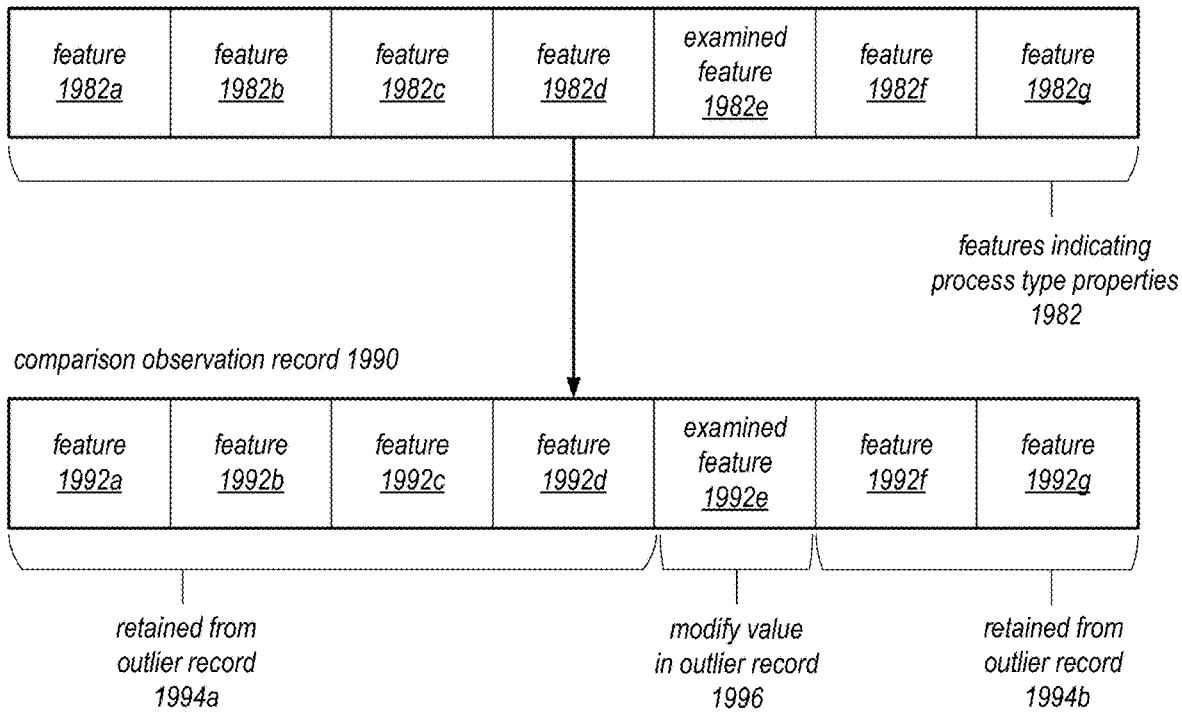

FIGS. 19B and 19C illustrate different ways of generating comparison records used to calculate a feature's influence on an observation record's outlier score, according to some embodiments. The comparison records 1970 and 1990 in the two figures may be generated using different embodiments of the comparison record generator 1920, as discussed in connection with FIG. 19A.

In FIG. 19B, the outlier record 1960 represents an observation of a machine. In this example, the features 1962a-g may represent data about different process types and indicate whether each process type was observed on the machine during an observation period, as discussed in connection with FIG. 2B. As shown, a comparison record 1970 is generated based on the outlier record, which will be used to examine the impact or influence of a feature 1962e on the outlier score. As shown, the generated comparison record 1970 in this example retains the value of the examined feature 1962e in its corresponding feature 1972c. However, all of the other features 1972a-d and 1972f-g in the comparison record are set to zero 1974 to indicate the absence of all other process types on the machine. In this manner, the comparison record 1970 can be used to isolate the effect of the examined feature 1962e (a particular process type) on the outlier score during the interpretive process. As discussed, this comparison record generation step may be repeated for each feature 1962a-g in the outlier observation record 1960.

In FIG. 19C, the outlier record 1980 is an observation of a particular type of process. Such an observation record may include features 1982a-g that indicate various observed properties of the process type, such as the loaded executable, average execution time, etc., as discussed in connection with FIG. 2A. As shown in this example, the comparison record 1990 retains 1994 all features 1992a-d and 1992f-g from the outlier record 1980. However, the value of the examined feature 1982e is modified 1996 in the comparison record 1990. Thus, the comparison record 1990 illustrates another technique for isolating the effects of a particular feature on the outlier score. In embodiments where the examined feature 1982e is a single bit, the modification may simply flip the bit in the comparison record 1990. In some embodiments where the examined feature 1982e includes multiple bits or is a continuous value, the modification may involve randomly generating a new value for the corresponding feature 1992e in the comparison record 1990. In some embodiments, the comparison record generator 1920 may be configured to generate multiple comparison records with different values for the examined feature 1992c.

7. Example Implementation of Anomaly Detection Pipeline for Identifying Anomalous Processes or Hosts in Hunt Data Analyzing metadata about processes in a computer network can be an effective method to identify compromised machines, assets, devices, and the like. Unfortunately, the enormous volume of process-related data makes existing and traditional approaches of analyzing the data difficult from a technological standpoint. Accordingly, to address these and other problems in the state of the art, a machine learning anomaly detection system is disclosed to detect outlier processes or hosts to be prioritized for human investigation. In some embodiments, the machine learning models used by the system are trained using unsupervised machine learning methods, so that the data for training and testing models do not need to be manually labeled.

Figure 20:
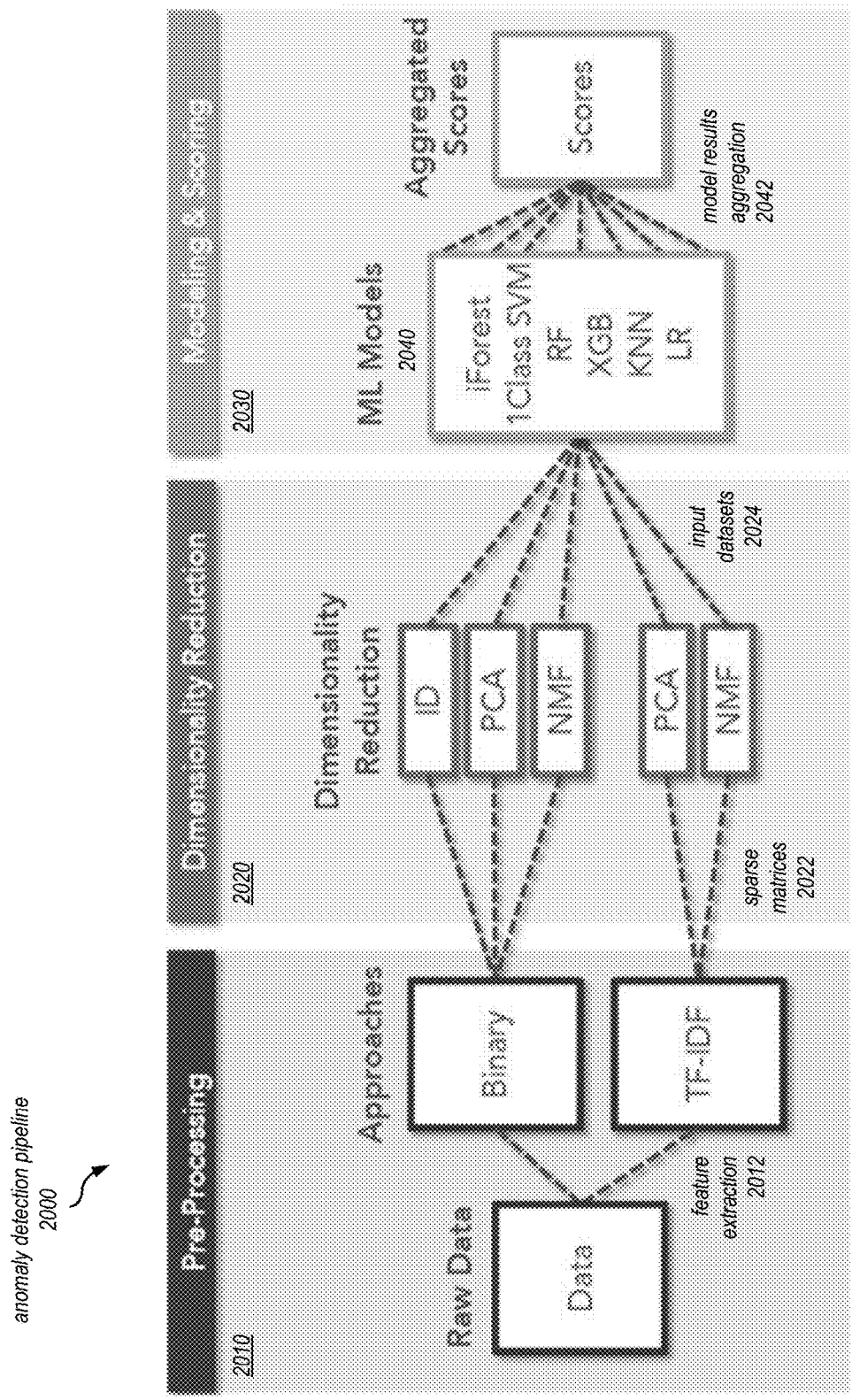
FIG. 20 is a block diagram illustrating an anomaly or outlier detection pipeline implemented by a machine learning anomaly detection system, according to some embodiments.

FIG. 20 is a block diagram illustrating an example outlier detection pipeline of a machine learning anomaly detection system that is implemented using the techniques discussed previously. In some embodiments, the pipeline 2000 may be implemented by a fleet of computers implemented in a cyberattack monitoring service (e.g. a MDR service). The cyberattack monitoring service may be configured to periodically collect data from a client network and monitor the data for signals of a cyberattack, compromise, or security threat, etc. In some embodiments, the cyberattack monitoring service may be configured to use the pipeline 2000 to programmatically examine regularly received observation data (e.g. once a week), to identify anomalies in the data (e.g. oddly behaving processes or hosts) to be more closely examined by human analysts as part of a hunt process.

As shown in this example, the pipeline 2000 is divided into stages, including a pre-processing stage 2010, a dimensionality reduction stage 2020, and a modeling and scoring stage 2030. In some embodiments, the stages are executed sequentially, but not necessarily synchronously. Thus, the completion of one stage in the pipeline does not necessarily cause the next stage to immediately begin execution. Rather, these stages may be performed in a loosely orchestrated manner, which may be controlled via a pipeline manager component (e.g. the anomaly detection pipeline manager 3120 of FIG. 31). In some embodiments, the pipeline manager component may provide a user interface (e.g. a graphical user interface) that can be used by an administrator of the pipeline to view the execution progress of the pipeline, and/or control the execution of the pipeline (e.g. to start, stop, or repeat particular stages in the pipeline).

As shown, the pre-processing stage 2010 begins with raw data, which may be the observation records 130 of processes collected from the client network for a certain observation period (e.g. for a particular week). In some embodiments, the raw data may also include data from other sources, such as intelligence reports from third parties describing known malware, cyberattacks, etc. Such third party data may be used to augment the observed features of the raw data. In some embodiments, the raw data may be reported as logs of process events (e.g. process launch events), which are captured by data collection agents executing within the client network.

As shown, the raw data is converted into feature vectors via feature extraction step 2012. As discussed previously, feature extraction may involve augmenting the features of the observation records with additional features, and then re-encoding the features into a feature vector representation. In some embodiments, the anomaly detection pipeline 2010 may support multiple feature vector representations, such as a binary representation or a TF-IDF representation. In some embodiments, other types of feature vector encodings may also be used. In some embodiments, the anomaly detection pipeline may provide a configuration interface to allow an administrator to select the representation of the feature vectors. In some embodiments, the result of the pre-processing stage may include one or more sparse matrices 2022 of feature vectors (e.g. matrices 200 or 230). In some embodiments, one matrix 2022 will be generated for each category of observation records (e.g. a group of processes having the same executable path). In some embodiments, the matrices may be saved as files at a location that is accessible by the next stage of the pipeline.

As shown, the dimensionality reduction stage 2020 may employ a number of dimensionality reduction techniques, such as PCA, NMF, or an Auto Encoder, etc. In some embodiments, a statistical driven feature reduction method as discussed in connection with FIG. 5 or 6 may be used. In some embodiments, some of the dimensionality reduction techniques may be associated with a machine learning model, which may be trained using unsupervised learning techniques without the use of labeled data. In some embodiments, the pipeline may allow an administrator to select a particular dimensionality reduction technique via the configuration interface. In some embodiments, the result of stage 2020 will include input datasets 2024 of feature vectors with reduced dimensions, which are ready for use by the outlier detection models 2040 of the next stage.

As shown, the modeling and scoring stage 2030 may be performed using a number of machine learning models, such as Isolation Forest, One-Class SVM, or other classification models trained to distinguish between real and synthetic data. In some embodiments, the models 2040 may be trained using unsupervised learning techniques and without the use of labeled data. In some embodiments, one or more of the models may be trained using programmatically labeled data without human labeling. In some embodiments, each model 2040 will accept input feature vectors from the input datasets 2024 and generate an outlier metric for each input feature vector. The outlier metric may indicate a quantitative measure of how abnormal an observed process or host is based on historical observations. In some embodiments, outlier processes are determined based on historical records of processes in the same process category. In some embodiments, outlier hosts may be determined based on historical records of that host or a similar group of hosts.

In some embodiments, the anomaly detection pipeline may use more than one outlier detection model for each input dataset 2024. For example, each input feature vector may be examined by several machine learned models to obtain multiple model results, and these results may be aggregated 2042 using an aggregation technique (e.g. a formula or another ML model) to obtain an overall outlier metric or score for the feature vector. In some embodiments, the formula for computing the aggregated score may be configurable by an administrator. In some embodiments, the formula may be automatically adjusted by the anomaly detection system. For example, the weights assigned to individual model results may be periodically tuned by the system based on the recent performance of the models, or based on how far the results of one model deviate from the others.

In some embodiments, the multiple machine learning models 2040 may execute together as a single ensemble. Depending on the embodiment, various result aggregation strategies 2042 may be employed for the ensemble. For example, in some embodiments, the aggregated score may represent a weighted average of scores produced by the constituent models. In some embodiments, the aggregation may ignore the highest and/or lowest scores produced by the constituent models. In some embodiments, a voting scheme may be used where the constituent models cast votes for a particular observation to be designated as an outlier. In some embodiments, the aggregation may be performed by an aggregator model, which may be trained (e.g. using unsupervised techniques) to combine results from the constituent models to generate the aggregated outlier score. In some embodiments, the aggregator model may be trained using a supervised training technique using small amounts of labeled data.

In some embodiments, the models 2040 may be used to produce outlier scores for each observation record that is relative to other records in the observation record's category (e.g. process categories 120). Thus, for example, to detect an outlier score for a MICROSOFT EXCEL process, that particular process is compared to all "normal" historical processes of MICROSOFT EXCEL seen by the model. In some embodiments, observation records of hosts may also be categorized based on a combination of characteristics of the hosts. In some embodiments, at least some of the models 2040 may be trained (e.g. using supervised training techniques) to generate scores for observation records that are based on historical examples of attacks. In some embodiments, the anomaly detection system may implement different sets of models for each observation category.

In other embodiments, the anomaly detection system may use the same models for all observation categories, but use statistical techniques to generate an outlier score that is specific to each category. For example, the system may use a single model to produce raw outlier scores for all observation categories. However, a raw outlier score may then be ranked against only the scores of observations in the same category, to obtain a percentile ranking of the observation within the category. In some embodiments, the outlier scores may be normalized (e.g. to have a mean value of 0 and a variance of 1) so that they can be compared across all categories. In some embodiments, detected outliers for each category may be ranked, and only a specified number of highest ranked outliers are outputted as detected anomalies (e.g. anomalous processes or hosts). In some embodiments, the manner that the aggregated score is calculated may be configurable using a configuration interface of the anomaly detection system.

It will be appreciated that security analysts in modern SOCs deal with a massive amount of data and have to cull through this data to find intrusions and anomalies. The anomaly detection pipeline disclosed herein may be used to reduce the analysts' work during the hunt process. For example, the anomaly detection system may be configured to tag 95% of incoming observation records as normal and 5% as anomalous, leaving this 5% to be the focus of investigations and further action by analysts. In this manner, the time and resources that security analysts spend on hunt analysis is significantly reduced.

It will also be appreciated that in some embodiments, the anomaly detection pipeline may be used for other types of data analysis. For example, in some embodiments, the disclosed pipeline can be used to analyze collected data for vulnerability management, incident detection and response, security workflow generation for automation and orchestration, penetration testing, application security testing, and a variety of other operations of a cyberattack monitoring service.

Figure 21:
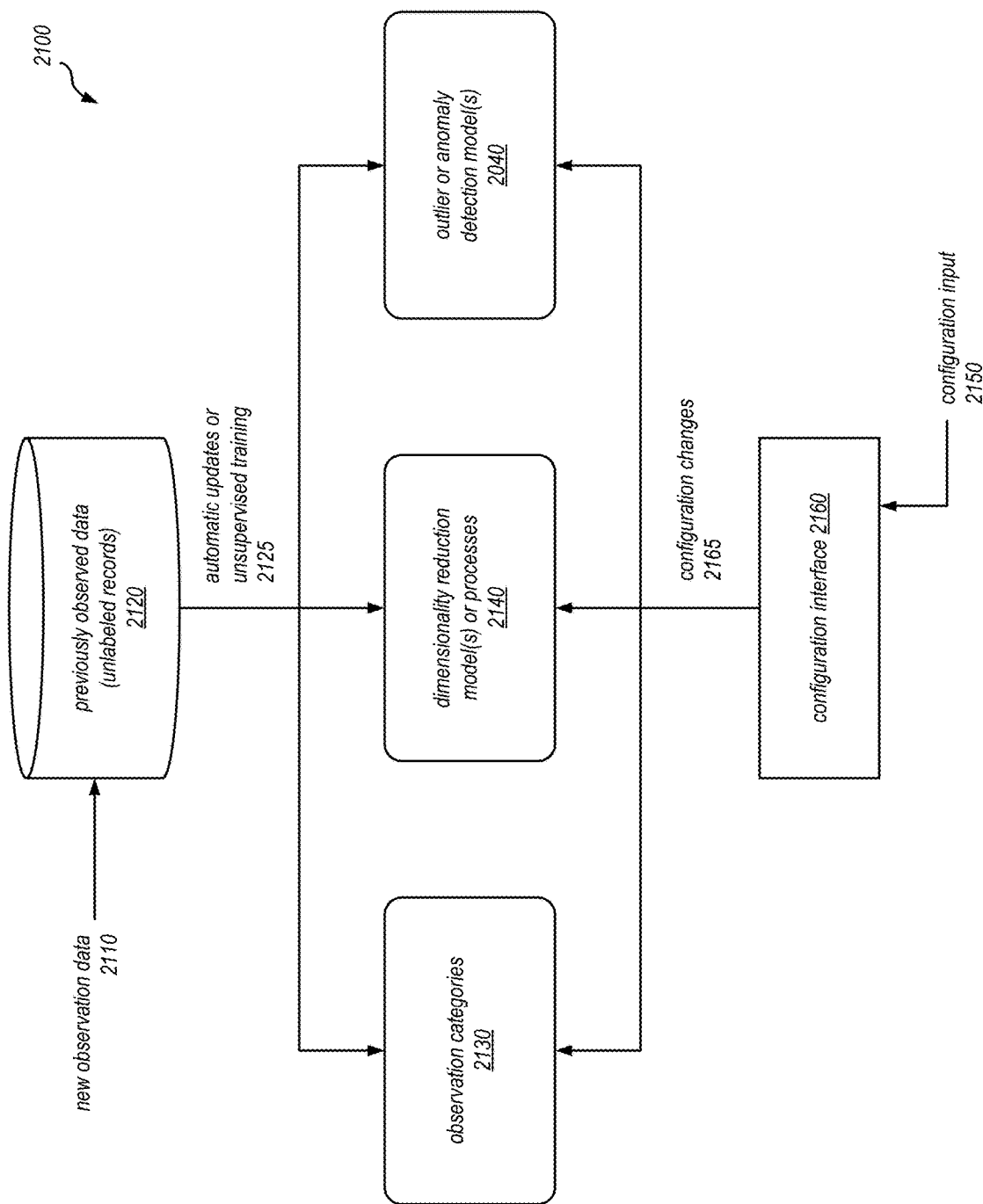
FIG. 21 is a block diagram 2100 illustrating the automated updating of components of the machine learning anomaly detection system, according to some embodiments.

FIG. 21 is a block diagram 2100 illustrating automated updating of components of the machine learning anomaly detection system, according to some embodiments.

As shown, the figure depicts the automated updating of a number of pipeline components, including observation categories 2130 (e.g. categories 120 of FIG. 1A), dimensionality reduction models or processes 2140 (e.g. the dimensionality reduction models or processes discussed in connection with FIG. 4A, 5, or 6), and outlier detection models 2040 as discussed in connection with FIG. 11. In some embodiments, all of these components may be automatically updated or trained 2125 based on new observation records 2110 collected from client network(s).

As shown, in some embodiments, new observation records 2110 collected for an new observation period (e.g. hunt data including process observation records) may be stored in a data store or repository 2120. The data store 2120 may store an archive of previously observed data about host behavior. In some embodiments, this observation data is unlabeled for machine learning purposes (e.g. the data are not designated with truth labels indicating records as outlier or non-outlier observations). In some embodiments, the previously observed data 2120 may be organized by observation category.

In some embodiments, the previously observed data 2120 may only contain "normal" observations that were not later determined to be associated with cyberattacks. For example, in some embodiments, if a process is later confirmed to be part of a cyberattack after human review, that process may be removed from the data store 2120, so that the models of the anomaly detection system are not trained to identify such a process as a "normal" observation. In some embodiments, processes or hosts that are confirmed to be associated with cyberattacks and/or intrusions may be archived in a different database. In some embodiments, the feature vectors of such processes or hosts may be used to scan future observation data to programmatically detect similar attacks or intrusions. In some embodiments, archived incidents of attacks may be used as examples of anomalies or further leveraged to create synthetic data in their vicinity.

As shown, the observation categories 2130 may be periodically updated using the previously observed data 2110. For example, when new software (e.g. new executables) is installed on hosts in the client network, additional observation categories (e.g. categories based on paths of the executables) may be automatically generated. In some embodiments, the observation categories may be machine learned classes or aggregate data structures, and these classes or data structures may be periodically relearned or updated using recent observations. In some embodiments, when the observation categories 2130 are changed, an update of some or all of the downstream models may be triggered.

As shown, the dimensionality reduction models or processes 2140 may also be periodically updated or trained 2125 using unsupervised learning techniques. For example, a set of dimensions determined by a PCA dimensionality reduction technique may be periodically updated based on a sample of recent data stored in the data store 2120. Such periodic adjustments to the dimensionality reduction models or processes 2140 will ensure that the rest of the anomaly detection pipeline uses the best features for detecting outliers in the data. In some embodiments, changes in the dimensionality reduction models will also cause downstream models such as the outlier detection models 2040 to be updated.

As shown, in some embodiments, the outlier detection models 2040 may also be periodically updated or trained 2125, using supervised or unsupervised machine learning techniques. For example, an Isolation Forest model may periodically be regenerated to adapt to new features in newly observed data. In some embodiments, the outlier detection models may also be periodically evaluated using automated model evaluation techniques (e.g. using model evaluator 2720 of FIG. 27). Model updates may be triggered based on the results of these evaluations.

In some embodiments, the observation categories 2130, dimensionality reduction models or processes 2140, and outlier detection models 2040 may be updated via configure settings received via a configuration interface 2160 of the anomaly detection system. In some embodiments, the manner in which these components are automatically updated are also controllable via the configuration interface. In some embodiments, the configuration interface 2160 may be provided as a web-based GUI configured to receive configuration input 2150 from an administrator. The configuration interface will translate the configuration input 2150 into configuration changes 2165 for the management subsystems for each of the pipeline components. In some embodiments, the configuration input 2150 may specify the schedule of the automatic updates or conditions that will trigger pipeline component updates. In some embodiments, the configuration input may explicitly define specific observation categories (e.g. combining multiple executable paths into a single category, and which execution paths to be ignored, etc.). In some embodiments, the configuration input may specify which dimensionality reduction models are to be used, and the number of features that will be retained in the input datasets. In some embodiments, the configuration input may specify which outlier detection models will be used under what conditions, and how the results of the outlier detection models will be aggregated to determine the ultimate outlier metric for an observation.

It will be appreciated that while the configuration interface 2160 allows humans to control certain behaviors of the anomaly detection system when desired, the system does not require any human input to perform the automatic updates 2125. That is, embodiments of the anomaly detection system are capable of making self-adjustments based on the incoming observation data in a completely unsupervised manner. Accordingly, the anomaly detection system is designed to automatically and continuously learn from new observation data without human input.

Embodiments of the disclosed anomaly detection pipeline address the unique technical challenges the hunt process, and is configured to detect outliers in the hunt data by performing: (1) a normalizing step to remove small variations in the data (e.g. in the naming of the processes), (2) a dimensionality reduction step to reduce the very large dimensionality of the data (e.g. number of possible features), and (3) a modeling and scoring step to aggregate results from multiple machine learning models to generate an outlier metric for an observed process or host. In some embodiments, the anomaly detection pipeline 2000 may compute and determine an anomaly score using an ensemble of independent machine learning models and aggregates the results. The aggregated scores may be used as the metrics for assigning priority for a security analyst (e.g., in a SOC) to investigate the detected anomalies for further action (e.g., to be performed by the security operations engine 3130 of FIG. 31).

In certain embodiments, the anomaly detection pipeline 2000 may be implemented to perform at least the following operational steps: (1) access or receive raw data for multiple distinct processes (e.g., software processes) executing or running across multiple distinct hosts, (2) perform preprocessing (e.g., binarization or TF-IDF encoding of the data), (3) perform dimensionality reduction (e.g., using PCA, NMF, or Auto Encoder), (4) invoke one or more machine learning models (e.g., as shown in FIG. 20) to produce respective anomaly scores or results, and (5) aggregate the models' scores or results (e.g., using median, mean, or some other type of aggregation technique) to generate an aggregated score for individual observations of processes or hosts.

Figure 22A:
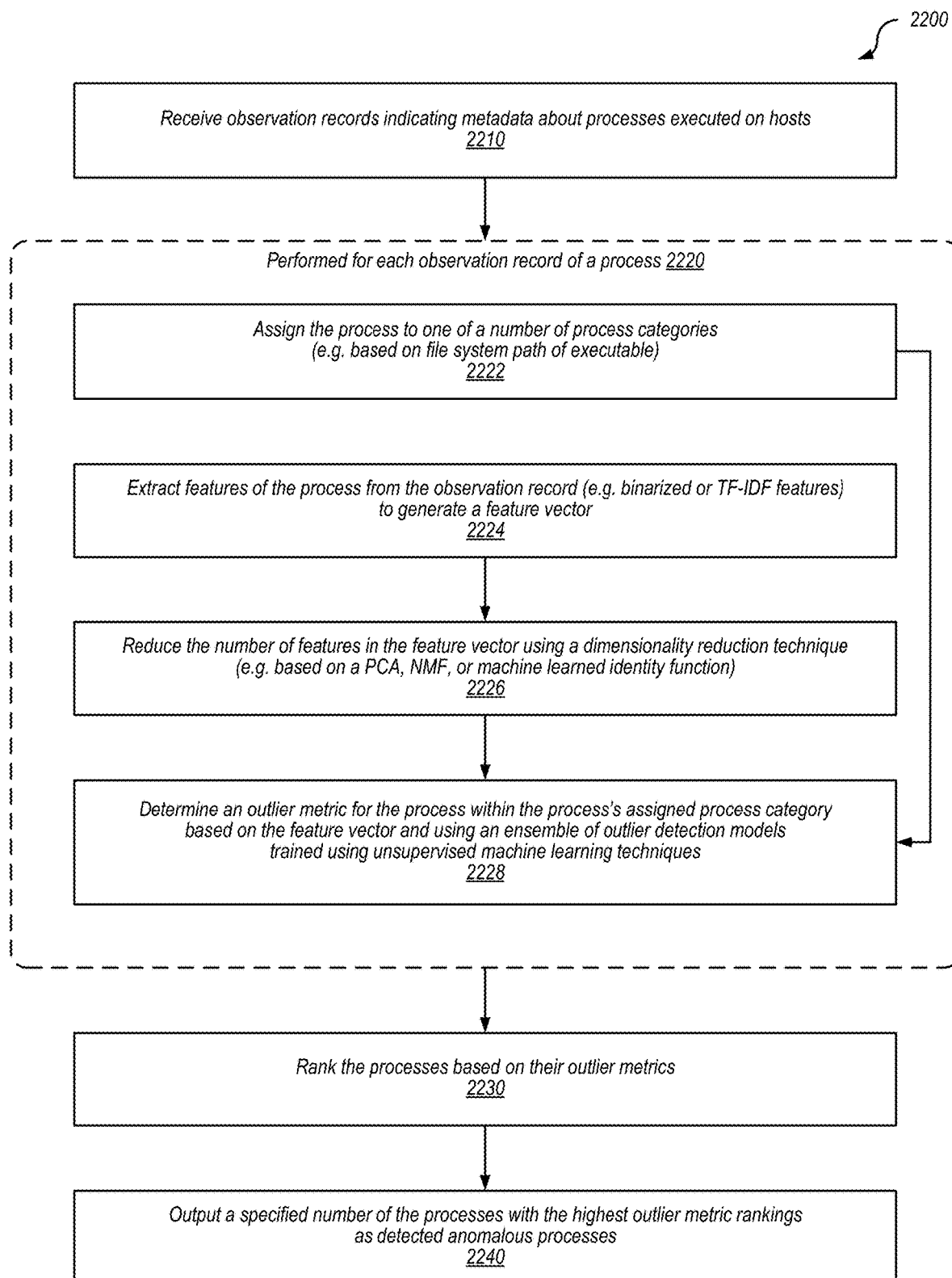
FIGS. 22A and 22B show a flowchart 2200 illustrating a process of detecting anomalous processes and hosts performed by a machine learning anomaly detection system, according to some embodiments.
Figure 22B:
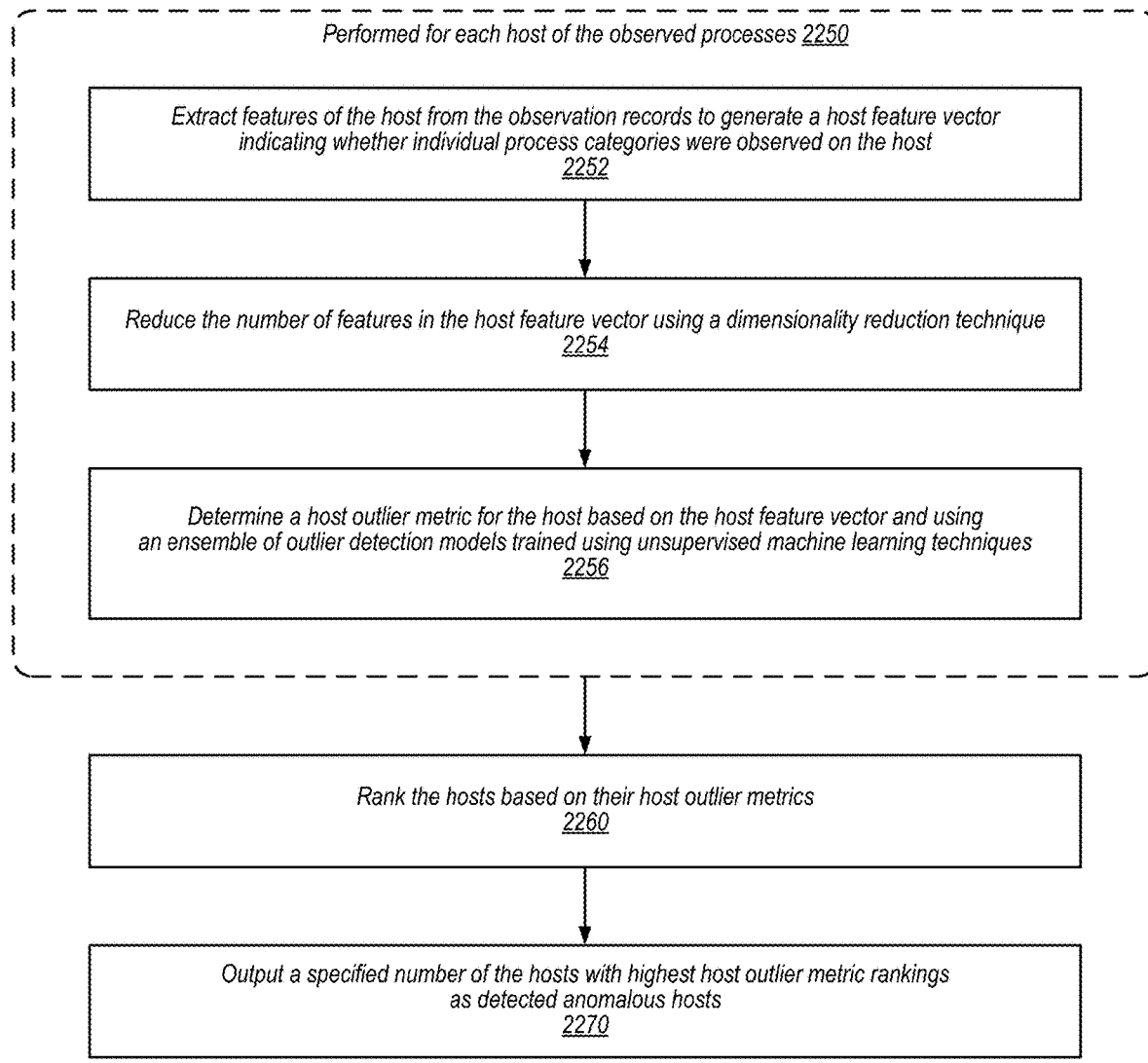

FIGS. 22A and 22B show a flowchart 2200 illustrating a process of detecting anomalous processes and hosts performed by a machine learning anomaly detection system, according to some embodiments. The depicted process may be performed by an embodiment of a machine learning anomaly detection system, as shown for example in FIGS. 31 and 32.

The process begins at operation 2210, where observation records are received. The observation records (e.g. observation record 130 of FIG. 1A) may include metadata about processes that were executed on hosts in a client network monitored by the anomaly detection system. In some embodiments, data collection agents may be deployed on hosts in the client network in order to gather the observation records.

As shown, operations 2222, 2224, 2226, and 2228 are performed 2220 for each observation record associated with an observed process. At operation 2222, the process is assigned to one of a number of process categories (e.g. process categories 120). In some embodiments, each process may be assigned to a category based on the file system path of the executable that was executed by the process. In this manner, all processes assigned to the same category may be processes that executed the same executable or a group of related executables in the same file system directory. In some embodiments, a normalization step may be performed to eliminate irrelevant variations in the naming of the processes, executables, or file system paths. In some embodiments, processes that are assigned to the same category are expected to exhibit similar behavior (e.g. have similar features or attributes), and an outlier process is determined based on other processes in the same category.

At operation 2224, features of the process are extracted from the observation record to generate a feature vector (e.g. feature vector 210 of FIG. 2A). In some embodiments, the feature extraction process may involve augmenting the observation record with additional data from other sources. In some embodiments, a feature vector for a process may encode the process as a document of terms. In a binarized form, the feature vector may include 0s and 1s indicating the absence or presence of individual feature values. In a TF-IDF form, the feature vector may include TF-IDF scores for individual feature values with respect to a corpus of previous observation records. In some embodiments, the generated feature vectors may be compiled into a sparse matrix, such as matrix 200 of FIG. 2A.

At operation 2226, the number of features in the feature vector are reduced using a dimensionality reduction technique. In some embodiments, the dimensionality reduction technique uses a machine learning model that was trained using an unsupervised machine learning technique. In some embodiments, the dimensionality reduction technique may be one or more of PCA, NMF, or an Auto Encoder. In some embodiments, the number of features may be reduced based on a feature variability metric computed from historical data. The result of the dimensionality reduction operation is an input dataset of smaller feature vectors that are ready for consumption by the outlier detection models.

At operation 2228, the anomaly detection system determines an outlier metric for the process within the process's assigned category based on the feature vector and using an ensemble of outlier detection models trained using unsupervised machine learning techniques. In some embodiments, the individual results of the outlier detection models are aggregated using a weighted average formula, a voting scheme, an aggregator model, or some other aggregation technique. In some embodiments, the outlier detection models in the ensemble may include an Isolation Forest model or a One-Class SVM. In some embodiments, other types of models such as classifiers trained using automatically labeled data may also be used. Example types of classifier models that may be used include Random Forest, XGBoost, K-Nearest Neighbor, and Logistic Regression, Neural Network. In some embodiments, the system may maintain one set of models for each process category. In some embodiments, the system may use the same set of models for multiple process categories.

At operation 2230, the processes are ranked based on their determined outlier metrics. In some embodiments, the outlier metrics of the processes may be normalized so that they can be compared across process categories. For example, a particular process's outlier metric may be normalized to indicate how extreme of an outlier it is within its own category. In some embodiments, all observed processes collected for a given observation period are ranked according to their outlier metrics, so that the highest ranked processes are the most extreme outliers within their respective categories.

At operation 2240, a specified number of processes with the highest outlier metric rankings are selected and outputted as detected anomalous processes. For example, the anomaly detection system may identify the detected anomalous process on a GUI or in an alert. In some embodiments, such output may be used by security analysts at a SOC to assign priority to individual processes or hosts for investigative actions. By outputting only a specified number of anomalous processes, the anomaly detection system does not overwhelm security analysts with a huge volume of anomalies during the hunt process.

FIG. 22B illustrates the building and use of a host feature vector to detect outlier hosts. The depicted process in FIG. 22B may be performed independently or in conjunction with the process outlier detection process of FIG. 22A. In some embodiments, the outlier host detection process may be performed after the process outlier detection process of FIG. 22A.

As shown, operations 2252, 2254, and 2256 in the illustrative process are performed 2250 for each host seen in the observation records. At operation 2252, features of an individual host are extracted from the observation records to generate a host feature vector (e.g. feature vector 240 of FIG. 2B). In some embodiments, the host feature vector will include features of individual process categories, such as whether each individual process category was observed on the host during an observation period. In some embodiments, the host feature vector may include a group of features for each process category (e.g. features 260*a-n* for process category A in FIG. 2B). Depending on the embodiment, such process category features may indicate the number of processes of the category were executed on the host, whether an outlier process was detected in the category, the number of outlier processes that were detected in the category, the total amount of network connections made by processes in the category, the average execution time of processes in the category, among other types of features.

At operation 2254, the number of features in the host feature vector is reduced using a dimensionality reduction technique. In some embodiments, the dimensionality reduction may be performed using a machine learned model that was trained using an unsupervised machine learning technique. Operation 2254 may be performed in a similar manner as operation 2226 of FIG. 22A.

At operation 2256, a host outlier metric is determined for the host based on the host feature vector and using an ensemble of outlier detection models trained using unsupervised machine learning techniques. In some embodiments, the host outlier detection models used by operation 2256 are different from the process outlier detection models of operation 2228. In some embodiments, an outlier host is determined with respect to all hosts in the client network in the historical data. In some embodiments, a host is determined to be an outlier by comparing its feature vector with previous feature vectors collected for the same host. In some embodiments, an outlier host is determined with respect to a category of similar hosts (e.g. similar file servers) and with a specified time period (e.g. within the last month), as configured by administrators of the anomaly detection system. In some embodiments, operation 2256 may be performed in a similar manner as operation 2228 of FIG. 22A.

At operation 2260, the hosts are ranked based on their host outlier metrics. Operation 2260 may be performed in a similar manner as operation 2230 of FIG. 22A for processes. Finally, at operation 2270, a specified number of hosts with the highest host outlier metric rankings are outputted as detected anomalous hosts. Operation 2270 may be performed in a similar manner as operation 2240 of FIG. 22A.

8. Example System and Method for Automated Dimensionality Reduction Based on Feature Value Variability Anomaly detection on MDR hunt data is plagued by high dimensionality. The number of possible computing and software processes on a given network is enormous and makes outliers much more difficult for algorithms to identify. To reduce the number of dimensions, embodiments of the anomaly detection system may implement an anomaly detection model manager, which is capable of automatically determining which features are the most useful for spotting outliers in the data.

Automated dimensionality reduction for supervised algorithms or models generally consist of finding and removing the features that contribute the least to a model's accuracy. Anomaly detection, however, is typically carried out using unsupervised models, which means the model developer does not have access to model accuracy metrics for choosing which features to discard and which features to retain.

In some embodiments of the anomaly detection pipeline 2000, a model manager may be employed to perform an automated procedure to find and eliminate sources of redundant information in the observation data, for example, features that are correlated and therefore add no new information independently. In some embodiments, the automated process may include a dimensionality reduction process, which include at least the following steps: (1) for each column or feature the observation dataset (a matrix), (i) remove the column c, (ii) reduce the matrix to a desired number of columns, (iii) fit a random forest to predict values in the removed column c, and (iv) repeat over all columns c to get an average quality; (2) repeat over k to get average metrics for each value of k; (3) repeat for each size of lower dimensions; and (4) speed up and optimize the foregoing process by training a model over k, number of rows, density, and rank.

In some embodiments, the model manager may be configured to eliminate features based on how dispersed the feature's observed values are. This dimensionality reduction approach is specifically adapted to finding the best features to use for anomaly detection applications in an unsupervised setting, by targeting features that are useful for anomaly detection (e.g., features with predictable values in narrowly bounded ranges), and avoiding "noisy" features with high value dispersion, which tend to mask outlier behavior. In some embodiments, the model manager is configured to capture the variability of individual features using a feature variability metric (e.g. the standard deviation or variance of observed values of the feature). The model manager will keep a subset of the features with acceptably low variability measures, and discard other features with high variability measures. By removing the noisier features, the anomaly detection process can be performed more accurately and efficiently.

Figure 23:
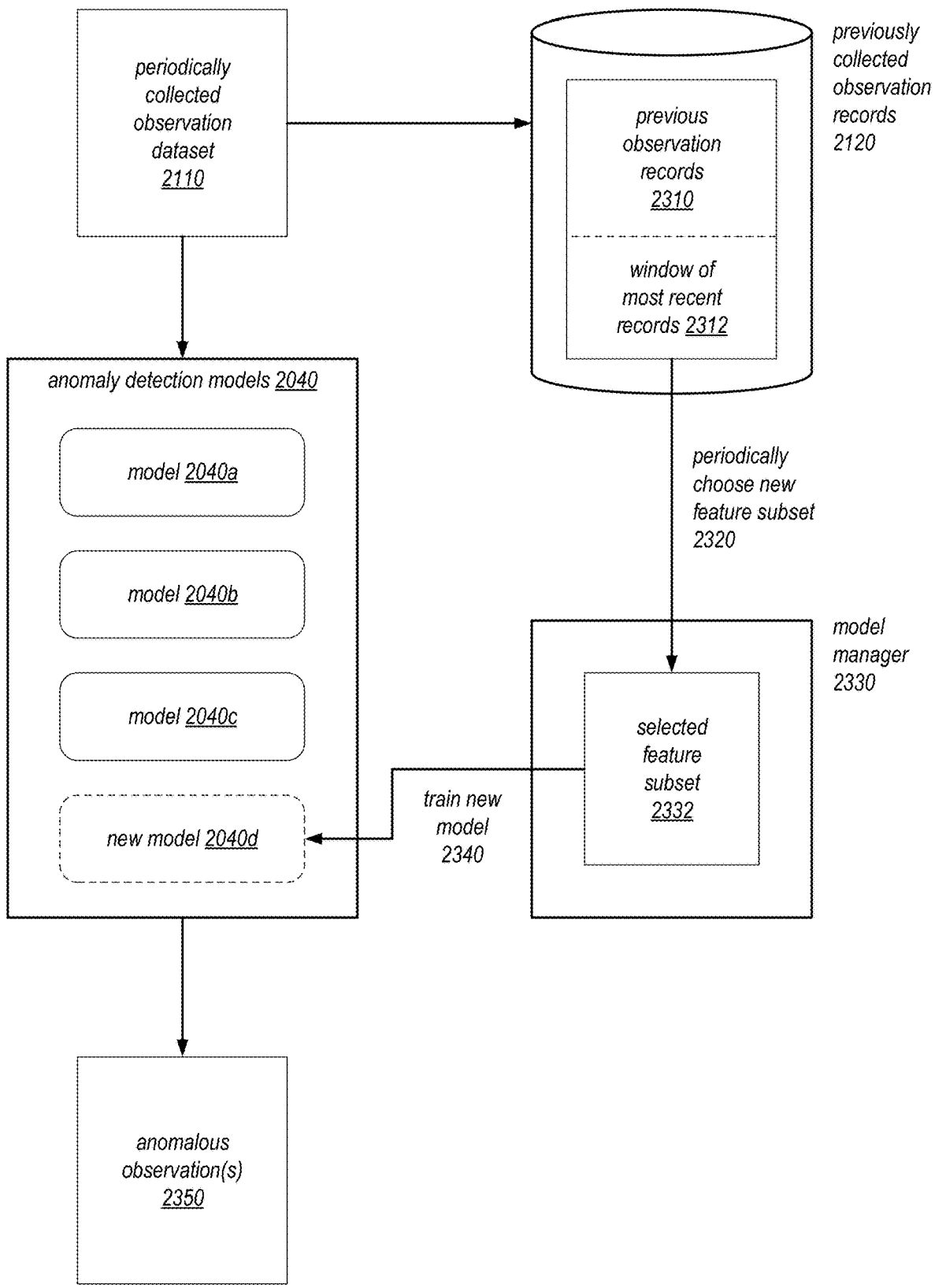
FIG. 23 illustrates a periodic feature selection process to select features for training new models in the machine learning anomaly detection system, according to some embodiments.

FIG. 23 illustrates a periodic feature selection process to select features for training new models in the machine learning anomaly detection system, according to some embodiments. In some embodiments, the model manager 2330 shown in the figure may implement the dimensionality reduction process discussed in connection with FIG. 5 or 6 to select features used to train the anomaly detection models 2040.

As discussed, in some embodiments, the anomaly detection pipeline 2000 receives periodically collected observation datasets 2110 to be analyzed for anomalies. The periodically collected dataset 2110 may include records of observed processes or hosts, for example, as shown in FIGS. 2A and 2B. As discussed, the anomaly detection pipeline is configured to analyze the collected dataset using a set of anomaly detection models 2040 to identify anomalous or outlier observation records 2350, which may be flagged and provided to human analysts for further investigation.

As shown, in some embodiments, the newly collected records are stored in a data store or repository 2120 of previously collected observation records (e.g., a database, a file system, or the like). The observation records repository 2120 may store observation records 2310 for many cycles of previously collected datasets. In some embodiments, a model manager 2330 periodically analyzes a window of the most recent observation records 2312 in the repository to choose 2320 a new subset of features 2332. To select the subset, the model manager may perform the process shown in FIG. 5 or 6, which selects the individual features based on a feature variability metric calculated for the features in the window 2312. The selected feature subset 2332 may then be used by the model manager to train 2340 a new anomaly detection model 2040d for the anomaly detection pipeline.

As shown in this example, the new model 2040d is added to the set of anomaly detection models 2040 maintained by the pipeline. In some embodiments, the model manager 2330 may be responsible for managing these model 2040, including the adding and removing models from the model set. Depending on the embodiment, an anomaly detection model may be removed from the model set 2040 if it grows too old, if its performance degrades unacceptably, or if its results deviate excessively from the other models in the model set. The model manager 2330 may add a new model 2040d to replace an older model. In some embodiments, the model manager 2330 may choose a new feature subset 570 for each new model 2040d that is created for the model set 2040. Accordingly, the models in the model set 2040 may be trained to look for anomalies based on different subset of features. In some embodiments, a new feature selection 2320 may be triggered based on different types of detected conditions, for example, when a sufficiently large number of new observation records have been added to the observation records repository 2120. Using this process, the model manager 2330 is able to automatically evolve the model set 2040 to focus on the most useful features in the observation data.

Figure 24:
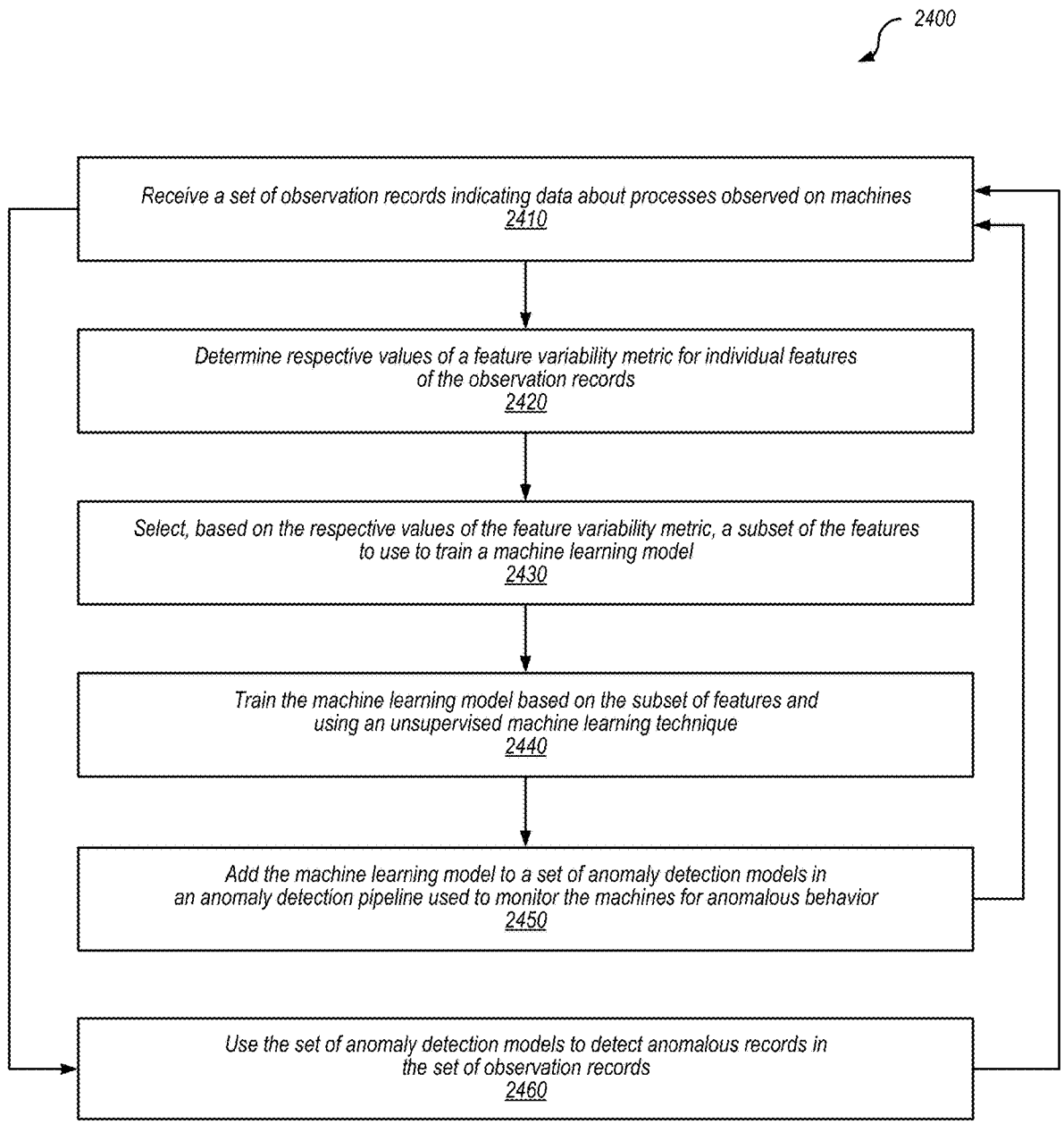
FIG. 24 is a flowchart 2400 illustrating an automated dimensionality reduction process used by a machine learning anomaly detection system to select features to train anomaly detection models, according to some embodiments.

FIG. 24 is a flowchart 2400 illustrating an automated dimensionality reduction process used by a machine learning anomaly detection system to select features to train anomaly detection models, according to some embodiments. The depicted process may be performed by an embodiment of a machine learning anomaly detection system, as shown for example in FIGS. 31 and 32.

As shown, at operation 2410, a set of observation records indicating data about processes observed on a set of machines is received. For example, the set of observation records may be the dataset 510 of FIG. 5 or dataset 610 of FIG. 6. In some embodiments, the dataset may be encoded as a matrix, which may include rows of process observation records (e.g. matrix 210 of FIG. 2A), or rows of host observation records (e.g. matrix 250 of FIG. 2B). The dataset may be collected periodically from the set of machines by a cyberattack monitoring system, which is configured to monitor the machines for signals of possible attacks.

At operation 2420, respective values of a feature variability metric are determined for individual features of the observation records. In some embodiments, operation 2420 may be performed by an embodiment of the feature variability metric calculator 540 discussed in connection with FIG. 5. The feature variability metric may provide a measure of how variable or dispersed a feature is in terms of its observed values. In some embodiments, the feature variability metric may be the standard deviation or variance of the feature with respect to a mean value of the feature. In some embodiments where the feature consists of a single bit, the feature variability metric may indicate an expected value of the bit. In some embodiments where the feature is a bit string, the feature variability metric may be a variance or standard deviation of a distance between the observed instances of the bit string in the dataset and a "mean" value of the bit strings. In some embodiments, to determine the distance between the mean value and the observed bit strings, a Euclidean distance or Hamming distance may be used. In some embodiments, the feature variability metric of individual features may be normalized to account for different value ranges or encodings of the features, so that the metric values of different features can be readily compared.

At operation 2430, a subset of the features is selected to train a machine learning model. The selection is performed based on the values of the feature variability metric for the different features. Operation 2430 may be performed by an embodiment of the feature selector 560, as discussed in connection with FIG. 5. In some embodiments, the feature variability metric values of all features are ranked, and a specified number of the highest or lowest ranked features (e.g. features with the smallest value dispersion) are selected for the subset. In some embodiments, a configured threshold may be used, so that only features with metric values below the threshold are included in the subset. In some embodiments, the selection process may take into account other factors in addition to the feature variability metric. In some embodiments, the selection may be performed based on a randomized factor, so that different feature selections are possible based on the same set of selection factors.

At operation 2440, the machine learning model is trained based on the subset of features selected and using an unsupervised machine learning technique. The machine learning model may be, for example, an anomaly detection model used by the anomaly detection pipeline 2000 as discussed in connection with FIG. 20. In some embodiments, operation 2440 may be performed by components such as the model manager 2330 of FIG. 23.

At operation 2450, the trained machine learning model is added to a set of anomaly detection models in the anomaly detection pipeline. As discussed, in some embodiments, the anomaly detection pipeline may maintain a set of anomaly detection models (e.g. models 2040 of FIG. 23) to detect anomalies in the behavior of monitored machines. The pipeline may employ a model manager (e.g. model manager 2330 of FIG. 23) to manage the models, for example, to add new models to the model set when needed. In some embodiments, whenever a new model is trained for the pipeline's model set, the model manager will perform the feature selection process to select the features for training the new model. In some embodiments, this selection process may be performed automatically and without any human intervention. As shown, the process may be repeated periodically, triggered by the receipt of new observation datasets. In this manner, the described process produces a dynamic model set that automatically adapts to the changing nature of the observation data.

As shown, process 2400 implements a second process loop where the set of anomaly detection models are periodically used 2460 to detect anomalous records in a new set of observation records. As discussed, the anomaly detection pipeline may be used to examine periodically collected observation datasets about machine processes, and identify suspicious outliers or anomalies in the datasets for human review. The execution of the anomaly detection models and the training of new models can occur independently as different subprocesses and based on different triggering events.

9. Example Systems and Methods for Generating Useful Synthetic Anomalies

Machine-learned anomaly detection is a valuable approach for a variety of cybersecurity applications (e.g., identifying unusual traffic, atypical usage of known applications, and the like). However, applying existing or traditional machine learning methods to anomaly detection in cybersecurity is hampered by the lack of labeled anomaly data signals indicative of the wide variety of attack strategies used by attackers. Such data is needed to train or test robust anomaly detection models.

One method to address the lack of truth data is to create synthetic data as a proxy. However, randomly generating synthetic data results in a distribution across the feature space that is uniform, and not at all representative of actual data that may be observed for real-world software processes seen on computing hosts. Moreover, such real-world data is typically very high-dimensional and sparse, making feature space coverage a significant problem with synthetic data generation.

Therefore, to address these technology-related challenges of simulating useful synthetic data in a high-dimensional feature space (e.g., a feature space for managed detection and response (MDR) process data), disclosed herein are methods, systems, and processes of generating synthetic data that preferentially samples points near the lower dimensional manifold where the real data lies. It will be appreciated that this approach may be used to create synthetic data that represents a more realistic set of synthetic data points than conventional synthetic data generation techniques.

As noted, in a high dimensional feature space, sampling in a hyper-cube uniformly across all dimensions results in data that is "far" (e.g., from the density point of view) from the manifold on which the real data is observed. This presents a technological problem to security analysts who would like to train machine learning models to detect anomalies. Security analysts would benefit from simulating anomalies that are closer to the manifold where the real data lies. Therefore, in some embodiments, a synthetic data generator is provided to bootstrap from the real data to create synthetic data that contain qualitative anomalies, which are close to the real data as evaluated based on a density function.

In some embodiments, a synthetic data generation process may be implemented to perform at least the following steps: (1) compute the boundary of an observed dataset in a high-dimensional space, with the goal of generating a synthetic dataset that lies near the boundary according to a density function of the observed dataset; (2) generate a candidate synthetic data point using a randomly sampled data point from the observed dataset (e.g., using the formula $Y=X+\rho \cdot W$, wherein X is the observed data point, $\rho$ is a distance or step size from X, and W is a unit step in the hypersphere surrounding X); (3) decide whether to keep the candidate data point using the density function (e.g., by generating a random number between 0 and 1 and checking if random number is less than the output of the density function at Y. This process may be performed for a fixed value of $\rho$ and repeated for multiple directions W. Alternatively, this process may be performed for a fixed direction W for different values of $\rho$. For example, the process may start from a distance $\rho=0$, and increase the distance until the density falls below a specified threshold (e.g. a desired boundary or density level of the observed dataset).

In some embodiments, another synthetic data generation process may be implemented to perform at least the following steps: (1) fit a density function $\hat{\psi}$ that evaluates a likelihood of being sampled from the manifold of a dataset of real data; (2) estimate a first distance from an observed data point using $\hat{\psi}$ that corresponds to a percentile (e.g. 5th percentile) of the output of this function ("delta 1"); (3) repeat steps (1) and (2) for a dataset of uniformly sampled data to estimate a second distance from the observed data point that corresponds to a percentile (e.g. 95th percentile) of the output of the second function ("delta 2"), (4) divide the separation between the two distances, delta 1 and delta 2, into equal intervals, (5) estimate the changes in distance that provides uniform steps of changes in density (e.g., by sampling a number of synthetic data points between the two distances to determine how the density function(s) are changing with the distance); and (6) using the estimated distances, generate synthetic data points between delta 1 and delta 2 until a desired synthetic data points at each density level is obtained. In this manner, the foregoing process provides a way of generating a set of synthetic data points that are likely to be uniformly stratified near the desired boundaries of the observed data.

Figure 25:
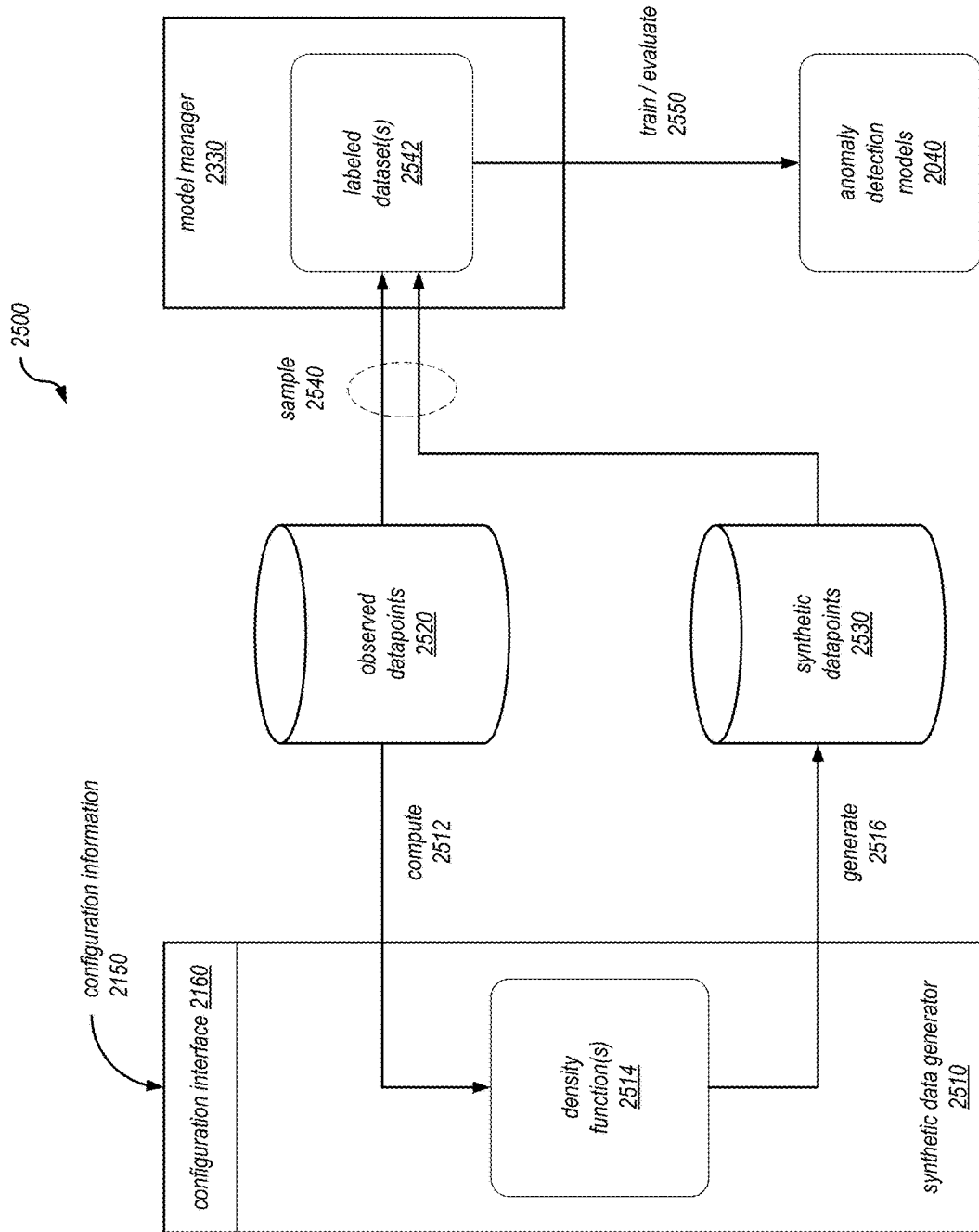
FIG. 25 is a block diagram 2500 illustrating the operations of a synthetic data generation system used in a machine learning anomaly detection system to generate synthetic data for machine learning models, according to some embodiments.

FIG. 25 is a block diagram 2500 illustrating the operations of a synthetic data generation system used in a machine learning anomaly detection system to generate synthetic data for machine learning models, according to some embodiments. In some embodiments, the synthetic data generator 2510 shown in the figure may be used to carry out the synthetic data generation process discussed in connection with FIG. 10.

As shown, in some embodiments, the synthetic data generator 2510 is configured to access a repository of observed data points 2520. In some embodiments, these observed data points may represent feature vectors that were actually extracted from observation records by the anomaly detection system. In some embodiments, the synthetic data generator 2510 may be configured to periodically access the observed data points repository to generate synthetic data points into a synthetic data points repository 2530. In some embodiments, the repositories 2520 and 2530 may be implemented as the same repository (e.g. a single database or dataset). In some embodiments, the repositories 2520 and/or 2530 may be the observed data repository 2120 discussed in connection with FIG. 21. In some embodiments, the synthetic data generator 2510 may be configured to augment observed data with generated synthetic data, for example, by appending generated synthetic data points to the same file containing the observed data points.

As shown, the synthetic data generator 2510 may periodically compute 2512 one or more density functions 2514 from the observed data. In some embodiments, the density function 2514 may be estimated for only a recent time window of the observed data. In some embodiments, multiple density functions may be generated, for example, for different clusters or categories of data seen in the observed data points. The density function(s) 2514 are then used to generate 2516 a population of synthetic data points, in the manner as discussed in connection with FIG. 10.

As shown, in some embodiments, the synthetic data generator 2510 may provide portions of the configuration interface 2160, which may be an interactive interface such as a GUI, or a programmatic interface such as an API or a service interface. The configuration interface 2160 may allow users or other programs to specify configuration information 2150 to control various operational aspects of the synthetic data generator. For example, the configuration information may specify how often (or under what conditions) the synthetic data generator should generate synthetic data. In some embodiments, the configuration information may indicate how to determine the density function. or how to sample the observed data points to generate synthetic data. In some embodiments, the configuration information may specify preferred directions or distances for generating synthetic data points. In some embodiments, the configuration information may specify constraints for generating synthetic data, such as density function probability bounds, the proportions or amount of data points to generate in different ranges, among other types of constraints.

As shown, in some embodiments, the model manager 2330 is implemented to consume the data stored in the observed data points repository 2520 and the synthetic data points repository 2530. In some embodiments, the model manager 2330 is configured to perform ongoing training, updating, and/or testing of one or more of the anomaly detection models 2040 used by the anomaly detection pipeline 2000. As shown in this example, the model manager 2330 periodically samples 2540 from the two data point repositories 2520 and 2530 to create labeled datasets 2542. In some embodiments, the model manager 2330 may automatically label the data points according to whether they are observed or synthetically generated. In some embodiments, the labeling may be performed based on other features of the data points. As shown, after the labeled dataset(s) 2542 are created, the model manager may use the dataset(s) to train or evaluate 2550 the anomaly detection models 2040. For example, the training of these models may be performed as discussed in connection with FIG. 9.

Figure 26:
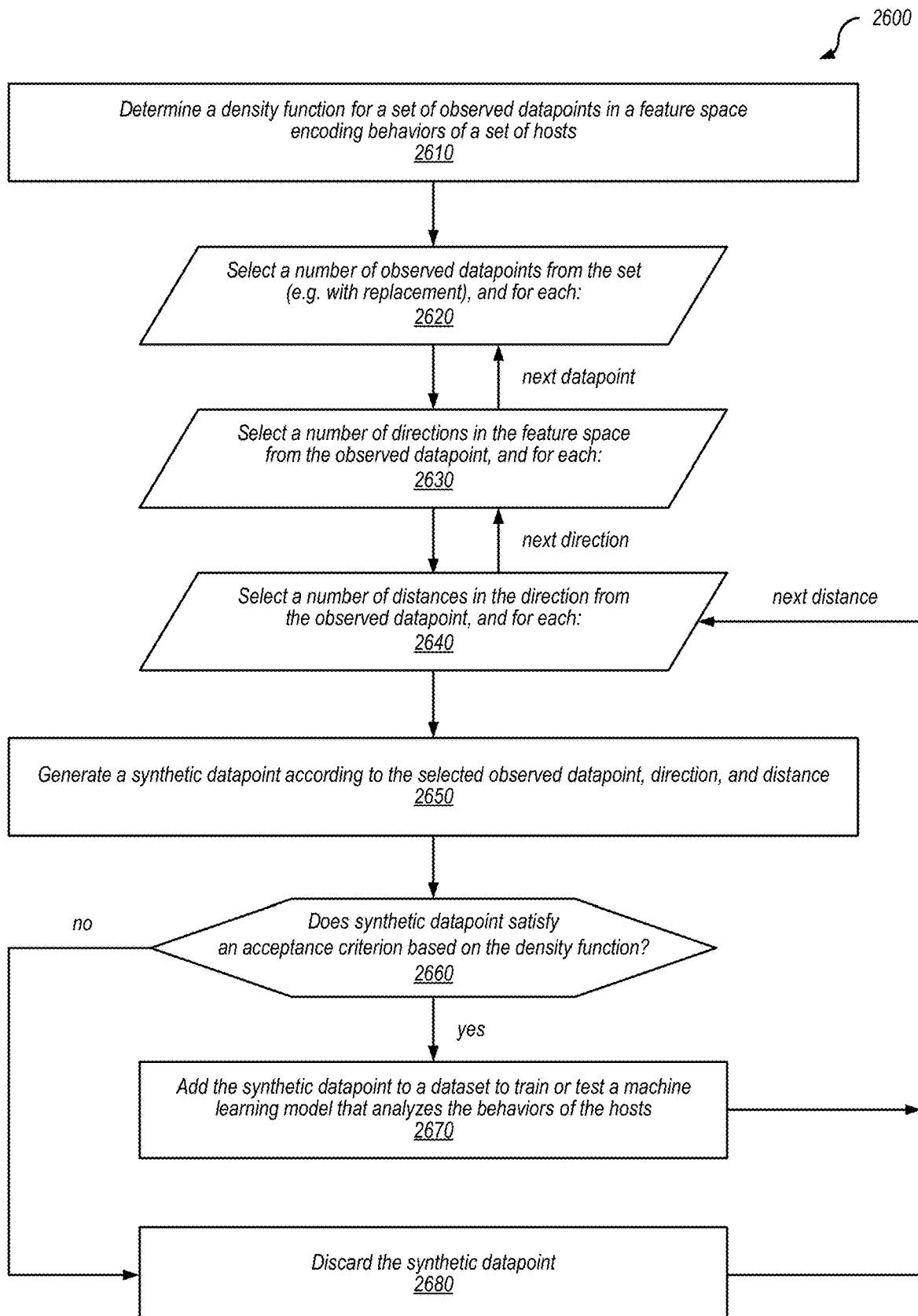
FIG. 26 is a flow chart 2600 illustrating a process performed by a synthetic data generation system to generate synthetic data used to train or test machine learning models in an anomaly detection system, according to some embodiments.

FIG. 26 is a flow chart 2600 illustrating a process performed by a synthetic data generation system to generate synthetic data to train or test machine learning models in an anomaly detection system, according to some embodiments. In some embodiments, the process shown may be performed by a synthetic data generator, such as the synthetic data generator 2510 of FIG. 25.

At operation 2610, a density function is determined for a set of observed data points in a feature space (e.g. feature space 1000 of FIG. 10). In some embodiments, the observed data points may encode behaviors of a set of hosts, for example, feature vectors of processes or hosts that are used to train a machine learning model used by an anomaly detection system (e.g. the ML models 2040 of FIG. 20). In some embodiments, the density function may be determined using a density estimation technique such as a Kernel Density Estimator with Gaussian kernels. The density function may be used to determine, for any given data point in the feature space, a probability that the data point will be observed or sampled in the dataset.

At operation 2620, a number of observation data points are selected from the set. In some embodiments, the observed data points may be selected with replacement, meaning that the same data point may be selected more than once. In some embodiments, the observation data points may be selected randomly. In some embodiments, the observation data points may be selected using one or more selection criteria (e.g. based on its feature values), which may be controlled via configuration information provided to the system.

As shown, operation 2630 is performed for each observation data point selected. At operation 2630, a number of directions in the feature space are selected from a particular observation point. The direction will be used to generate one or more synthetic data points in the feature space. In some embodiments, the selected direction may be a feature in the feature vector of the observed data point. In some embodiments, the selected direction may be some linear combination of multiple features in the feature vector (e.g., a selected unit vector in the hypersphere around the observed data point). In some embodiments, the direction may be selected randomly. In some embodiments, the direction may be selected based on configuration information specified for the system (e.g. based on the location of the observed data point relative to the rest of the observed data points).

As shown, operation 2640 is performed for each direction selected in operation 2630. At operation 2640, a number of distances are selected in the direction from the observed data point. In some embodiments, the distance may be selected at random. In some embodiments, the distances may be constrained by configuration information, for example, to limit the distances to a particular distance range. In some embodiments, the configuration information may specify a probability range, which can be used to calculate the distance range using the density function.

In some embodiments, the range may be bounded by a first probability value calculated using a first density function and a second probability value calculated using a second density function. For example, the distance range for a particular direction may be bounded by the 5th percentile probability of a first density function of the observed dataset, and the 95th percentile probability of a second density function of a dataset of randomly generated synthetic data. In some embodiments, after a distance range is determined, a logistic regression may be performed to estimate the relationship between the distance and one or both of the density functions (e.g. as shown in FIG. 11B). Using this determined relationship, successive synthetic data points of increasing distance values may be generated in such a manner that each data point corresponds to a uniform decrease in the density function probability value.

As shown, operation 2650 is performed for each distance selected. At operation 2650, a synthetic data point (e.g. synthetic data point 1050 of FIG. 10) is generated according to the selected observed data point, the selected direction, and the selected distance. Thus, operations 2620, 2630, 2640, and 2650 may be repeated to generate a large number of synthetic data points in the feature space. In some embodiments, the process may successive synthetic data points in a particular direction at increasing distances. The generation of the successive data point will continue until the density function probability of a data point falls between a specific interval or below a specified threshold. Though not shown here, in some embodiments, the synthetic data point generation process may first select a particular distance, and then select multiple directions with that distance to generate synthetic data points. In some embodiments, synthetic data points may be generated with a randomly drawn pair of a direction and a distance.

At operation 2660, a check is performed to determine whether the generated synthetic data point satisfies an acceptance criterion based on the density function. For example, in some embodiments, the acceptance criterion may require that the synthetic data points have a density function probability value that is above or below a certain configured threshold or within a configured range. In some embodiments, the acceptance criterion may include a random component. For example, a synthetic data point may be accepted if its density function probability is more than a randomly generated value between 0 and 1.

If the synthetic data point satisfies the acceptance criterion, the process proceeds to operation 2670, where the data point is added to a dataset that is used to train or test a machine learning model that is used to analyze the behaviors of the hosts. For example, the machine learning model may be a classification model discussed in connection with FIG. 9. In some embodiments, the generated synthetic data points may be combined with actual observed data points in a single dataset (e.g. dataset 2542 of FIG. 25), where the data points are automatically labeled to indicate whether they are observed or synthetic. In some embodiments, such a dataset may be used to train a classification model to distinguish between observed data points and synthetic data points. In some embodiments, the dataset may also be used as validation or testing data for the classification model.

If the synthetic data point does not satisfy the acceptance criterion, the process proceeds to operation 2680, where the synthetic data point is discarded. In some embodiments, generated data points may be discarded for reasons other than their density function value. For example, in some embodiments, the system may discard synthetic data points if it is determined that too many synthetic data points have been generated in a vicinity of the feature space. In some embodiments, the illustrated process may repeat until a sufficient number of synthetic data points have been generated.

10. Example Systems and Methods for Evaluating a Model by Generating Patterns, Perturbing Patterns, and Injecting Anomalies Anomaly detection applied to managed detection and recovery (MDR) hunt data is a valuable tool for identifying previously unseen types of malicious behavior. Unfortunately, existing algorithms and methodologies are difficult to test quantitatively because they deal with scenarios where labeled ground truth does not exist. Accordingly, in some embodiments of an anomaly detection system, an anomaly detection model evaluator is used to implement methods, systems, and processes to test the robustness of machine learning models in scenarios most commonly found in MDR hunt data. Hunts analyze individual computing assets and collect data about the software or computing processes running or executing on the computing assets. To obtain benchmarks for acceptable, adequate, or optimized performance in this context, test cases corresponding to the presence of an unusual process, unusual combination or processes, and robustness to noise are generated for analysis.

In some embodiments, the model evaluator may be configured to perform at least the following functions: (1) access detected/found anomalies, (2) evaluate how sensitive the outlier detection models are to detecting said anomalies, and (3) evaluate or determine how robust the models were in cutting through noise to find the anomalies.

In certain embodiments, the model evaluator simulates different scenarios by generating synthetic observation records in a matrix of n rows (observations) and k columns (features). In some embodiments, in a first scenario, a particular column is zero across all rows, except the anomaly row where it is one. In some embodiments, the test dataset 1210 shown in FIG. 12 may be used to simulate the first scenario. In some embodiments, in a second scenario, there is a fixed number of patterns that are preset (e.g., bit pattern 0111000), and the anomaly is a row that is not compatible with the preset patterns. In some embodiments, the test dataset 1310 of FIG. 13 may be used to simulate the second scenario. In some embodiments, in a third scenario, uncertainty is added to the test data by changing the features values (e.g. flipping bits) within preset patterns. Using this scenario, the model is tested for robustness to noise. In some embodiments, the test dataset 1410 of FIG. 14 may be used to simulate the second scenario. In some embodiments, the false positive rate of a model can be tested by not adding any anomalies to a test dataset in a fourth type of simulated scenario, and determining what anomalies the model identifies.

As noted, and in some embodiments, these simulated scenarios can be combined for more rigorous testing and evaluation of the anomaly detection models. In certain embodiments, the anomaly detection pipeline or model can be modified, trained, evaluated, or tested using mixed scenario analysis, model aggregation analysis, and/or anomaly distance analysis to determine the individual and collective performance of various models and other methodologies implemented by the pipeline and reduce potentially reduce the computational complexity of the pipeline.

The mixed scenario analysis may be used to evaluate the performance of the models with data generated with combinations of scenarios and parameters, as noted above. With each list of different scenarios applied to the models, a variable may be outputted for each model, where 1 means a model detected the anomaly and 0 means that the anomaly was not detected. By creating a sampling across many different combinations of scenarios, in certain embodiments, a regression can be run to determine which elements lead to better detection of anomalies.

In the model aggregation analysis, multiple models are analyzed together across a fixed number of scenarios. In some cases, the goal is to determine if and which models are able to identify the same anomalies in a given scenario, thereby allowing the anomaly detection system to generate a confidence value based on the findings of individual models in the ensemble (e.g., when greater than a threshold of models are identifying the same anomalies).

In the anomaly distance analysis, the effects of distances of anomalies from normal data on the models' abilities to detect those anomalies are examined. For example, the analysis may reveal that a greater distance of the anomaly increases the chances of identifying the anomaly. In some embodiments, the anomaly distance may be an additional feature that can be varied in the base case analysis, as discussed in connection with FIG. 15.

Figure 27:
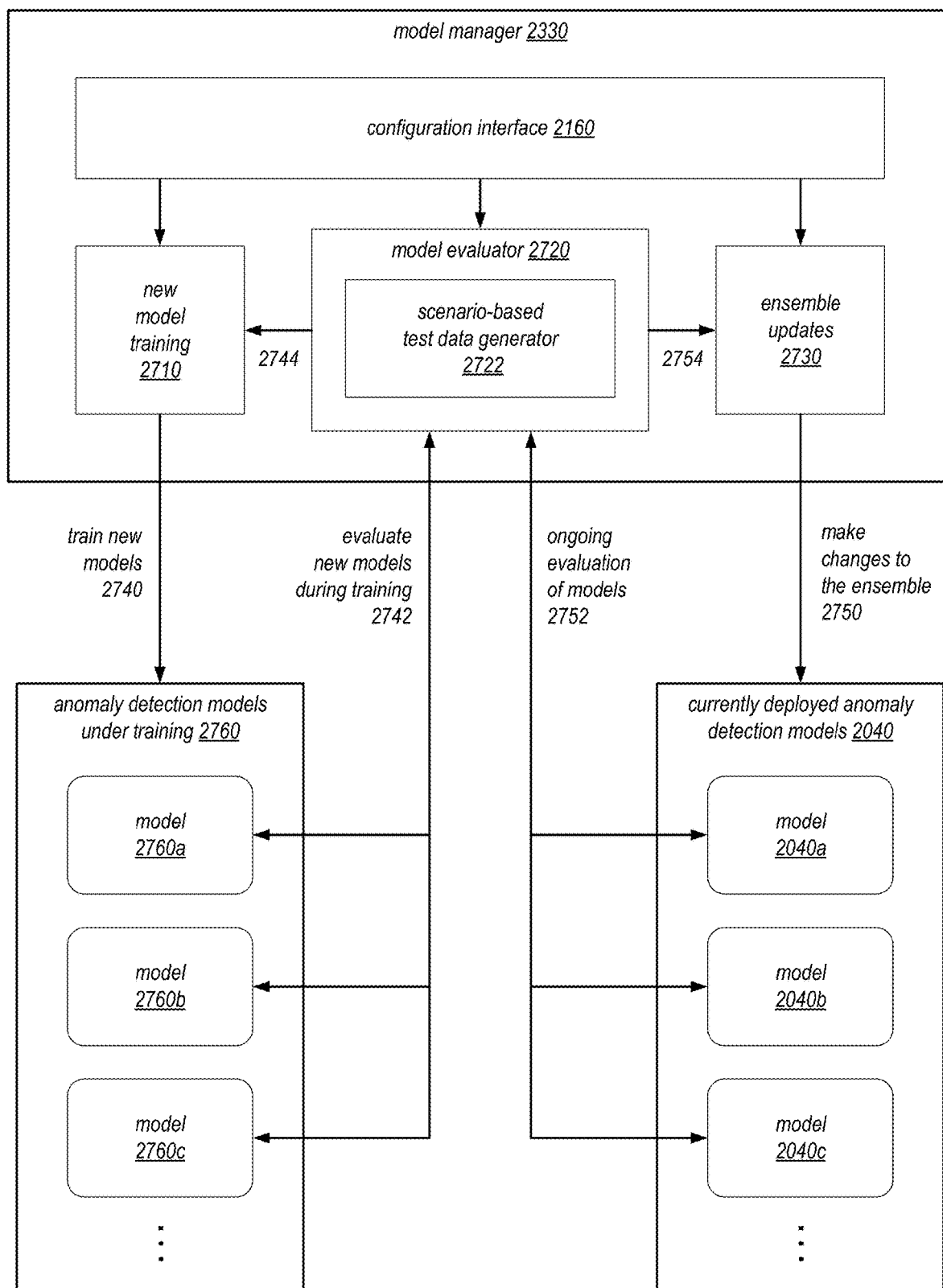
FIG. 27 is a block diagram illustrating a model evaluator that employs scenario-based test data generation to test anomaly detection models in a machine learning anomaly detection system, according to some embodiments.

FIG. 27 is a block diagram illustrating a model evaluator that employs scenario-based test data generation to test anomaly detection models in a machine learning anomaly detection system, according to some embodiments.

The figure depicts an embodiment of the model manager 2330 in the anomaly detection pipeline 2000. As shown, the model manager 2330 in this example implements a number of components, including a new model training component 2710, a model evaluator component 2720, a model ensemble updater component 2730, and the configuration interface 2160 that may be used to configure the operations of these components.

As shown, the new model training component 2710 is configured to train 2740 new models for the anomaly detection pipeline 2000. In some embodiments, the pipeline may maintain a set of the anomaly detection models 2760a-c that is being actively trained by the pipeline, as discussed in connection with FIG. 21. In some embodiments, the pipeline may continuously train new models based on newly observed data and periodically replace existing anomaly detection model 2040 with the new models.

As shown, during the training of the new models, the models may be periodically evaluated 2742 by the model evaluator 2720. For example, in some machine learning processes, a model under training may be tested to see if it meets an accuracy criterion. If the model satisfies the accuracy criterion, the training may be stopped or advanced to a next stage. To perform this testing, the model evaluator 2720 in this example uses a scenario-based test data generator 2722 to generate synthetic test dataset for the testing. This test data generator 2722 may generate test datasets that simulate scenarios of actual anomalies, such as the scenarios discussed in connection with FIGS. 12-15. In some embodiments, generated test datasets may be stored in a test data repository for repeated use, so that a model's performance changes can be tracked during the course of training. The model evaluator 2720 may perform the model test using the generated test data and then report the model's performance results 2744 to the new model training component 2710, so that the model training component can make further decisions about the course of model training. For example, in some embodiments, the new model training component 2710 may choose a next training dataset based on a determined weakness of the model for a particular data scenario. In some embodiments, the configuration interface 2160 may be used to control various aspects of how the test scenarios are generated by the model evaluator 2720, and/or how the new model trainer 2710 will adjust model training based on the model's performance results.

As shown, the ensemble updater component 2730 is configured to make periodic change 2750 to the set of currently deployed anomaly detection models 2040 used by the anomaly detection pipeline 2000. For example, the ensemble updater 2730 may periodically add new models to the ensemble or remove models from the ensemble based on the models ongoing performance, as discussed in connection with FIG. 23.

Figure 16:
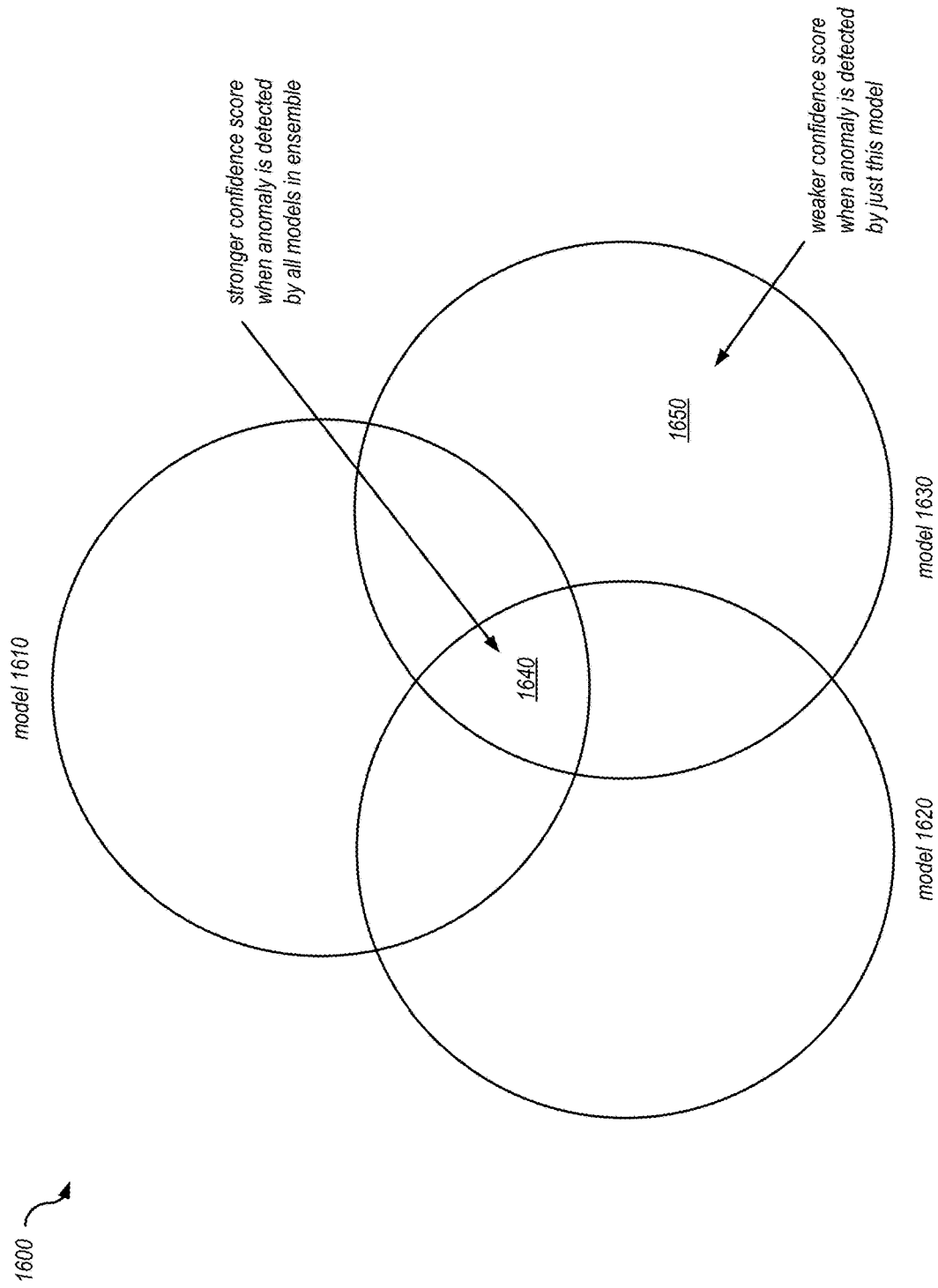
FIG. 16 is an illustration 1600 of a model aggregation analysis performed using synthetic data to evaluate models in a machine learning anomaly detection system, according to some embodiments.

As shown in this example, the model evaluator 2720 is used to perform ongoing evaluation 2752 of the deployed models. The model evaluator 2720 may periodically generate new test datasets to conduct the testing 2752, such as test datasets that simulate scenarios of anomalies seen in recent observation data collected from client networks. In some embodiments, a core set of basic test datasets may be maintained by the evaluator and used repeatedly over time to enforce a minimal standard of the ensemble's performance. For example, one basic test may require that the deployed models are able to detect anomalies in a particular set of process or machine features. Depending on the embodiment and/or the configuration, some of the tests may be directed to individual models, while other tests may be directed to the ensemble as a whole (e.g. using a model aggregation analysis discussed in connection with FIG. 16). As shown, the model evaluator 2720 may report the models performance results 2754 to the ensemble updates component 2730, which will use the results to determine how the ensemble should be changed. For example, under some circumstances, the updater may elect to replace a particular deployed model 2040a with one or more new models 2760b, in order to improve the ensemble's performance for a particular anomaly scenario. In some embodiments, such automated actions by the ensemble updater component 2730 may be controlled by rules specified via the configuration interface 2160.

Figure 28:
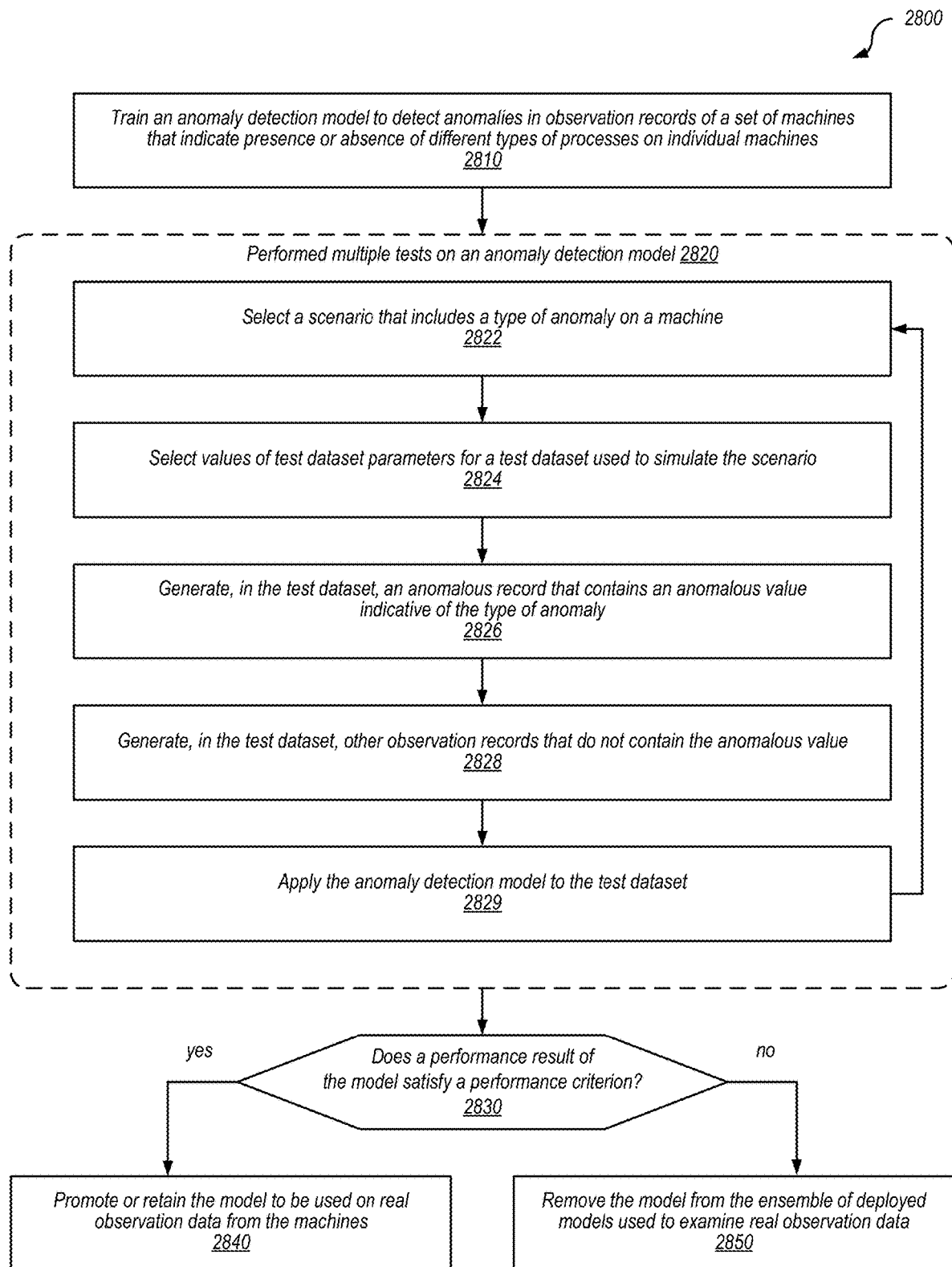
FIG. 28 is a flow chart 2800 illustrating a process performed by a scenario-based test data generation system to generate synthetic data scenarios to test machine learning models in an anomaly detection system, according to some embodiments.

FIG. 28 is a flow chart 2800 illustrating a process performed by a scenario-based test data generation system to generate synthetic data scenarios to test machine learning models in an anomaly detection system, according to some embodiments. The process 2800 may be performed by an embodiment of the anomaly detection pipeline 2000 of FIG. 20 or the model evaluator 2720 of FIG. 27.

At operation 2810, an anomaly detection model is trained to detect anomalies in observation records collected from a set of machines. The anomaly detection model may be one model in an ensemble of anomaly detection models 2040 maintained by the anomaly detection pipeline. In some embodiments, the observation records may be the observation data 2110 of FIG. 21. In some embodiments, each observation record may represent an individual machine and indicate the presence or absence of different types of processes on the individual machine, as discussed in connection with FIG. 2B. In some embodiments, the model may be trained periodically using new observation data collected from the machines, as discussed in connection with FIG. 21.

At operation 2820, multiple model tests are performed on the anomaly detection model. In some embodiments, the model tests may be performed during the course of model training to verify that the model is ready for deployment to the pipeline's working ensemble, as discussed in connection with FIG. 27. In some embodiments, the model may be retested periodically to determine whether the model may remain in the ensemble. As shown, the model test 2820 may be divided into a number of sub-operations.

At operation 2822, a test scenario is selected for test the model, which may include a type of anomaly on a machine. Depending on the embodiment, the scenario may be selected from the set of scenarios discussed in connection with FIGS. 12, 13, and 14. For example, a first type of scenario may be simulated by a test dataset (e.g. test dataset 1210) that includes an anomalous record (e.g. anomaly 1242) that indicates the presence of a particular type of process on the machine, and other observation records (e.g. normal data 1240) that indicates the absence of the particular type of process on other machines. For a second type of scenario, another test dataset (e.g. test dataset 1310) may be generated that includes an anomalous record (e.g. anomaly 1342) that indicates the presence of a combination of process types on the machine, and other observation records (e.g. normal data 1340) that do not indicate the combination of process types on other machines. In some embodiments, instead of a particular combination of process types, the anomaly record (e.g. anomaly 1342) may indicate a specific set of properties of a particular process type that are not seen in the normal observation records. In a third type of scenario, another test dataset (e.g. test dataset 1410) may be generated where some of the normal observation records (e.g. uncertainty rows 1420) are modified to randomly vary the anomalous feature (s) in the anomalous record. In some embodiments, a fourth type of scenario may be used where the generated test dataset does not include any anomalous records. This last type of scenario may be used to measure the false positive rate of the anomaly detection model. In some embodiments, a single generated test dataset may include multiple anomalous records. In some embodiments, a single test dataset may include multiple blocks of records that simulate different scenarios with different types of anomalies. Such a test dataset may be used to perform a mixed scenario analysis of the anomaly detection model, as discussed previously.

At operation 2824, the values of a number of test dataset parameters are selected for the test dataset used to simulate the scenario. In some embodiments, the selection process may be performed as discussed in connection with FIG. 15. The test dataset parameters may include the number observation records in the test dataset, the number of variable features in the test dataset, the number or proportion of anomalous records in the test dataset, and/or a distance metric that indicates how distinct the anomalous record (s) are from the normal observation records. In some embodiments where the test dataset is divided into multiple record blocks of different scenarios, each record block may be associated with a different set of test dataset parameters. In some embodiments, the test dataset parameter values may be selected randomly for each test run. In some embodiments, the parameter values may be configurable via a configuration interface (e.g. configuration interface 2160 of FIG. 27).

At operation 2826, an anomalous record is generated in the test dataset. The anomalous record will contain an anomalous value that is indicative of the type of anomaly associated with the scenario. For example, the anomaly may indicate the presence or absence of a particular type of process on a machine. As another example, the anomaly may be a particular pattern of observed process types on a machine. As yet another example, the anomaly may be a pattern of properties observed for a particular type of process. Depending on the embodiment, the anomalous value may be a single bit, a sequence of bits, a continuous value, or a vector of continuous values. In some embodiments, the anomalous value may be generated using one or more randomization techniques. In some embodiments, the anomalous value may be generated based on one or more previous observation records archived by the anomaly detection pipeline. For example, the anomalous record may be generated using the synthetic data point generation technique discussed in connection with FIG. 10.

At operation 2828, other observation records are generated in the test dataset that do not contain the anomalous value. These other observation records may be generated to simulate normal observations in the test dataset. As with the anomaly record (s), the normal observation records may be generated using a randomization technique, based on previous observation records, or both. In some embodiments, each normal observation record may be generated from a sample of actual observation records previously collected by the pipeline. In some embodiments, the size of the different groups of normal observation records may depend on how common the actual observation record was in the collected data. In some embodiments, some degree of random noise may be injected into some portion of the normal observation records, as discussed in connection with FIG. 14.

At operation 2829, the anomaly detection model is applied to the generated test dataset to determine the anomalies in the test dataset. In some embodiments, the findings of the anomaly detection model will be checked to see whether the model was able to identify the synthetic anomaly record(s) added to in the test dataset. If the model was able to detect the anomaly, the performance result of the model will note the successful detection. In some embodiments, if the model identified one or more normal records as anomalies, the performance result of the model will also be updated to note the false positives. In some embodiments, outlier metrics or confidence values assigned by the model to individual observation records will also be taken into account in the model performance result. In some embodiments, all model performance metrics will be combined based on a formula to produce a single model performance score for the test dataset. As shown, in some embodiments, the testing process 2820 may be repeated many times for a given model, based on many generated test datasets. In some embodiments, an expected value or a standard deviation of the model performance result may be calculated across the multiple tests. In some embodiments, a regression analysis may be performed to determine how the model's performance changes with one or more o test parameters. In some embodiments, the suite of tests that are used for a given model may be configurable via the configuration interface 2160 of the model manager.

At operation 2830, an evaluation of the anomaly detection model is made to determine whether the model's performance satisfies a performance criterion. In some embodiments, the model performance result may be an aggregated performance score obtained for all test datasets, and the performance criterion may be a minimum threshold for the aggregated score. In some embodiments, the model performance result may reflect multiple performance measures, and the criterion may include multiple pass-or-fail requirements for each performance measure. In some embodiments, the anomaly detection model may be one of many models in an ensemble maintained by the anomaly detection pipeline, and the entire ensemble of models may be evaluated collectively in a model aggregation analysis, as discussed in connection with FIG. 16. For example, in some embodiments, the performance criterion for an individual model may depend on the performance of other models in the ensemble. As another example, the performance criterion may require that a minimum number of models in the ensemble are able to identify a certain type of anomaly.

As shown, if the model's performance result satisfies the performance criterion, the process proceeds to operation 2840, where the model is promoted or retained for use on real observation data collected from the machines. For example, if the anomaly detection model is a model that is newly trained by the anomaly detection pipeline, a successful evaluation of the model will allow the model to be added to the pipeline's working ensemble. If the model is already deployed in the pipeline's ensemble, the successful test will allow the model to remain in the ensemble.

As shown, if the model's performance result does not satisfy the performance criterion, the process proceeds to operation 2850, where the model may be removed from the ensemble used by the pipeline. In this manner, the pipeline may continuously adjust the membership of its model ensemble to adapt the ensemble to the changing nature of the collected observation data. In some embodiments, a model removed from the ensemble may not be immediately deleted, but demoted to a group of offline models that are not used to analyze real observation data. The offline models may be retrained using newly collected data and reevaluated for a period of time. In some embodiments, if a model's performance sufficiently improves based on the additional training, it may be promoted back to the pipeline's working ensemble.

11. Example Systems and Methods for Providing an Interpretable Explanation for Feature Importance in Anomaly Detection When machine learning models are used to detect anomalies for human review, it is often beneficial to provide some amount of interpretive information to explain the models' results. For example, when the anomalies are provided to security analysts as suggestions of a possible security threat, it may be useful to also provide the underlying features in the observation data that caused an observation to be identified as an anomaly. In order to provide the security analyst with more information for the investigation, in some embodiments, an anomaly detection system may implement a model results interpreter (e.g. the model result interpreter 1900 of FIG. 19A) that quantifies the effect of different features on a detected anomaly's anomaly score.

In some embodiments, the model results interpreter 1900 examines one feature at a time by generating comparison observation records that isolates the effect of each feature. In some embodiments, the comparison record may retain the value of the examined feature while suppressing all other features. In some embodiments, the comparison record may vary the examined feature while keeping the other features of the original anomaly record. The anomaly detection model(s) are then executed on the comparison records to obtain new anomaly or outlier scores for the comparison records. When this process is repeated for each feature, the resulting set of anomaly scores provide(s) a way to quantitatively determine how much feature contributed to the anomaly record being identified as an anomaly. A security analyst can use this interpretive information to gain a deeper understanding of the detected anomaly, including which features were determinant for generating an alert on a detected anomaly. Such information may be used by the analyst as a starting point to begin his or her investigation.

In some embodiments, the model results interpreter 1900 may perform at least the following operational steps: (1) keep/maintain one feature of a detected anomaly observation and rerun or re-execute the anomaly detection pipeline to obtain a new anomaly score, and (2) repeat step (1) for each feature to obtain the set of anomaly scores for all features in the anomaly record. In some embodiments, the interpretive process may treat the set of features as independent. In some embodiments, a linear regression approach may be performed to fit a linear model to the aggregate anomaly score results, and report features with the highest coefficients.

Figure 29:
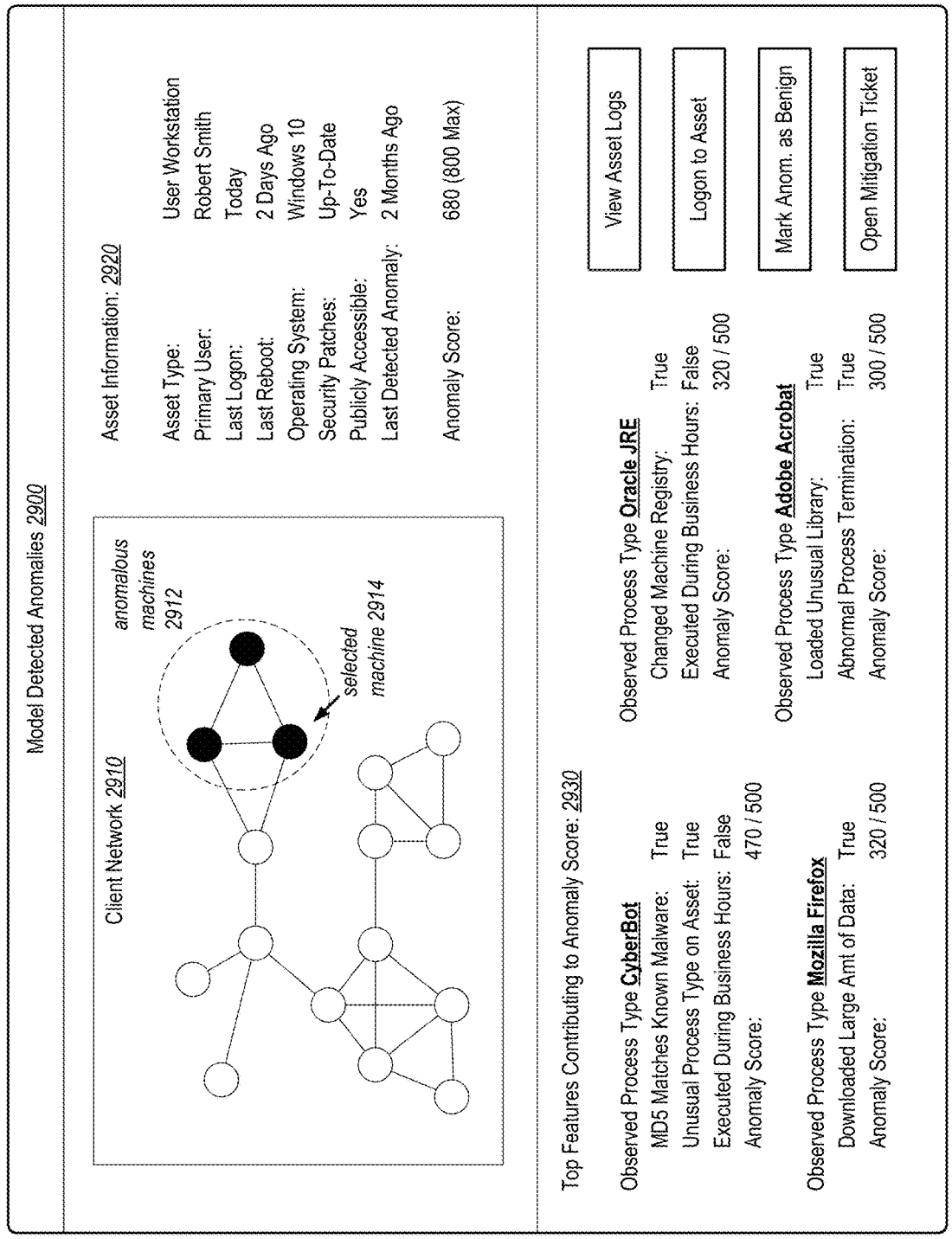
FIG. 29 illustrates a graphical user interface 2900 of a machine learning anomaly detection system that indicates anomalous machines detected in a client network and observed features that influenced an anomalous machine's anomaly score, according to some embodiments.

FIG. 29 illustrates a graphical user interface 2900 of a machine learning anomaly detection system that indicates anomalous machines detected in a client network and observed features that influenced an anomalous machine's anomaly score, according to some embodiments.

FIG. 29 depicts an example graphical interface GUI 2900 that shows anomalous machines 2912 detected by a machine learning anomaly detection system in a client network 2910. As discussed, in some embodiments, the machine learning anomaly detection system may periodically data about processes from machines in the client network 2910, and analyze the collected data using machine learning models to identify anomalous or outlier behavior in the network. Such anomalous behavior may then be surfaced (e.g. via the GUI 2900) to human analysts to investigate as possible signals of security threats. These threat hunting processes may be performed regularly on a client network, for example, once a week.

As shown in this example, three machines or assets in the client network 2910 are identified as anomalous machines for the observation period. In this example GUI, the user may select a machine in the client network graph to show additional details about the machine. In this example, information about the selected asset 2914 is shown in section 2920. Section 2920 shows an anomaly score of the selected machine 2914. In some embodiments, this anomaly score may be generated by machine learning models in the anomaly detection system, which may use the anomaly score to determine whether a given machine's behavior represents an anomaly.

As shown, the GUI 2900 also provides another section 2930, which provides model results interpretation information. In some embodiments, the interpretation information shown in the section 2930 may be generated by a model results interpreter (e.g. interpreter 1900 of FIG. 19A). As shown, the interpretation information first indicates a number of process types observed on the machine. In some embodiments, the model results interpreter may select these process types (e.g. features of the machine) using the techniques described in connection with FIG. 19A. For example, the process types shown in the section may be selected based on a computed influence metric that indicates how much they influenced the machine's anomaly score.

Additionally, section 2930 also shows features of each process type that had contributed to the process type being identified as an anomaly. In some embodiments, the displayed features (e.g. observed properties of each process type) may be selected based on the techniques discussed in connection with FIG. 19A. In some embodiments, the interpretive technique used by the anomaly detection system may be used to interpret the results of different types of anomaly detection models. For example, the same interpretive technique may be used for a first anomaly detection model used to identify machine anomalies and a second anomaly detection model used to identify anomalies within individual process types.

In some embodiments, a human analyst viewing the GUI 2900 may use the interpretation information to quickly begin investigating the detected anomalous assets for signs of security threats. For example, based on the information provided in section 2930, an analyst may check the process logs of asset 2914 for executions of CyberBot, which is a known type of malware. The analyst may also check various logs to determine what type of data was downloaded by MOZILLA FIREFOX processes, what registry entries were changed by ORACLE JRE processes, and what libraries were loaded by ADOBE ACROBAT processes. In some cases, the analyst may determine that the flagged anomalies are benign processes, and indicate his or her findings in the anomaly detection system. In other cases, the analyst may determine that the anomalies represent suspicious activity. If so, the analyst may open a mitigation ticket to perform more in-depth review, begin monitoring of the asset, or remedy any security issues on the asset.

Figure 30:
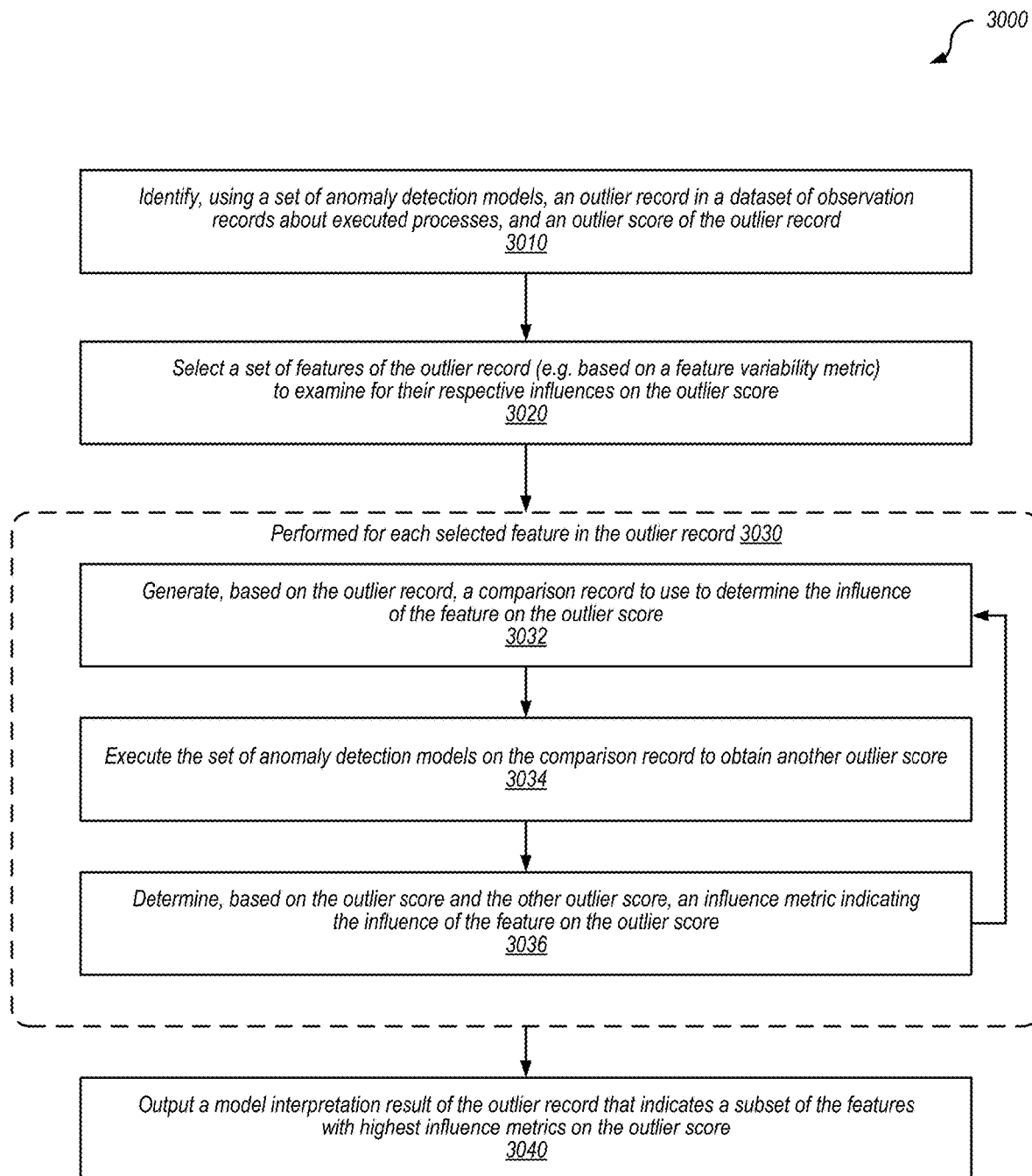
FIG. 30 is a flow chart 3000 illustrating a process performed by a model results interpreter that determines features of an outlier record that had high influence over the record's outlier score, according to some embodiments.

FIG. 30 is a flow chart 3000 illustrating a process performed by a model results interpreter that determines features of an outlier record that had high influence on the record's outlier score, according to some embodiments. Operations of the depicted process may be performed by embodiments of the model results interpreter 1900, as discussed in connection with FIG. 19A.

At operation 3010, an outlier record and an associated outlier score is identified in a dataset of observation records using a set of anomaly detection models. The observation records may be records about processes executed on one or more machines, such as the observation records discussed in connection with FIG. 2A or 2B. The anomaly detection model(s) may be one or more machine learning models maintained by an anomaly detection pipeline, such as the anomaly detection models 1930 of FIG. 19A. In some embodiments, the outlier record (s) may be identified based on their respective outlier scores (e.g., based on a ranking of their outlier scores).

At operation 3020, a set of features of the outlier record is selected to be examined for the respective influences on the outlier score. In some embodiments, all features of the outlier record may be examined. In other features, to shorten the execution time of the model result interpretation process, the set of examined features may be reduced. In some embodiments, the set of examined features may be selected based on a metric computed for individual features, such as the feature variability metric discussed in connection with FIG. 5.

As shown, operations 3032, 3034, and 3036 are performed 3030 for each selected feature in the outlier record. At operation 3032, a comparison record is generated based on the outlier record to be used to determine the influence of a feature on the outlier score. In some embodiments, the comparison record may be generated using the comparison record generator 1920 in FIG. 19A, and in the manner discussed in connection with FIG. 19B or 19C. In some embodiments, the comparison record may retain the examined feature from the outlier record, but suppress other features in the outlier record (e.g. by setting the other features to zero). In some embodiments, the comparison record may modify the examined record from the outlier record, but keep all other feature values the same. In some embodiments, the examined feature may be modified by computing one or more random values for the feature.

At operation 3034, the comparison record is provided as input to the set of anomaly detection models to determine a different outlier score. This other outlier score will be used to determine the influence of the examined feature on the outlier record's outlier score.

At operation 3036, an influence metric is determined for the feature based on the outlier score and the new outlier score computed for the comparison record. Operation 3036 may be performed by an embodiment of the score influence metric calculator 1940, as discussed in connection with FIG. 19A. In some embodiments, the new outlier scores for all examined features may be normalized to a common value range to determine the influence metric. In some embodiments, a difference between the original outlier metric and the new outlier metric is calculated, and the set all differences may then be normalized to obtain the influence metrics. In some embodiments, the influence metrics may be determined by fitting a linear model to estimate the outlier score based on the new outlier scores computed from all of the comparison records. In some embodiments, the determined coefficients of the linear model may be used as the influence metrics.

After influence metrics have been determined for each of the selected features in the outlier record, at operation 3040, a model result interpretation is generated for the outlier record. The model result interpretation may indicate a subset of the features of the outlier record that have the highest values for the influence metric. For example, the interpretation information may indicate a group of process types that caused a machine to be identified as an anomalous machine. As another example, the interpretation information may indicate a set of process properties that caused a type of process to be identified as an anomalous process type. In some embodiments, the model interpretation results may be provided along with the models' actual findings, for example, via a graphical user interface such as GUI 2900 of FIG. 29. In some embodiments, the GUI may provide a report of all anomalies detected in the a monitored computer network, and allow users to perform further investigative or mitigation actions based on the report.

Figure 31:
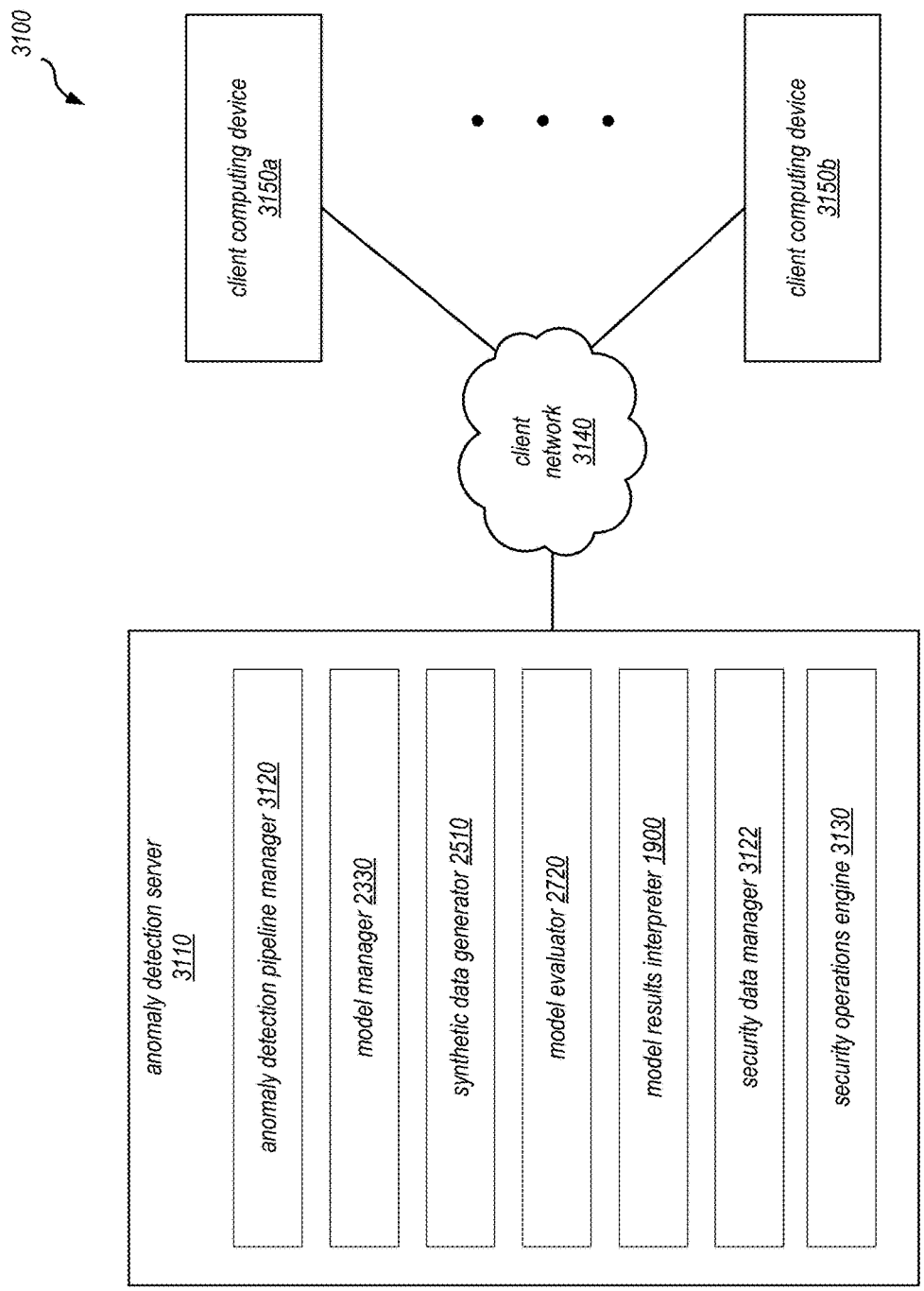
FIG. 31 is a block diagram 3100 of an anomaly detection server used to implement a machine learning anomaly detection system, according to some embodiments.

12. Example Anomaly Detection Server That Implements an Anomaly Detection Pipeline FIG. 31 is a block diagram 3100 illustrating an anomaly detection server 3110, according to some embodiments. In some embodiments, the anomaly detection server 3110 may include one or more computer systems configured to perform various tasks associated with the anomaly detection pipeline 2000 as discussed in connection with FIG. 20, such as: (1) scheduling different anomaly detection jobs for periodic execution. (2) executing anomaly detection jobs according to pipeline configurations. (3) periodically testing, evaluating, and/or modifying the outlier detection models used by the pipeline, and (4) performing security operations based on the detected anomalies.

As shown in this example, the anomaly detection server 3110 is implemented in a client network 3140, which includes a number of client computing devices (3150a and 3150b) to be monitored by the anomaly detection server. The server 3110 may be any type of physical or virtual computing device, and may implement some of all of the following components: an anomaly detection pipeline manager 3120, the model manager 2330 of FIGS. 23, 25, and 27, the synthetic data generator 2510 of FIG. 25, the model evaluator 2720 of FIG. 27, the model results interpreter 1900 of FIG. 19A, a security data manager 3122, and a security operations engine 3130. Depending on the embodiment, some of these components may be implemented on different hosts (possibly external to the client network 3140), as individual nodes (e.g. virtual machines), or over multiple servers or nodes as part of a distributed system. In some embodiments, some of the components shown may be implemented in a platform-as-a-service network such as AMAZON WEB SERVICES or MICROSOFT AZURE.

In some embodiments, the anomaly detection pipeline manager 3120 is tasked with overseeing and orchestrating the execution of the anomaly detection process for batches of observation data (e.g. observation records 130) collected from the client computing devices 3150. In some embodiments, the pipeline manager 3120 may initiate the collection of the observation records. In some embodiments, the pipeline manager may collect data and/or perform anomaly detection according to a set schedule (e.g. once a week). Anomaly detection may be performed on different sets of machines in a client's network, and the results generated by the detection process (e.g. detected outlier processes or hosts) may be used for a weekly hunt performed by security analysts. In some embodiments, the pipeline manager 3120 may execute individual stages in the pipeline by, for example, launching different processes or jobs to pre-process the observation data, reduce the feature dimensionality of the data, execute the various outlier detection models, and aggregating the models' results, as discussed in connection with FIG. 20. In some embodiments, the pipeline manager 3120 may provide a management or configuration interface to allow certain users to view the progress or status of an execution, and to control various operational parameters of the detection process. In some embodiments, the pipeline manager 3120 may provide a notification interface (e.g. an API or an email interface) to alert security analysts or other computer systems about detected anomalies within the observed data.

In some embodiments, the model manager 2330 is tasked with maintaining the various machine learning models used by the pipeline. In some embodiments, different sets of machine learning models may be maintained for different hosts or host categories within the client network 3140. In some embodiments, the models may be stored in a database, which may be accessed via the security data manager 3122. In some embodiments, the model manager 2330 may be configured to perform or orchestrate periodic training and testing of the models using unsupervised machine learning techniques, as discussed in connection with FIG. 21. In some embodiments, the model manager may maintain successive versions of individual models that were trained using observation data in different time periods, and select a version of the model to use for a particular execution of the pipeline. In some embodiments, the model manager 2330 may also apply various configuration parameters to the models, which may be received via configuration interface 2160 of FIG. 21.

In some embodiments, the security data manager 3122 may be used to provide an interface for all data stored by the anomaly detection pipeline. Such data may include, for example, the collected observation data (including historical data collected in previous collection periods), generated synthetic data, the machine learning models, and various configuration and execution metadata associated with the anomaly detection pipeline. In some embodiments, the saved data may also include manual input from security analysts (e.g., the analysts' determinations about a particular outlier process or host). Such information may be used to label the stored observation data, which may be used in some cases to perform supervised training of some machine learning models. In some embodiments, such labeled data may indicate that a process is part of a recognized malicious attack. The features of such a process may be archived in a library so that they can be used to easily detect similar processes in future observation data.

In some embodiments, the security operations engine 3130 may implement various actions to respond to detected cyberattacks, intrusions, breaches, or compromises of the client network 3140. In some embodiments, the security operations engine 3130 may be implemented by many computers that collectively implement the securities operations center (SOC) of a company. In some embodiments, the security operations engine 3130 may implement various reporting interfaces for detected incidents. In some embodiments, the security operations engine 3130 may implement a number of remediation processes or pipelines for responding to detected events, such as to isolate particular parts of the client network or make configuration changes in the network. In some embodiments, the security operations engine 3130 may implement a variety of tools to allow security analysts to more fully investigate a detected anomaly during the hunt process.

As shown in this example, a number of client computing devices 3150 reside in the client network 3140 being monitored by the anomaly detection server 3110. In some embodiments, the client network 3140 may be a virtual network hosted in a platform-as-a-service (PaaS) provider network, such as AMAZON WEB SERVICES, MICROSOFT AZURE, or GOOGLE CLOUD PLAT- FORM. The client computing devices 3150 may encompass many different types of computing resources, including hosts, workstations, servers, mobile devices, or virtual machines, and the like. In this context, a virtual machine may be an instance of a computer and operating system that is emulated and hosted on a physical virtual machine host. The virtual machine host may implement virtualization hardware and/or software (e.g. a hypervisor) to execute and manage multiple instances of guest operating systems. Example implementations of such virtualization technologies include VMWARE ESX/ESXI, MICROSOFT HYPERV, AMAZON WEB SERVICES, MICROSOFT AZURE, GOOGLE CLOUD PLATFORM.

13. Example Networking Environment

Figure 32:
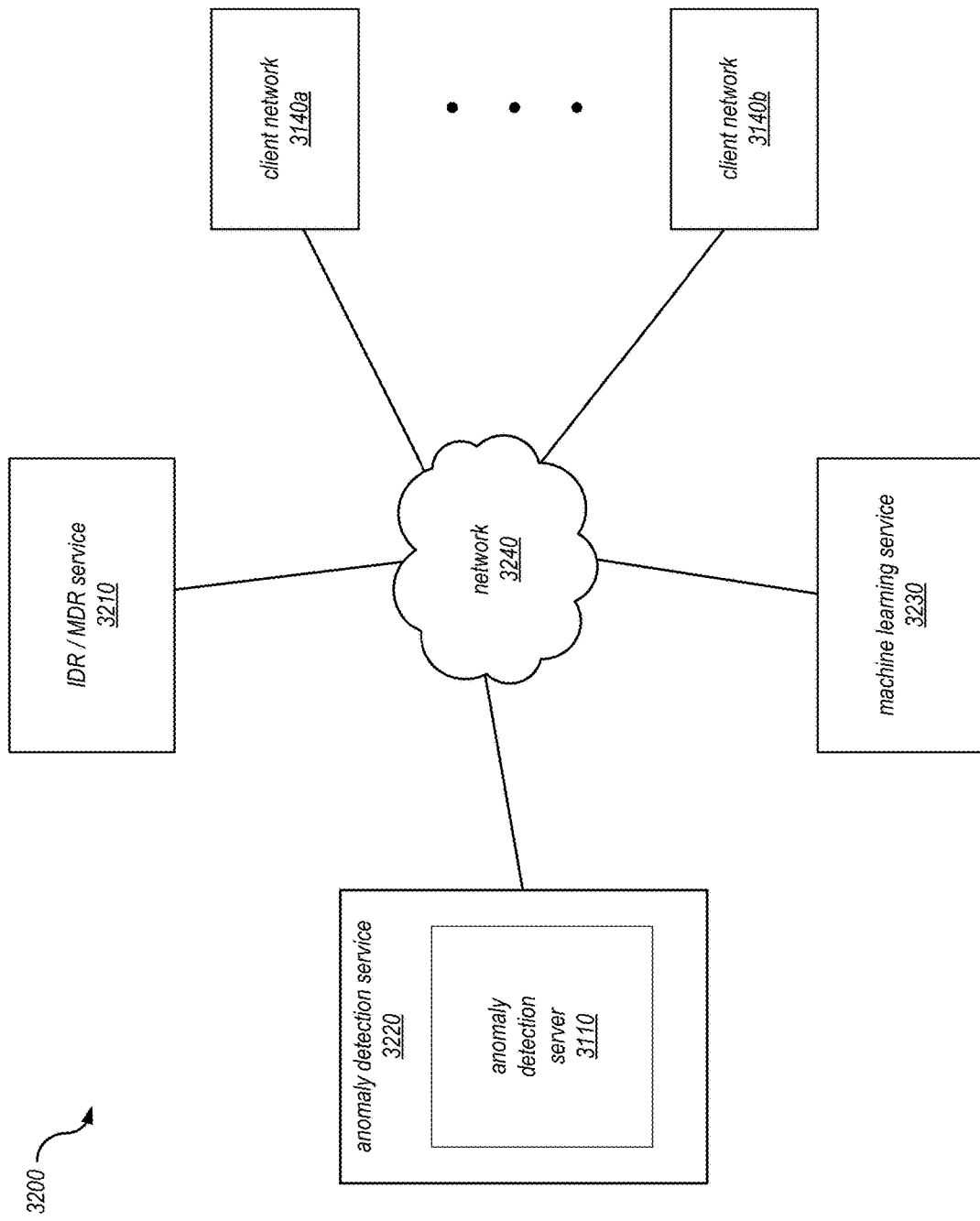
FIG. 32 is a block diagram 3200 of a networked system that implements and uses a machine learning anomaly detection system, according to some embodiments.

FIG. 32 is a block diagram of a networked system, illustrating how an anomaly detection service 3220 is implemented and used using a network 3240.

As shown, the anomaly detection service 3220 is implemented using an anomaly detection server 3110, as discussed in connection with FIG. 31. The anomaly detection service 3220 in this example is communicatively coupled with multiple client computing networks 3140*a* and 3140*b* to monitor for anomalies within those networks. The client networks 3140 may be the private networks of different clients, which may be associated with different entities, companies, organizations, groups, geographic locations, etc.

In some embodiments, the anomaly detection service 3220 may be implemented remotely from the client networks 3140. The anomaly detection service 3220 may be configured to collect or receive observation data from the client networks over the network 3240. In some embodiments, the anomaly detection service 3220 may communicate with data collection agents executing on machines in the client networks. The data collection agents may be configured to periodically gather and upload observation data about the client machines to the anomaly detection service. In some embodiments, the observation data may be collected using one or more proxy or intermediary machines, which may be located in the private network of the client.

In various embodiments, the network 3240 may encompass any suitable combination of networking hardware and protocols necessary to enable communications between the service 3220 and the client networks 3140. In some embodiments, the monitored client devices may execute in a private network of a company, behind a company firewall, and the network 3240 may be a public network such as the Internet, which lies outside the firewall. The network 3240 may encompass the different telecommunications networks and service providers that collectively implement the Internet. In some embodiments, the network 3240 may also include private networks such as private local area networks (LANs), private wide area networks (WANs), or private wireless networks. The network 3240 may be implemented using different hardware (e.g., modems, routers, switches, load balancers, proxy servers, etc.) and software (e.g., protocol stacks, routing software, firewall/security software, etc.) for establishing networking links between the client networks and the anomaly detection service. In some embodiments, communication links between the anomaly detection service 3220 and the client networks 3140 are established using secure communication channels such as transport layer security (TLS) connections.

In some embodiments, the anomaly detection service 3220 may be used by a downstream service such as an incident detection and response (IDR) or managed detection and response (MDR) service 3210 provided by a service provider. Such services may be implemented as outsourced services that provide clients with threat hunting services and respond to threats once they are discovered. In some embodiments, IDR and MDR services employ human security analysts to review and investigate detected anomalies from a monitored client network. In some embodiments, some of these anomalies may be identified using the anomaly detection service 3220. In some embodiments, the anomaly detection service 3220 may be implemented as one of a suite of services used or implemented by the IDR/MDR service 3210. In some embodiments, real-time IDR data with a continuous time component can be used by the anomaly detection service in combination with MDR hunt data to perform anomaly detection.

In some embodiments, the anomaly detection service 3220 may be implemented using a machine learning service 3230, which is also accessible via the network 3240. In some embodiments, the machine learning service 3230 may implement a host of features to build and deploy machine learning models and applications. For example, the machine learning service may provide features to allow model developers to experiment with different types of machine learning models, training dataset features, training techniques, etc. In some embodiments, such a service may be used to host a machine learning model or application to be executed based on periodically collected observation data. In some embodiments, the machine learning service may also allow hosted models to be evaluated and retrained using specified model update processes. Examples of such a machine learning service include AWS SAGEMAKER, AZURE MACHINE LEARNING STUDIO, and GOOGLE AUTOML. In some embodiments, the machine learning service 3230 may be hosted in a cloud-based PaaS service provider network. In some embodiments, all or a portion of anomaly detection service 3220, IDR/MDR service 3210, and client networks 3140 may also be hosted in the PaaS service provider network. In some embodiments, some functions provided by services 3210, 3220, or 3230, or the client networks 3140 may be provided through a remote desktop environment provided by the PaaS provider network.

14. Example Computing Environment

Figure 33:
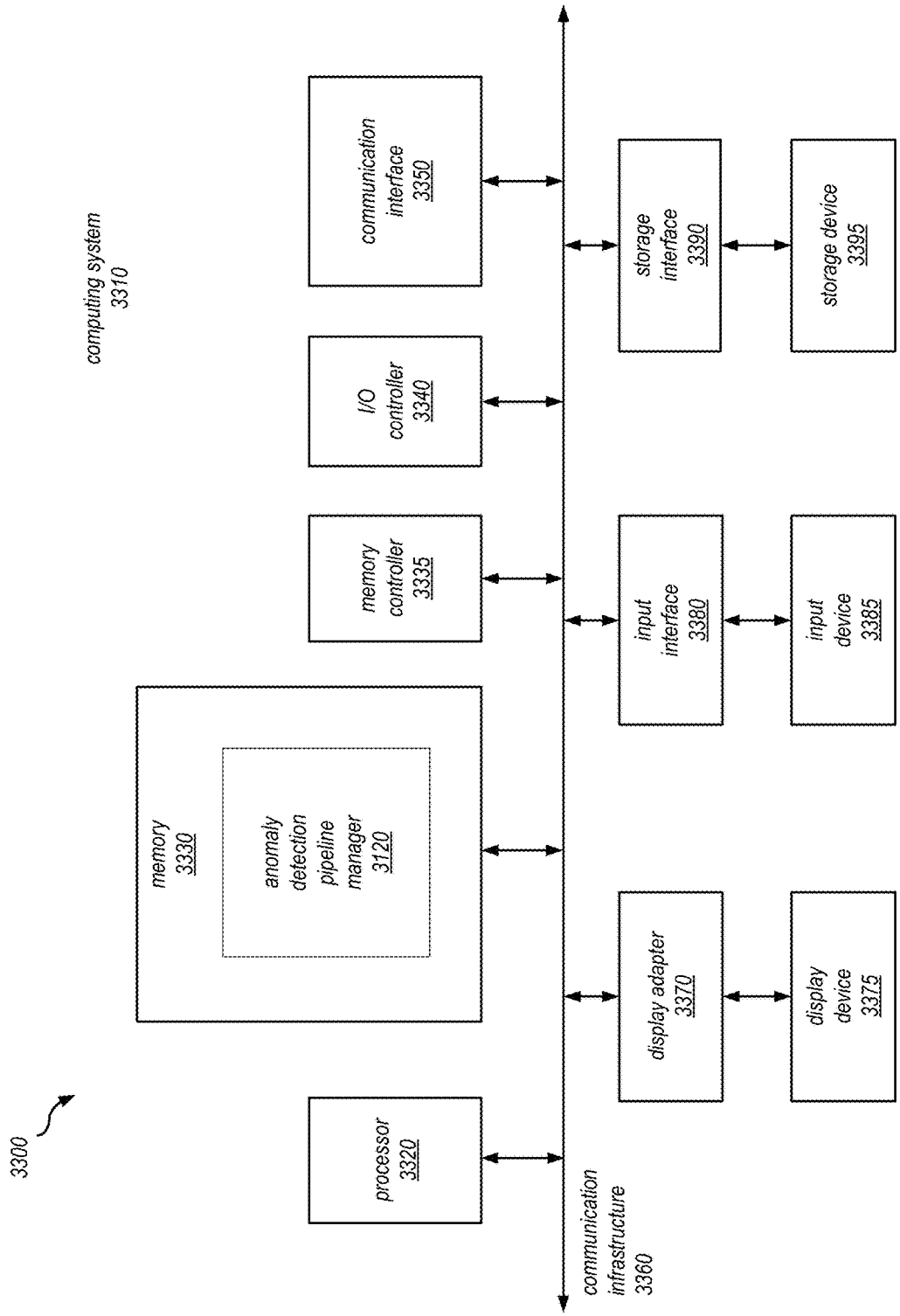
FIG. 33 is a block diagram 3300 of a computing system that may be used to implement one or more portions of a machine learning anomaly detection system, according to some embodiments.

FIG. 33 is a block diagram 3300 of a computing system 3310, which may be used to implement at least a portion of the anomaly detection system or service of FIGS. 31 and 32. For example, computing system 3310 can be used to implement the anomaly detection pipeline manager 3120 of FIG. 31. Computing system 3310 broadly represents a single or multi-processor computing device or system capable of executing computer-readable instructions. Examples of computing system 3310 include, without limitation, any one or more of a variety of devices including workstations, personal computers, laptops, client-side terminals, servers, distributed computing systems, handheld devices, network appliances, storage controllers, and the like. In one configuration, computing system 3310 may include at least one processor 3320 and a memory 3330. By executing the software that implements the anomaly detection pipeline manger 3120, computing system 3310 becomes a special purpose computing device that is configured to perform anomaly detection.

Processor 3320 generally represents any type or form of processing unit capable of processing data or interpreting and executing instructions. In certain embodiments, processor 3320 may receive instructions from a software application or module that may cause processor 3320 to perform the functions of one or more of the embodiments described and/or illustrated herein. For example, processor 3320 may perform and/or be a means for performing all or some of the operations described herein. Processor 3320 may also perform and/or be a means for performing any other operations, methods, or processes described and/or illustrated herein. Memory 3330 generally represents any type or form of volatile or non-volatile storage devices or mediums capable of storing data and/or other computer-readable instructions. Examples include, without limitation, random access memory (RAM), read only memory (ROM), flash memory, or any other suitable memory device. In certain embodiments, computing system 3310 may include both a volatile memory unit and a non-volatile storage device. In one example, program instructions implementing anomaly detection pipeline manager 3120 may be loaded into memory 3330.

In certain embodiments, computing system 3310 may also include one or more components or elements in addition to processor 3320 and/or memory 3330. For example, as shown, computing system 3310 may include a memory controller 3335, an Input/Output (I/O) controller 3340, and a communication interface 3350, each of which may be interconnected via a communication infrastructure. Communication infrastructure 3360 generally represents any type or form of infrastructure capable of facilitating communication between one or more components of a computing device. Examples of communication infrastructure 3360 include, without limitation, a communication bus (such as an Industry Standard Architecture (ISA), Peripheral Component Interconnect (PCI), PCI express (PCIe), or similar bus) and a network.

Memory controller 3335 generally represents any type/form of device capable of handling memory or data or controlling communication between one or more components of computing system 3310. In certain embodiments memory controller 3335 may control communication between processor 3320, memory 3330, and I/O controller 3340 via communication infrastructure 3360, and may perform and/or be a means for performing, either alone or in combination with other elements, one or more of the operations or features described and/or illustrated herein. I/O controller 3340 generally represents any type or form of module capable of coordinating and/or controlling the input and output functions of a computing device. For example, in certain embodiments I/O controller 3340 may control or facilitate transfer of data between one or more elements of computing system 3310, such as processor 3320, memory 3330, communication interface 3350, display adapter 3370, input interface 3380, and storage interface 3390.

Communication interface 3350 broadly represents any type/form of communication device/adapter capable of facilitating communication between computing system 3310 and other devices and may facilitate communication between computing system 3310 and a private or public network. Examples of communication interface 3350 include, a wired network interface (e.g., network interface card), a wireless network interface (e.g., a wireless network interface card), a modem, and any other suitable interface. Communication interface 3350 may provide a direct connection to a remote server via a direct link to a network, such as the Internet, and may also indirectly provide such a connection through, for example, a local area network. Communication interface 3350 may also represent a host adapter configured to facilitate communication between computing system 3310 and additional network/storage devices via an external bus. Examples of host adapters include, Small Computer System Interface (SCSI) host adapters, Universal Serial Bus (USB) host adapters, Serial Advanced Technology Attachment (SATA), Serial Attached SCSI (SAS), Fibre Channel interface adapters, Ethernet adapters, etc.

Computing system 3310 may also include at least one display device 3375 coupled to communication infrastructure 3360 via a display adapter 3370 that generally represents any type or form of device capable of visually displaying information forwarded by display adapter 3370. Display adapter 3370 generally represents any type or form of device configured to forward graphics, text, and other data from communication infrastructure 3360 (or from a frame buffer, as known in the art) for display on display device 3375. Computing system 3310 may also include at least one input device 3385 coupled to communication infrastructure 3360 via an input interface 3380. Input device 3385 generally represents any type or form of input device capable of providing input, either computer or human generated, to computing system 3310. Examples of input device 3385 include a keyboard, a pointing device, a speech recognition device, or any other input device.

Computing system 3310 may also include storage device 3395 coupled to communication infrastructure 3360 via a storage interface 3390. Storage device 3395 generally represents any type or form of storage devices or mediums capable of storing data and/or other computer-readable instructions. For example, storage device 3395 may include a magnetic disk drive (e.g., a so-called hard drive), a floppy disk drive, a magnetic tape drive, an optical disk drive, a flash drive, or the like. Storage interface 3390 generally represents any type or form of interface or device for transmitting data between storage device 3395, and other components of computing system 3310. Storage device 3395 may be configured to read from and/or write to a removable storage unit configured to store computer software, data, or other computer-readable information. Examples of suitable removable storage units include a floppy disk, a magnetic tape, an optical disk, a flash memory device, or the like. Storage device 3395 may also include other similar structures or devices for allowing computer software, data, or other computer-readable instructions to be loaded into computing system 3310. For example, storage device 3395 may be configured to read and write software, data, or other computer-readable information. Storage device 3395 may also be a part of computing system 3310 or may be separate devices accessed through other interface systems.

Many other devices or subsystems may be connected to computing system 3310. Conversely, all of the components and devices illustrated in the figure need not be present to practice the embodiments described and/or illustrated herein. The devices and subsystems referenced above may also be interconnected in different ways from that shown in the figure. Computing system 3310 may also employ any number of software, firmware, and/or hardware configurations. For example, one or more of the embodiments disclosed herein may be encoded as a computer program (also referred to as computer software, software applications, computer-readable instructions, or computer control logic) on a computer-readable storage medium. Examples of computer-readable storage media include magnetic-storage media (e.g., hard disk drives and floppy disks), optical-storage media (e.g., CD- or DVD-ROMs), electronic-storage media (e.g., solid-state drives and flash media), and the like. Such computer programs can also be transferred to computing system 3310 for storage in memory via a network such as the Internet or upon a carrier medium.

The computer-readable medium containing the computer program may be loaded into computing system 3310. All or a portion of the computer program stored on the computer-readable medium may then be stored in memory 3330, and/or various portions of storage device 3395. When executed by processor 3320, a computer program loaded into computing system 3310 may cause processor 3320 to perform and/or be a means for performing the functions of one or more of the embodiments described/illustrated herein. Alternatively, one or more of the embodiments described and/or illustrated herein may be implemented in firmware and/or hardware.

Although the present disclosure has been described in connection with several embodiments, the disclosure is not intended to be limited to the specific forms set forth herein. On the contrary, it is intended to cover such alternatives, modifications, and equivalents as can be reasonably included within the scope of the disclosure.

What is claimed is:

1. A system comprising:
one or more computing devices that implement an anomaly detection system, configured to:
train, using a machine learning technique, an anomaly detection model to detect anomalies in observation records of a plurality of machines, wherein individual ones of the observation records indicate presence or absence of different types of processes on individual ones of the machines;
perform a test of the anomaly detection model, including to:
select a scenario that includes a type of anomaly on at least one machine;
generate a test dataset that includes synthetic test data, wherein the synthetic test data includes (a) at least one anomalous record that contains an anomalous value indicative of the type of anomaly and (b) a plurality of other observation records that do not contain the anomalous value, wherein the anomalous record is generated according to a formula that randomly generates values of the anomalous record based on a selected distance between the anomaly record and a randomly selected one of the other observation records in the test dataset, and wherein the selected distance is checked to verify that the selected distance places the anomalous record at a location in a dimension space of the test dataset that falls below a specified density threshold; and
determine a model performance result of the anomaly detection model using the test dataset; and
based on a determination that the model performance result satisfies a performance criterion, promote the anomaly detection model to be used on real observation records collected from the machines.

2. The system of claim 1, wherein to simulate the scenario, the anomaly detection system is configured to generate the test dataset wherein:
the anomalous record indicates a presence of a particular type of process on the machine; and
the other observation records indicate an absence of the particular type of process on other machines.

3. The system of claim 1, wherein to simulate the scenario, the anomaly detection system is configured to generate the test dataset wherein:
the anomalous record indicates a presence of a particular combination of process types on the machine; and
the other observation records indicate an absence of the particular combination of process types on other machines.

4. The system of claim 1, wherein to simulate the scenario, the anomaly detection system is configured to generate the test dataset wherein:
the anomalous record indicates an observed process type on the machine and a particular set of properties of the observed process type; and
the other observation records indicate the observed process type on other machines without the particular set of properties.

5. The system of claim 1, wherein to simulate the scenario, the anomaly detection system is configured to generate the test dataset wherein:
the anomalous value is associated with a particular set of features; and
the other observation records are altered to randomly vary respective values of the particular set of features.

6. The system of claim 1, wherein the anomaly detection system is configured to:
generate another test dataset that simulates another test scenario, wherein the other test dataset does not include a generated anomalous record; and
apply the anomaly detection model to the other test dataset to determine a false positive metric of the anomaly detection model.

7. The system of claim 1, wherein the location of the anomalous record in the dimension space corresponds to a density value that reflects a probability of observing a data point at the location.

8. The system of claim 1, wherein to generate the anomalous record, the anomaly detection system is configured to select the anomalous value based on an analysis of previous observation records collected from the machines.

9. The system of claim 1, wherein to generate the other observation records, the anomaly detection system is configured to:
generate multiple groups of observation records, wherein each group is generated based on one or more previous observation records collected from the machines.

10. The system of claim 1, wherein to generate the test dataset, the anomaly detection system is configured to:
generate multiple blocks of observation records in the test dataset, wherein each block simulates a different scenario that indicates a different type of anomaly.

11. The system of claim 1, wherein to generate the test dataset, the anomaly detection system is configured to:
select one or more parameters of the test dataset, including:
(a) a number of observation records in the test dataset,
(b) a number of anomalous records in the test dataset, and
(c) a number of observation record features to be varied in the test dataset; and
generate the test dataset according to the selected one or more parameters.

12. The system of claim 11, wherein the anomaly detection system is configured to:
generate multiple test datasets that simulate different scenarios and according to different values of the one or more parameters;

determine, as part of the model performance result for the multiple test datasets, a precision or recall metric of the anomaly detection model for different types of anomalous records; and determine a valid range of anomaly scores of the anomaly detection model that correspond to acceptable values of the precision or recall metric.

13. The system of claim 1, wherein the anomaly detection system is implemented as part of a cyberattack monitoring system, configured to:

periodically collect a dataset of observation records from the machines over a network;

use the anomaly detection system to determine one or more anomalous machines based on the collected dataset; and generate a notification identifying the one or more anomalous machine as a signal of a potential cyberattack.

14. The system of claim 13, wherein the anomaly detection system is configured to:

maintain a group of anomaly detection models used to determine the one or more anomaly machines, wherein the anomaly detection models are periodically trained using collected datasets;

perform periodic tests of the anomaly detection models in the group;

determine, based on a periodic test, that a particular anomaly detection model in the group fails to satisfy the performance criterion; and remove the particular anomaly detection model from the group.

15. A method comprising:

performing, by one or more computing devices that implement an anomaly detection system:

training, using a machine learning technique, an anomaly detection model to detect anomalies in observation records of a plurality of machines, wherein individual ones of the observation records indicate presence or absence of different types of processes on individual ones of the machines;

performing a test of the anomaly detection model, including:

selecting a scenario that includes a type of anomaly on at least one machine;

generating a test dataset that includes synthetic test data, wherein the synthetic test data includes (a) at least one anomalous record that contains an anomalous value indicative of the type of anomaly and (b) a plurality of other observation records that do not contain the anomalous value, wherein the anomalous record is generated according to a formula that randomly generates values of the anomalous record based on a selected distance between the anomaly record and a randomly selected one of the other observation records in the test dataset, and wherein the selected distance is checked to verify that the selected distance places the anomalous record at a location in a dimension space of the test dataset that falls below a specified density threshold; and determining a model performance result of the anomaly detection model using the test dataset; and based on a determination that the model performance result satisfies a performance criterion, promoting the anomaly detection model to be used on real observation records collected from the machines.

16. The method of claim 15, wherein simulating the scenario comprises generating the test dataset wherein:

the anomalous record indicates a presence of a particular type of process on the machine; and the other observation records indicate an absence of the particular type of process on other machines.

17. The method of claim 15, wherein generating the test dataset comprises altering the other observation records to randomly vary a set of features associated with the anomalous value.

18. The method of claim 15, wherein performing the test of the anomaly detection model comprises:

generating another test dataset that simulates another test scenario, wherein the other test dataset does not include a generated anomalous record; and applying the anomaly detection model to the other test dataset to determine a false positive metric of the anomaly detection model.

19. The method of claim 15, further comprising:

generating multiple test datasets that simulate different scenarios and according to different dataset parameters;

determining, as part of the model performance result for the multiple test datasets, a precision or recall metric of the anomaly detection model for different types of anomalous records; and determining a valid range of anomaly scores of the anomaly detection model that correspond to acceptable values of the precision or recall metric.

20. The method of claim 15, wherein the distance is a Euclidean distance or a Hamming distance.

* * * * *